(12) United States Patent
Jung et al.

(10) Patent No.: US 8,828,559 B2
(45) Date of Patent: Sep. 9, 2014

(54) HETEROCYCLIC COMPOUND AND ORGANIC LIGHT-EMITTING DEVICE INCLUDING THE SAME

(75) Inventors: Hye-Jin Jung, Yongin (KR); Seok-Hwan Hwang, Yongin (KR); Young-Kook Kim, Yongin (KR); Jin-O Lim, Yongin (KR); Sang-Hyun Han, Yongin (KR); Soo-Yon Kim, Yongin (KR); Dae-Yup Shin, Yongin (KR)

(73) Assignee: Samsung Display Co., Ltd., Giheung-Gu, Yongin, Gyeonggi-Do (KR)

(*) Notice: Subject to any disclaimer, the term of this patent is extended or adjusted under 35 U.S.C. 154(b) by 190 days.

(21) Appl. No.: 13/444,938

(22) Filed: Apr. 12, 2012

(65) Prior Publication Data

US 2013/0113367 A1     May 9, 2013

(30) Foreign Application Priority Data

Nov. 3, 2011 (KR) .................. 10-2011-0114117

(51) Int. Cl.
*H01L 51/54* (2006.01)

(52) U.S. Cl.
USPC ........... 428/690; 428/917; 313/504; 313/505; 313/506; 257/40; 257/E51.05; 257/E51.026; 257/E51.032; 548/304.1; 548/418; 548/440; 548/444; 564/26; 564/426; 564/432; 564/434; 585/27

(58) Field of Classification Search
USPC .................. 428/690, 917; 313/504, 505, 506; 257/40, E51.05, E51.026, E51.032; 548/304.1, 418, 440, 444; 585/27; 564/26, 426, 432, 434
See application file for complete search history.

(56) References Cited

U.S. PATENT DOCUMENTS

| | | | |
|---|---|---|---|
| 7,053,255 B2 | 5/2006 | Ikeda et al. |
| 7,233,019 B2 | 6/2007 | Ionkin et al. |
| 7,571,894 B2 | 8/2009 | Sotoyama |
| 7,879,462 B2 | 2/2011 | Lyu et al. |
| 2006/0147750 A1 | 7/2006 | Ujiie et al. |
| 2009/0039769 A1 | 2/2009 | Matsunami et al. |
| 2009/0179551 A1 | 7/2009 | Kwon et al. |
| 2010/0081846 A1 | 4/2010 | Kim et al. |

FOREIGN PATENT DOCUMENTS

| | | | |
|---|---|---|---|
| KR | 10-2006-0006760 A | 1/2006 |
| KR | 10-2006-0052312 A | 5/2006 |
| KR | 10-2006-0111048 A | 10/2006 |
| KR | 10-2006-0113254 A | 11/2006 |
| KR | 10-2007-0054120 A | 5/2007 |
| KR | 10-0835601 B1 | 5/2008 |
| KR | 10-2008-0059082 A | 6/2008 |
| KR | 10-2010-0108903 A | 10/2010 |
| KR | 10-2010-0118258 A | 11/2010 |
| KR | 10-2011-0021487 A | 3/2011 |
| WO | WO 2011025282 | * 3/2011 | ............. C09K 11/06 |

* cited by examiner

*Primary Examiner* — Gregory Clark
(74) *Attorney, Agent, or Firm* — Robert E. Bushnell, Esq.

(57) ABSTRACT

A heterocyclic compound represented by Formula 1A and an organic light-emitting device including the heterocyclic compound:

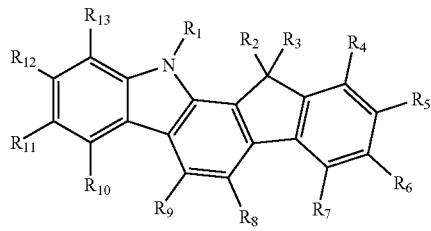
Formula 1A

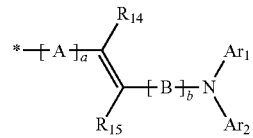
Formula 1B at least one of $R_1$ to $R_{13}$ is a group represented by Formula 1B below:

wherein $R_1$ to $R_{15}$, $Ar_1$, $Ar_2$, A, B, a, and b are defined as in the specification. The organic light-emitting device may include an organic layer containing the heterocyclic compound, and thus may have a low driving voltage, a high-emission efficiency, and long lifespan characteristics.

30 Claims, 1 Drawing Sheet

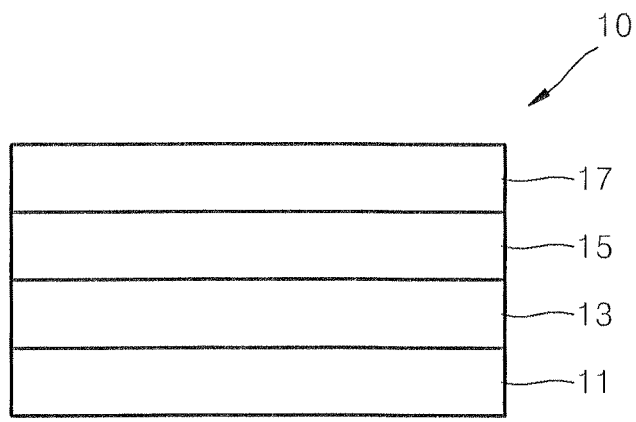

HETEROCYCLIC COMPOUND AND ORGANIC LIGHT-EMITTING DEVICE INCLUDING THE SAME

CROSS-REFERENCE TO RELATED PATENT APPLICATION

This application makes reference to, incorporates the same herein, and claims all benefits accruing under 35 U.S.C. §119 from an application earlier filed in the Korean Intellectual Property Office on 3 Nov. 2011 and there duly assigned Serial No. 10-2011-0114117.

BACKGROUND OF THE INVENTION

1. Field of the Invention

The present invention relates to a heterocyclic compound and an organic light-emitting device including the heterocyclic compound.

2. Description of the Related Art

Organic light-emitting diode (OLEDs), which are self-emitting devices, have advantages such as wide viewing angles, excellent contrast, quick response, high brightness, excellent driving voltage characteristics, and can provide multicolored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows. When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

SUMMARY

The present invention provides a novel heterocyclic compound for an organic light-emitting device with a low voltage, a high luminance, a high efficiency, and a long lifespan.

According to an aspect of the present invention, there is provided a heterocyclic compound represented by Formula 1A below:

Formula 1A

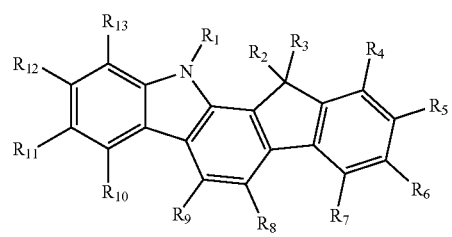

wherein, in Formula 1A, $R_1$ to $R_{13}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, a $-N(Q_1)(Q_2)$ group, and a group represented by Formula 1B below, wherein $Q_1$ and $Q_2$ are each independently one of a hydrogen atom, a deuterium atom, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_3$-$C_{30}$ heteroaryl group:

Formula 1B

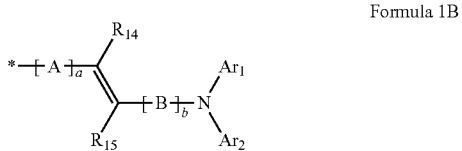

wherein, in Formula 1B, $R_{14}$ and $R_{15}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, and a substituted or unsubstituted $C_5$-$C_{30}$ arylthio group;

at least one of $R_1$ to $R_{13}$ is a group represented by Formula 1B above;

$Ar_1$ and $Ar_2$ are each independently a substituted or unsubstituted $C_5$-$C_{30}$ aryl group or a substituted or unsubstituted $C_3$-$C_{30}$ heteroaryl group, wherein $Ar_1$ and $Ar_2$ are optionally linked to each other;

A and B are a divalent linker, and are each independently one of a substituted or unsubstituted $C_5$-$C_{30}$ arylene group or a substituted or unsubstituted $C_3$-$C_{30}$ heteroarylene group; and a is an integer from 0 to 3, and b is an integer from 0 to 3, wherein if a is 2 or greater, the two or more A are identical to or different from each other, and if b is 2 or greater, the two or more B are identical to or different from each other.

According to another aspect of the present invention, there is provided an organic light-emitting device including: a first electrode; a second electrode disposed opposite to the first electrode; and an organic layer disposed between the first electrode and the second electrode, wherein the organic layer includes at least one layer, and includes at least one of the heterocyclic compounds represented by Formula 1A above.

BRIEF DESCRIPTION OF THE DRAWING

The above and other features and advantages of the present invention will become more apparent by describing in detail exemplary embodiments thereof with reference to the attached drawing in which:

FIG. 1 schematically illustrates the structure of an organic light-emitting device according to an embodiment of the present invention.

DETAILED DESCRIPTION OF EXEMPLARY EMBODIMENTS

As used herein, the term "and/or" includes any and all combinations of one or more of the associated listed. Expressions such as "at least one of," when preceding a list of elements, modify the entire list of elements and do not modify the individual elements of the list.

According to an aspect of the present invention, there is provided a heterocyclic compound represented by Formula 1A:

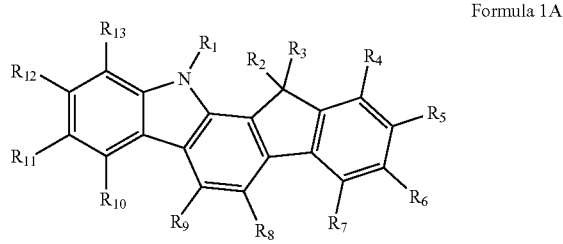

Formula 1A wherein, in Formula 1A, $R_1$ to $R_{13}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, a —N($Q_1$)($Q_2$) group, and a group represented by Formula 1B below, wherein $Q_1$ and $Q_2$ are each independently one of a hydrogen atom, a deuterium atom, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_3$-$C_{30}$ heteroaryl group;

at least one of $R_1$ to $R_{13}$ is a group represented by Formula 1B below;

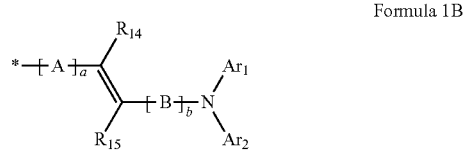

Formula 1B wherein, in Formula 1B, $R_{14}$ and $R_{15}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, and a substituted or unsubstituted $C_5$-$C_{30}$ arylthio group;

$Ar_1$ and $Ar_2$ are each independently a substituted or unsubstituted $C_5$-$C_{30}$ aryl group or a substituted or unsubstituted $C_3$-$C_{30}$ heteroaryl group, wherein $Ar_1$ and $Ar_2$ may be optionally linked to each other;

A and B are a divalent linker, and are each independently one of a substituted or unsubstituted $C_5$-$C_{30}$ arylene group or a substituted or unsubstituted $C_3$-$C_{30}$ heteroarylene group;

a is an integer from 0 to 3, and b is an integer from 0 to 3, wherein if a is 2 or greater, the two or more A are identical to or different from each other, and if b is 2 or greater, the two or more B are identical to or different from each other; and

* indicates a binding site.

For example, $Ar_1$ and $Ar_2$ may be each independently one of a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolyl group, a substituted or unsubstituted pyridoindolyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, and a substituted or unsubstituted tetrazolyl group.

For example, $Ar_1$ and $Ar_2$ may be each independently one of the groups represented by Formulae 2A to 2J below, but are not limited thereto:

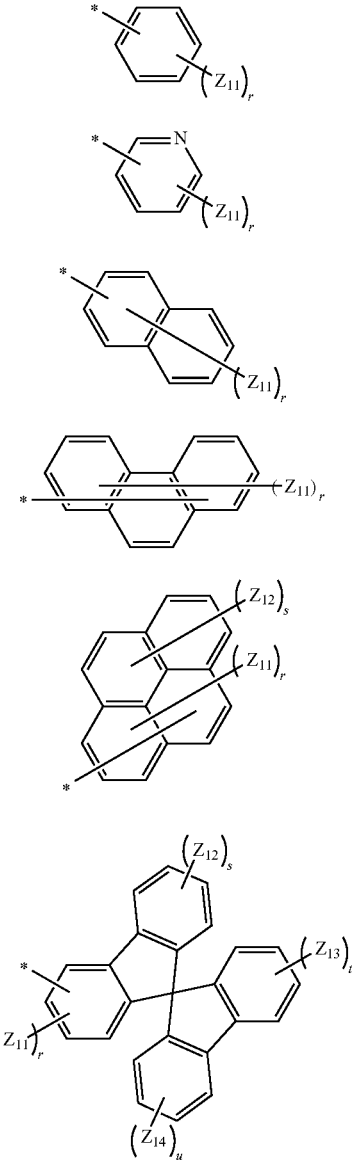

Formula 2A

Formula 2B

Formula 2C

Formula 2D

Formula 2E

Formula 2F

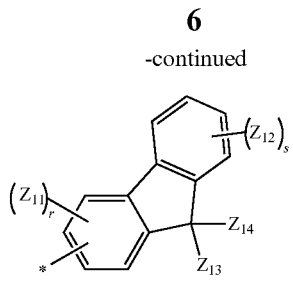

Formula 2G

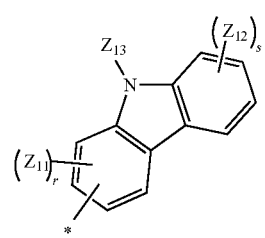

Formula 2H

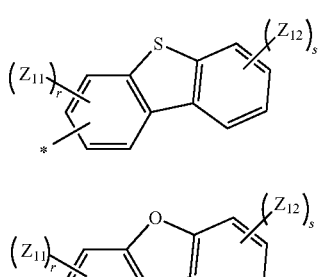

Formula 2I

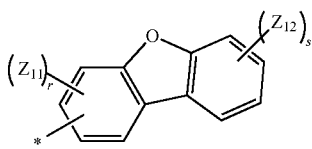

Formula 2J

In Formulae 2A to 2J, $Z_{11}$, $Z_{12}$, $Z_{13}$, and $Z_{14}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolyl group;

a plurality of $Z_{11}$, $Z_{12}$, $Z_{13}$, and $Z_{14}$ may be identical to or different from each other;

r is an integer from 1 to 9;

s is an integer from 1 to 5;

t is an integer from 1 to 4;

u is an integer from 1 to 4; and

* indicates a binding site.

For example, $Ar_1$ and $Ar_2$ may be each independently one of the groups represented by Formulae 3A to 3S below, but are not limited thereto:

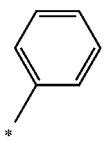

Formula 3A

Formula 3B

Formula 3C

Formula 3D

Formula 3E

Formula 3F

Formula 3G

Formula 3H

Formula 3I

Formula 3J

Formula 3K

Formula 3L

Formula 3M

Formula 3N

Formula 3O

Formula 3P

Formula 3Q

Formula 3R

-continued

Formula 3S

In Formulae 3A to 3S, * indicates a binding site.

A and B may be each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group.

For example, A and B may be each independently one of the groups represented by Formulae 4A to 4L below, but are not limited thereto:

Formula 4A

Formula 4B

Formula 4C

Formula 4D

Formula 4E

Formula 4F

Formula 4G

Formula 4H

Formula 4I

Formula 4J

Formula 4K

Formula 4L

In Formulae 4A to 4L, $Z_{21}$, $Z_{22}$, and $Z_{23}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, and a substituted or unsubstituted pyridinyl group, wherein a plurality of $Z_{21}$, $Z_{22}$, and $Z_{23}$ may be identical to or different from each other;

v, w, and x are an integer from 1 to 4; and

* and *' indicate binding sites.

For example, A and B may be each independently one of the groups represented by Formulae 5A to 5R below, but are not limited thereto:

Formula 5A
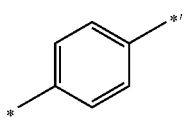
Formula 5B
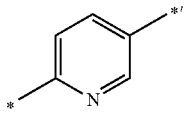
Formula 5C
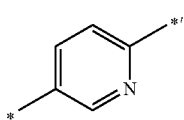
Formula 5D
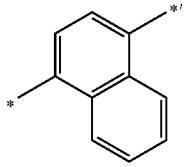
Formula 5E
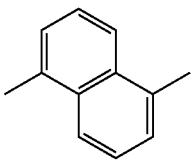
Formula 5F
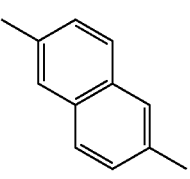
Formula 5G
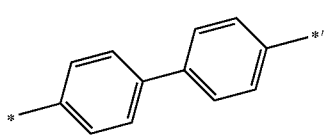
Formula 5H
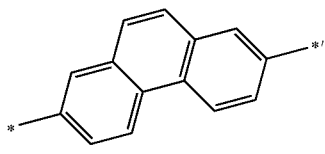
Formula 5I
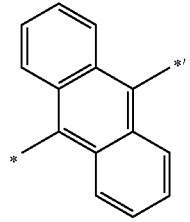
Formula 5J
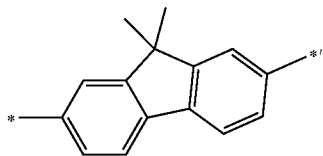
Formula 5K
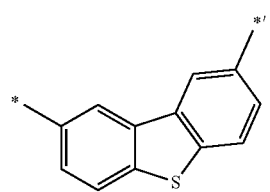
Formula 5L
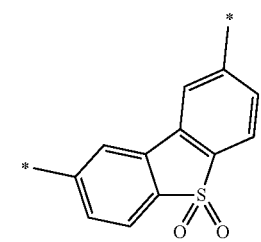
Formula 5M
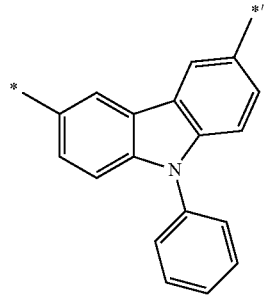
Formula 5N
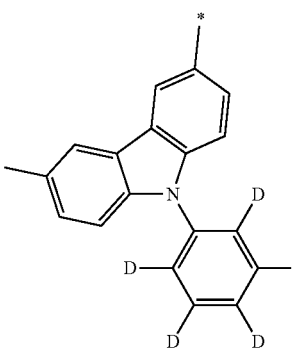
Formula 5O
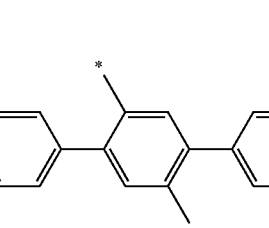
Formula 5P
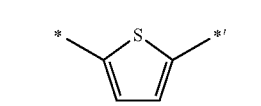

Formula 5Q

Formula 5R

In Formulae 5A to 5R, * and *' indicate binding sites.

$R_1$ to $R_{13}$ may be each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted carbazolyl group, a substituted or unsubstituted pyranyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolinyl group, a substituted or unsubstituted benzoimidazolyl group, a substituted or unsubstituted benzooxazolyl group, a substituted or unsubstituted pentalenyl group, a substituted or unsubstituted indenyl group, a substituted or unsubstituted pyrrolyl group, a substituted or unsubstituted imidazolyl group, a substituted or unsubstituted pyrazolyl group, a $N(Q_1)(Q_2)$ group, and a group represented by Formula 1B above, wherein $Q_1$ and $Q_2$ may be each independently one of a hydrogen atom, a deuterium atom, a halogen atom, a hydroxyl group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group.

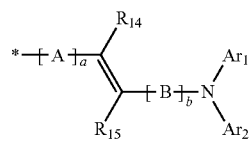

Formula 1B

In Formula 1B, $R_{14}$ and $R_{15}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted naphthyl group, a substituted or unsubstituted anthryl group, and a substituted or unsubstituted pyridinyl group, and a substituted or unsubstituted phenanthrenyl group;

$Ar_1$ and $Ar_2$ may be each independently one of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, a substituted or unsubstituted spiro-fluorenyl group, and a substituted or unsubstituted oxadiazolyl group;

A and B may be each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group; and a is an integer from 0 to 2, and b is an integer from 0 to 2, wherein if a is 2, the two A are identical to or different from each other, and if b is 2, the two B are identical to or different from each other.

For example, $R_1$ to $R_{13}$ may be each independently one of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a group represented by Formula 1B above, and groups represented by Formulae 6A to 6G below; and $R_{14}$ and $R_{15}$ may be each independently one of a hydrogen atom, a deuterium atom, and the groups represented by Formulae 6A to 6L below, but are not limited thereto:

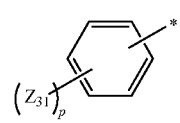

Formula 6A

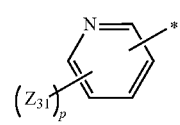

Formula 6B

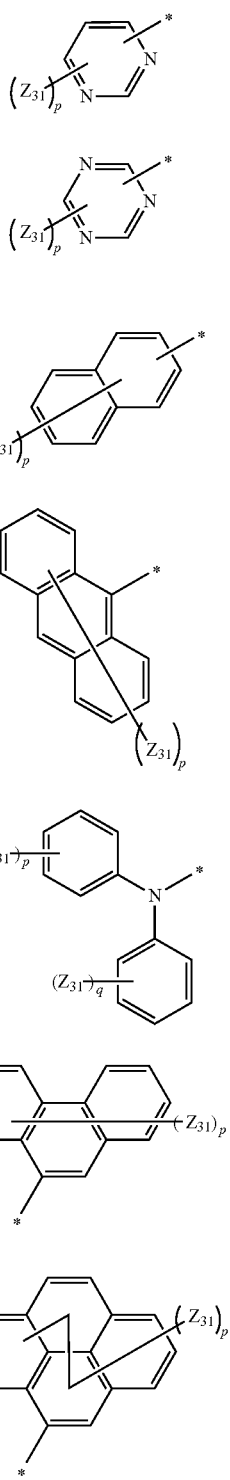

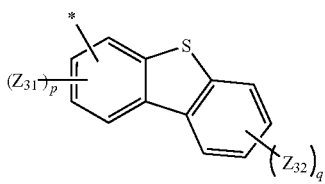

Formula 6C

Formula 6D

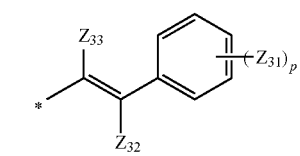

Formula 6E

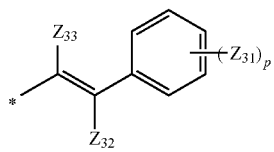

Formula 6K

Formula 6L

In Formulae 6A to 6L, $Z_{31}$, $Z_{32}$, and $Z_{33}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted carbazolyl group, a substituted or unsubstituted quinolyl group, and a $N(Q_{11})(Q_{12})$ group, wherein $Q_{11}$ and $Q_{12}$ may be each independently one of a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group;

a plurality of $Z_{31}$ and $Z_{32}$ may be identical to or different from each other;

p may be an integer from 1 to 9;

q may be an integer from 1 to 5; and

* indicates a binding site.

For example, $R_1$ to $R_{13}$ may be each independently one of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, a cyano group, $-CD_3$, $-CF_3$, a group represented by Formula 1B above, and groups represented by Formulae 7A to 7S below, but are not limited thereto.

$R_{14}$ and $R_{15}$ may be each independently one of a hydrogen atom, a deuterium atom, and the groups represented by Formulae 7A to 7H below, but are not limited thereto:

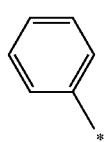

Formula 7A

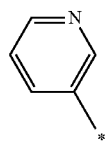
Formula 7B
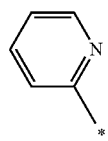
Formula 7C
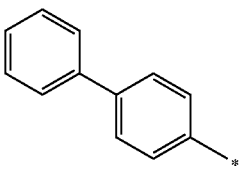
Formula 7D
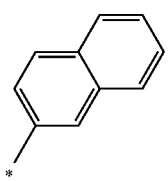
Formula 7E
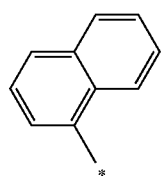
Formula 7F
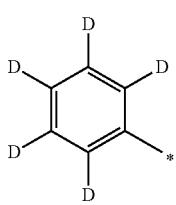
Formula 7G
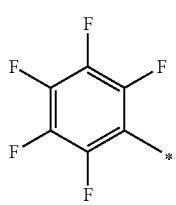
Formula 7H
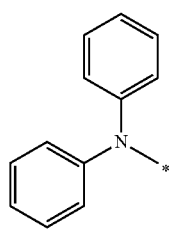
Formula 7I
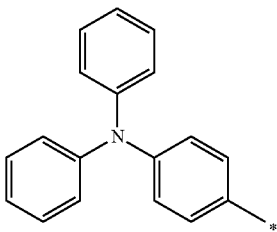
Formula 7J
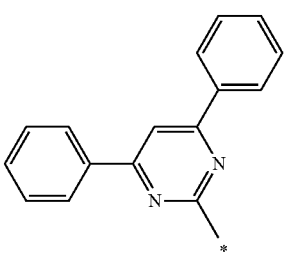
Formula 7K
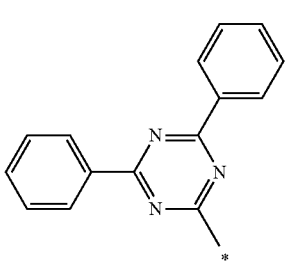
Formula 7L
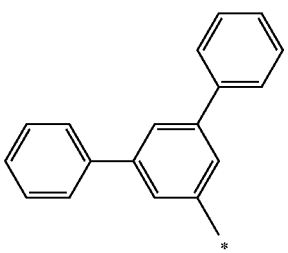
Formula 7M
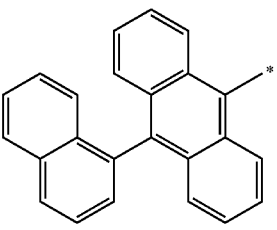
Formula 7N
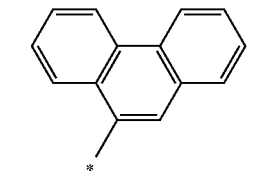
Formula 7O Formula 7P

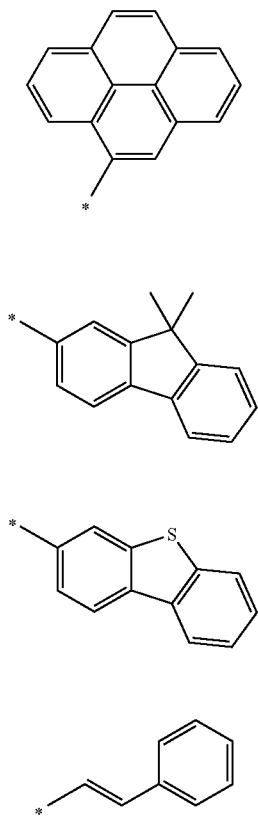

Formula 7Q

Formula 7R

Formula 7S

In Formulae 7A to 7S, * indicates a binding site.

The heterocyclic compound of Formula 1A above may be a compound represented by Formula 1C, 1D, or 1E below:

Formula 1C

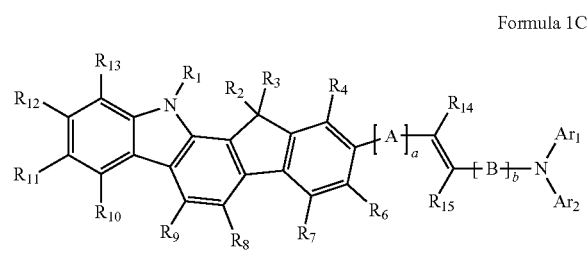

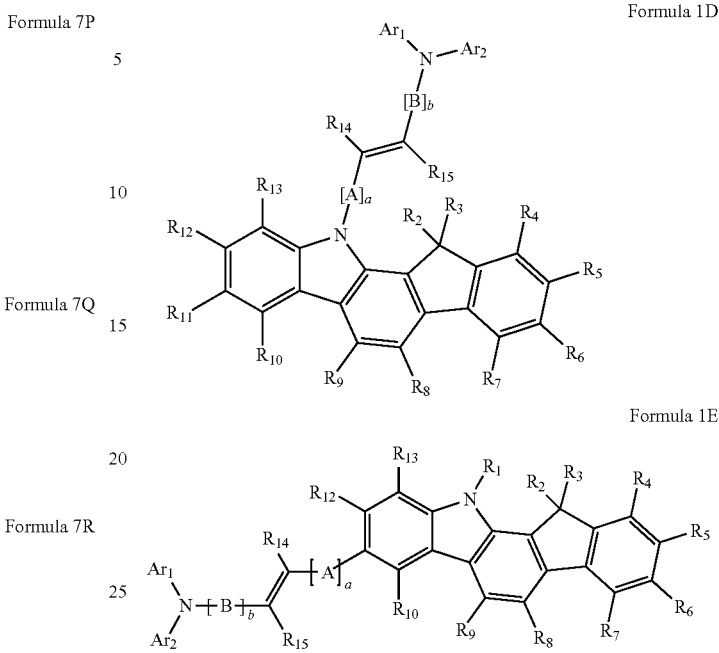

In Formulae 1C, 1D and 1E, $Ar_1$ and $Ar_2$ may be each independently one of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, a substituted or unsubstituted spiro-fluorenyl group, and a substituted or unsubstituted oxadiazolyl group;

A and B may be each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group;

a is an integer from 0 to 2, and b is an integer from 0 to 2, wherein if a is 2, the two A are identical to or different from each other, and if b is 2, the two B are identical to or different from each other;

$R_1$ to $R_{13}$ may be each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted carbazolyl group, a substituted or unsubstituted pyranyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolinyl group, a substituted or unsubstituted benzoimidazolyl group, a substituted or unsubstituted benzooxazolyl group, a substituted or unsubstituted pentalenyl group, a substituted or unsubstituted indenyl group, a substituted or unsubstituted pyrrolyl group, a substituted or unsubstituted imidazolyl group, a substituted or unsubstituted pyrazolyl group, and a $N(Q_1)(Q_2)$ group, wherein $Q_1$ and $Q_2$ may be each independently one of a hydrogen atom, a deuterium atom, a halogen atom, a hydroxyl group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group; and $R_{14}$ and $R_{15}$ may be each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted naphthyl group, a substituted or unsubstituted anthryl group, and a substituted or unsubstituted pyridinyl group, and a substituted or unsubstituted phenanthrenyl group.

In some embodiments, in Formulae 1C, 1D and 1E, $Ar_1$ and $Ar_2$ may each independently one of the groups represented by Formulae 2A to 2J above. In some other embodiments, in Formulae 1C, 1D and 1E, $Ar_1$ and $Ar_2$ may each independently one of the groups represented by Formulae 3A to 3S above.

In still other embodiments, in Formulae 1C, 1D and 1E, A and B may each independently one of the groups represented by Formulae 4A to 4L above. In yet still other embodiments, in Formulae 1C, 1D and 1E, A and B may each independently one of the groups represented by Formulae 5A to 5R above.

In some embodiments, in Formulae 1C, 1D and 1E, $R_1$ to $R_{13}$ may be each independently one of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, and the groups represented by Formulae 6A to 6L above; and $R_{14}$ and $R_{15}$ may each independently one of a hydrogen atom, a deuterium atom, and the groups represented by Formulae 6A to 6L above. In some other embodiments, in Formulae 1C, 1D and 1E, $R_1$ to $R_{13}$ may be each independently one of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, a cyano group, —$CD_3$, —$CF_3$, and groups represented by Formulae 7A to 7S below; and $R_{14}$ and $R_{15}$ may each independently one of a hydrogen atom, a deuterium atom, and the groups represented by Formulae 7A to 7H above.

The heterocyclic compound represented by Formula 1A above may be one of the Compounds 1 to 75 below, but is not limited thereto:

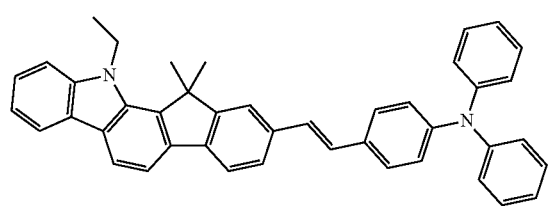

1

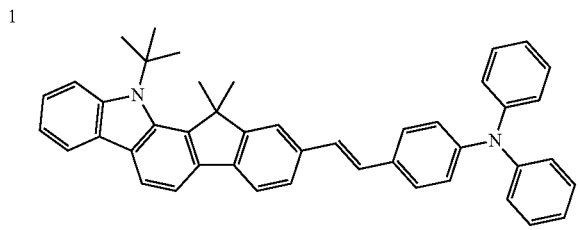

2

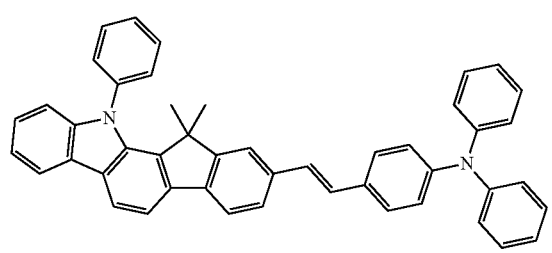

3

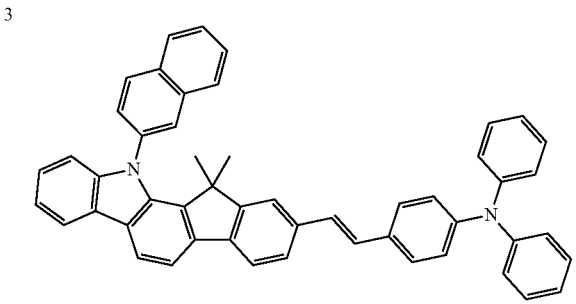

4

-continued
5
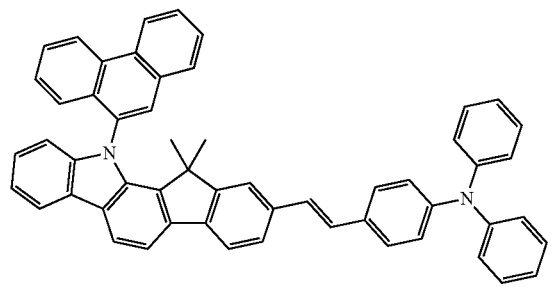
6
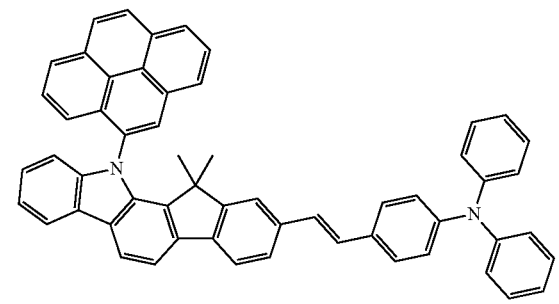
7
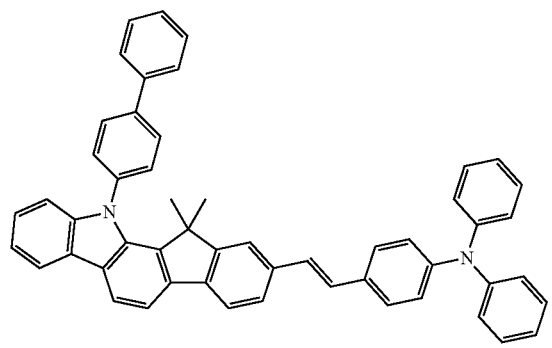
8
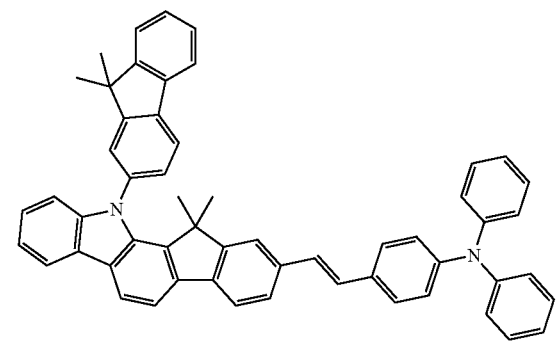
9
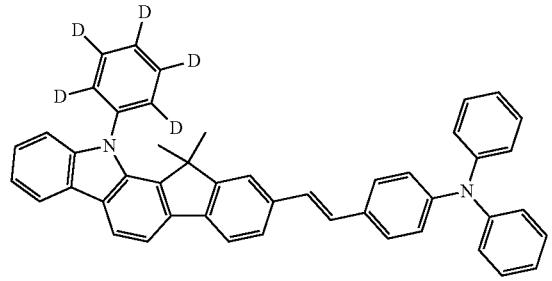
10
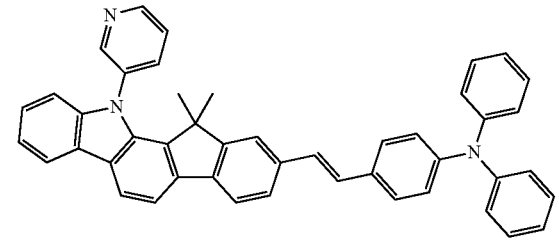
11
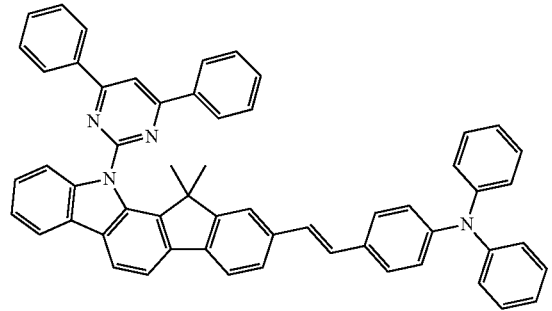
12
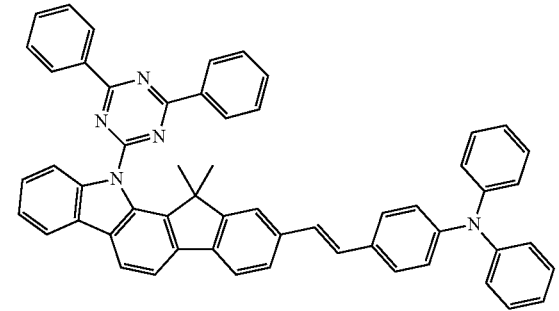
13
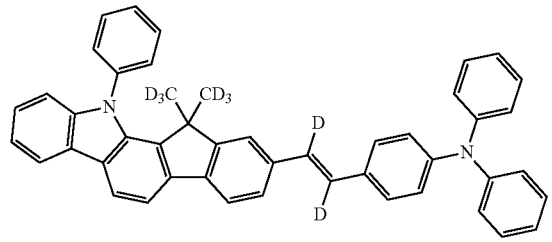
14
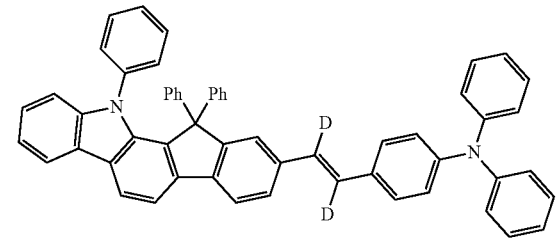

-continued
15
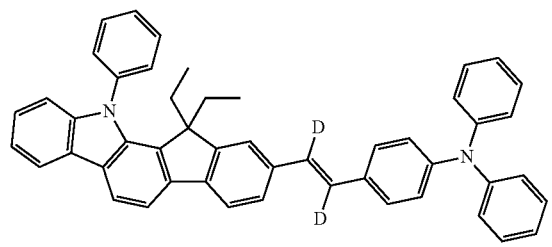
16
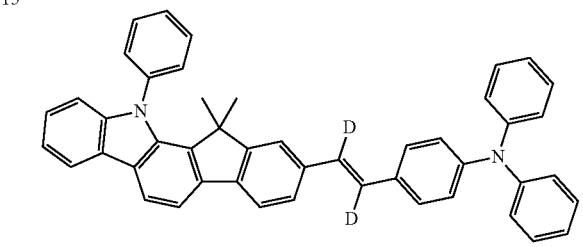
17
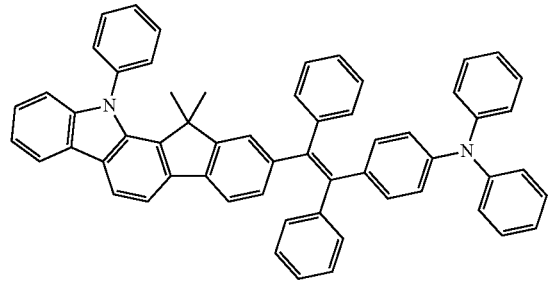
18
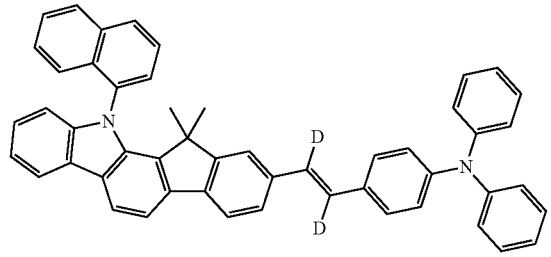
19
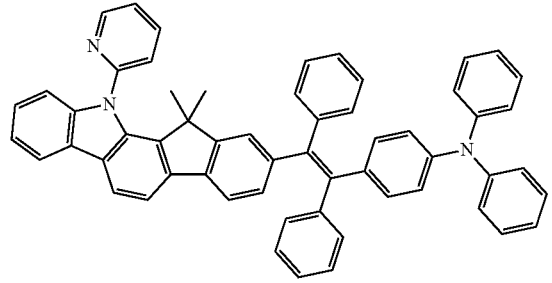
20
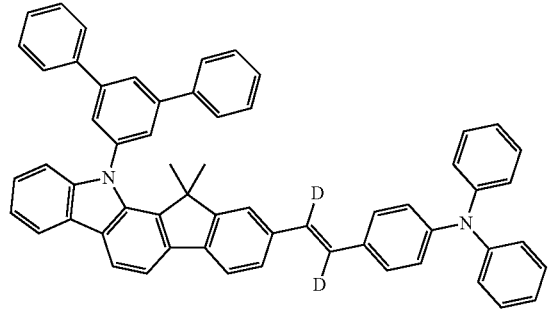
21
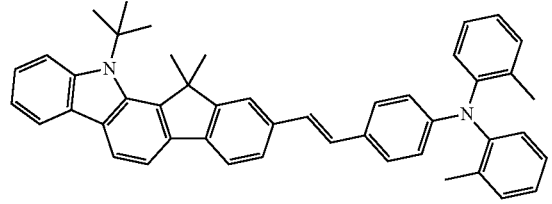
22
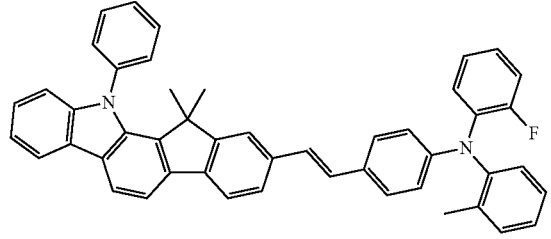
23
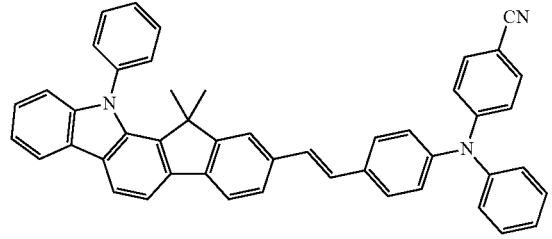
24
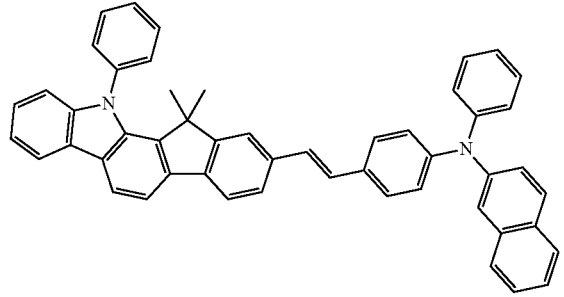

-continued
25
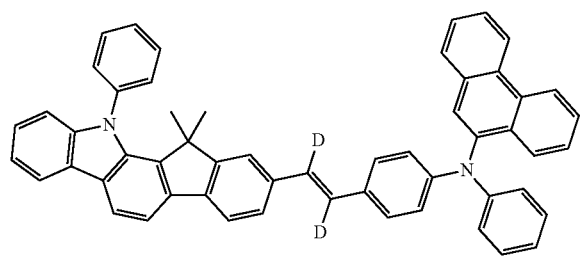
26
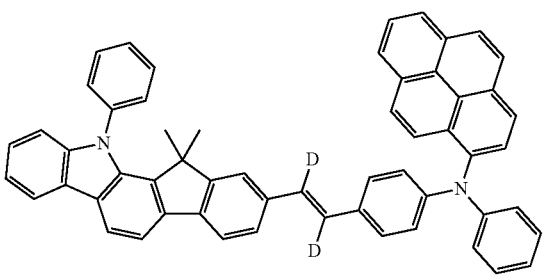
27
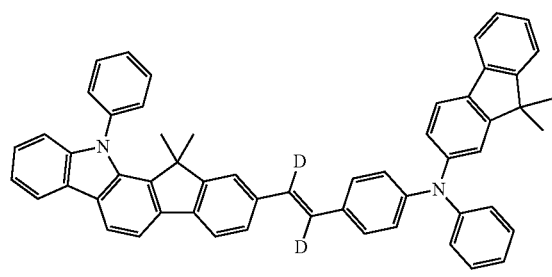
28
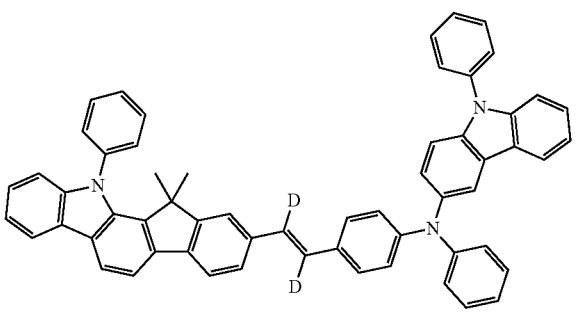
29
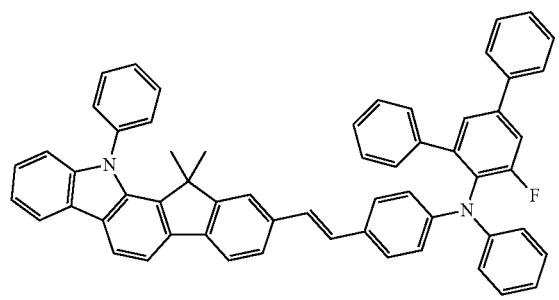
30
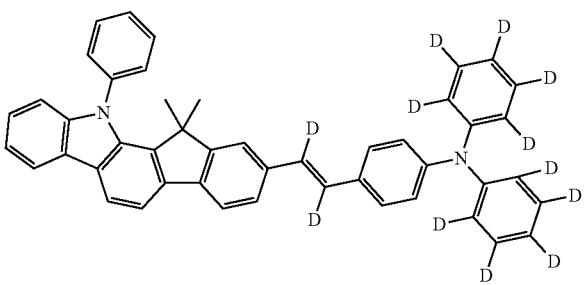
31
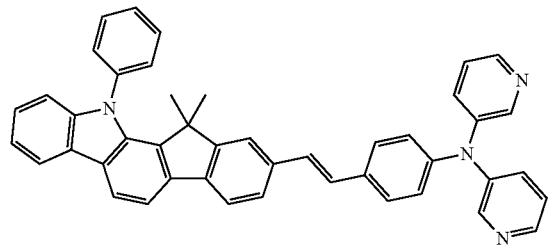
32
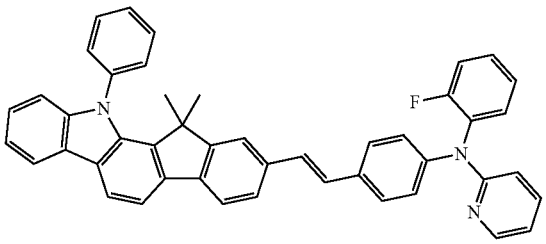
33
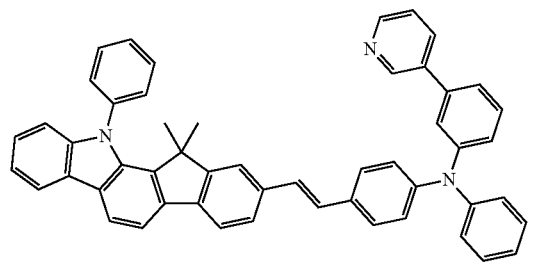
34
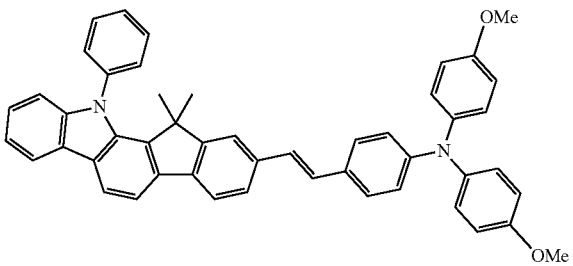

35
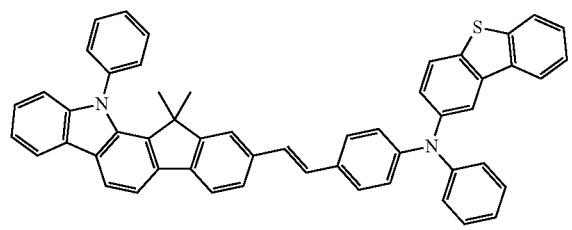
36
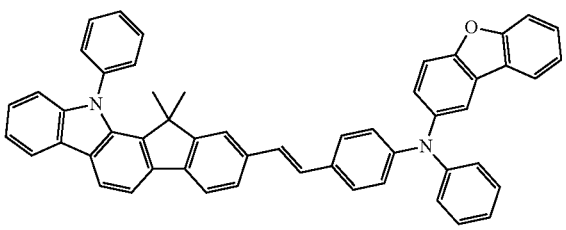
37
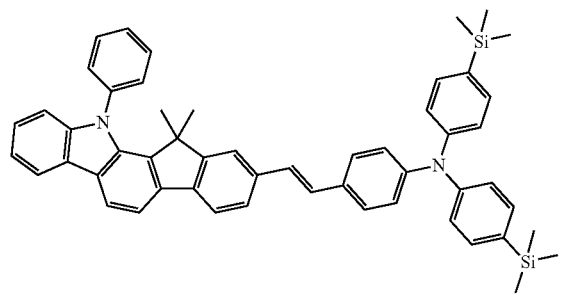
38
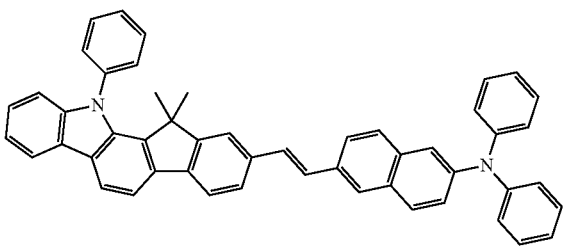
39
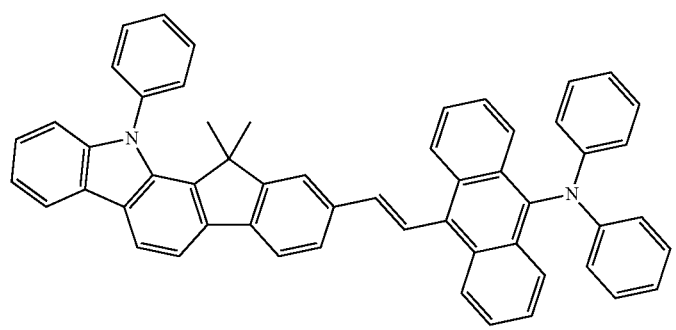
40
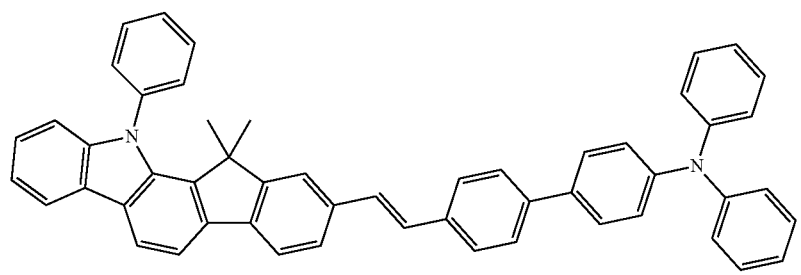
41
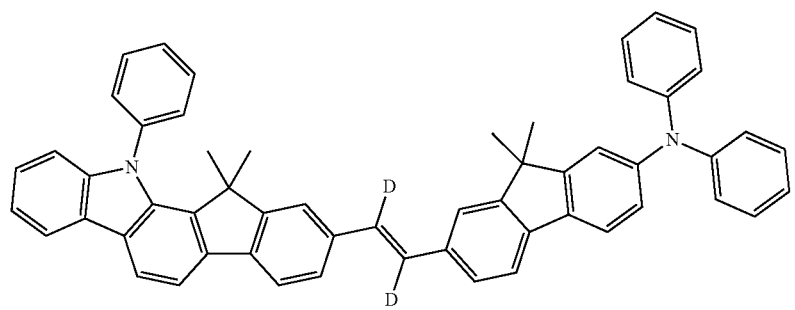

42
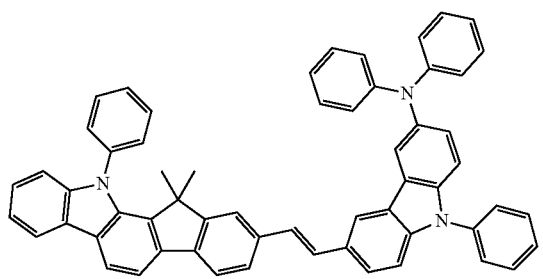
43
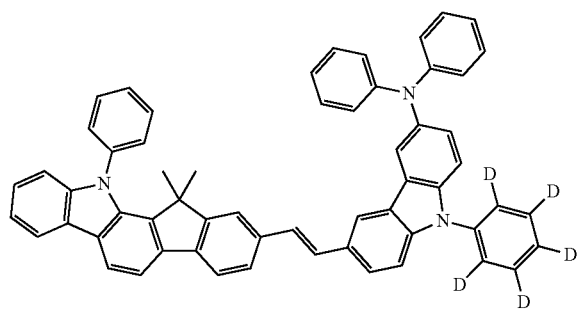
44
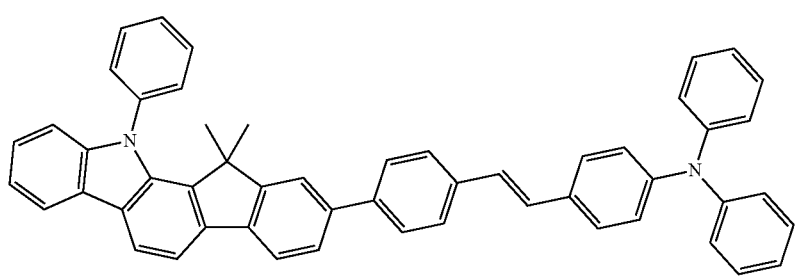
45
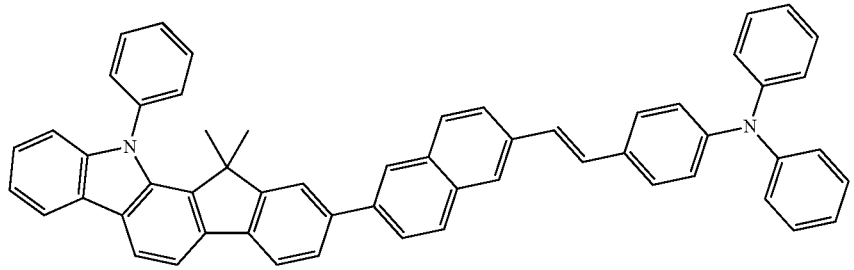
46
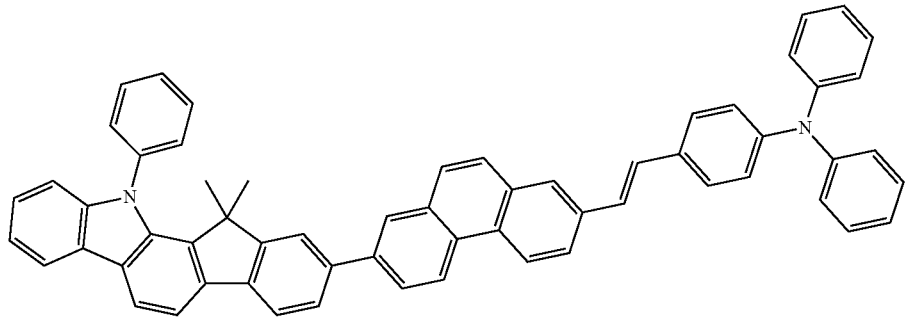
47
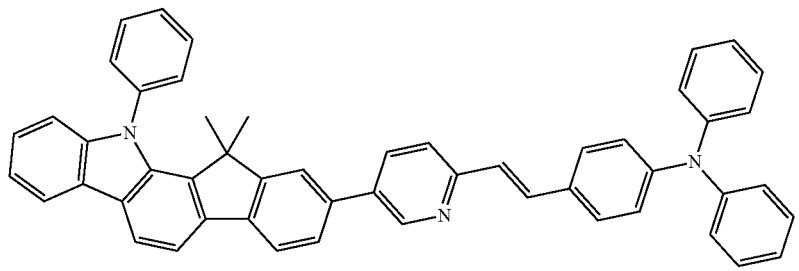

48
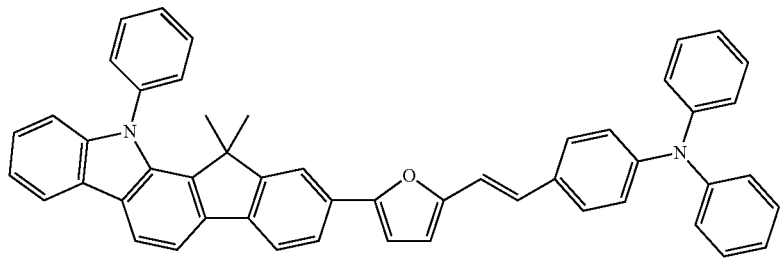
49
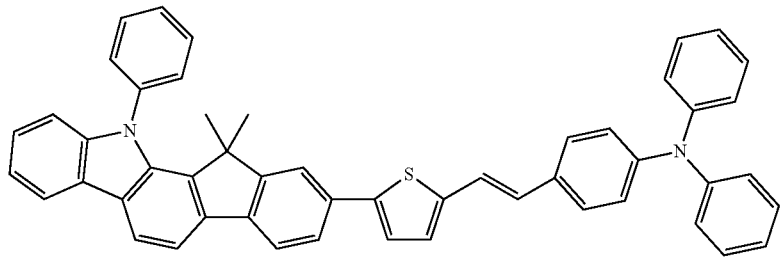
50
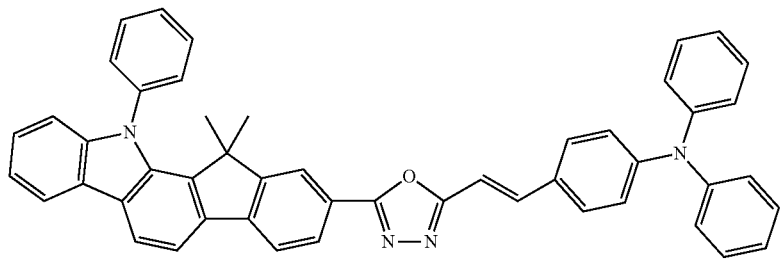
51
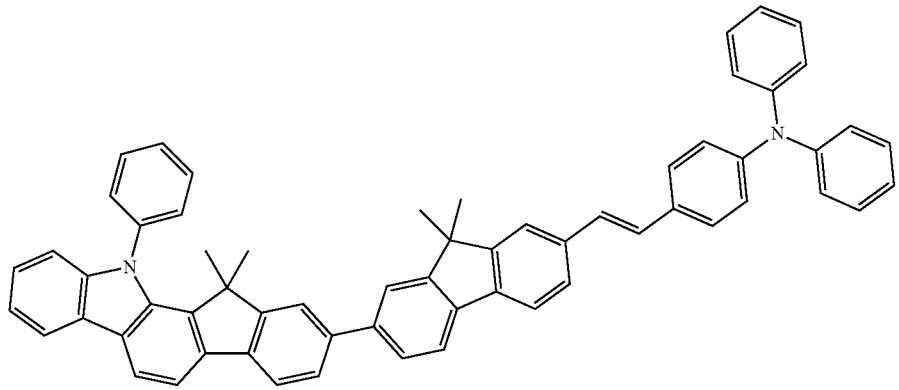
52
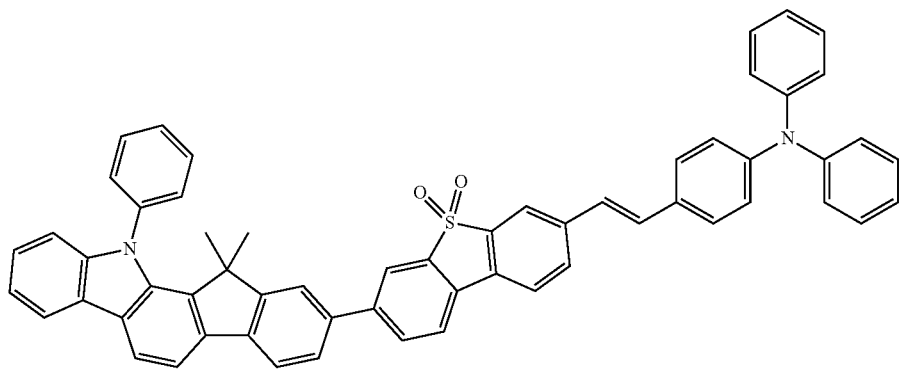

-continued
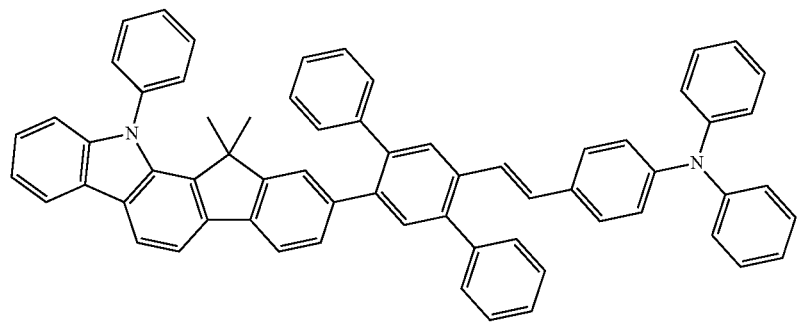
53
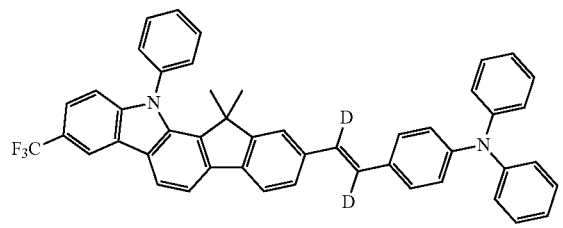
54
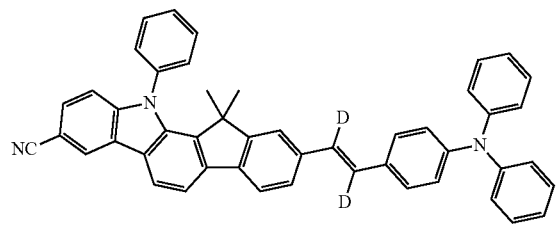
55
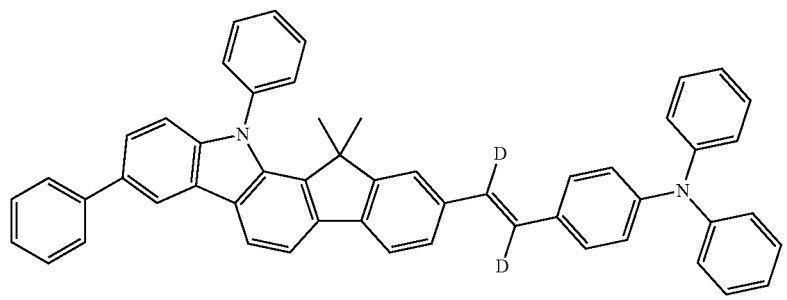
56
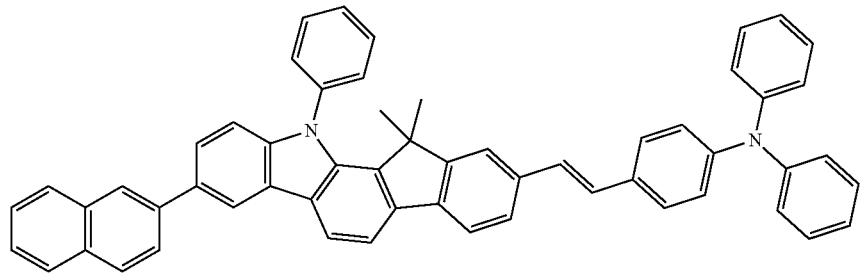
57
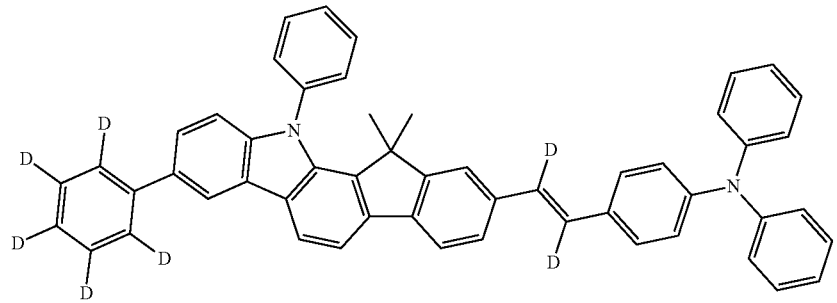
58

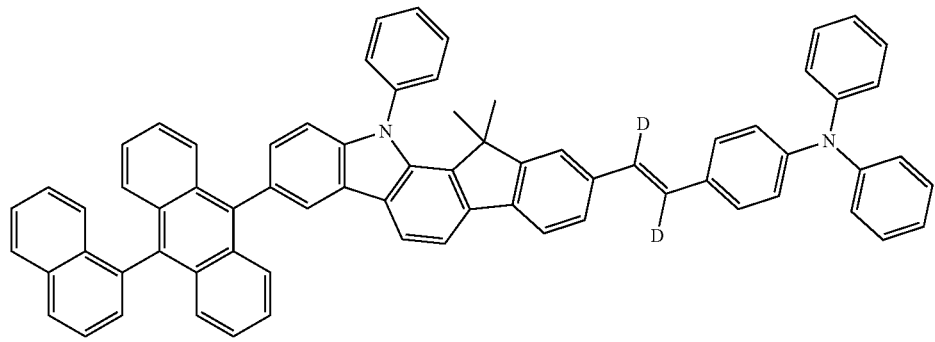
59
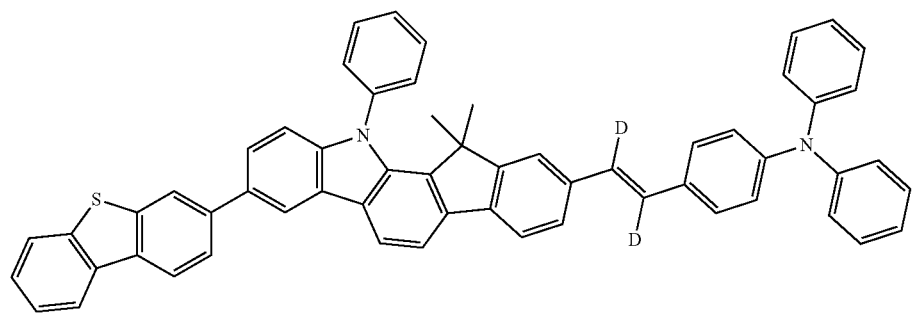
60
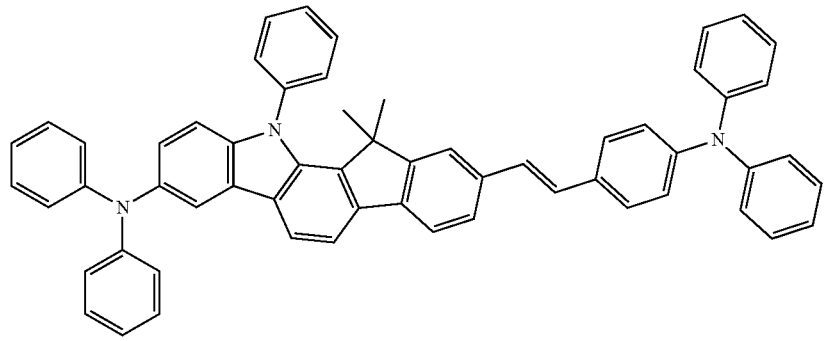
61
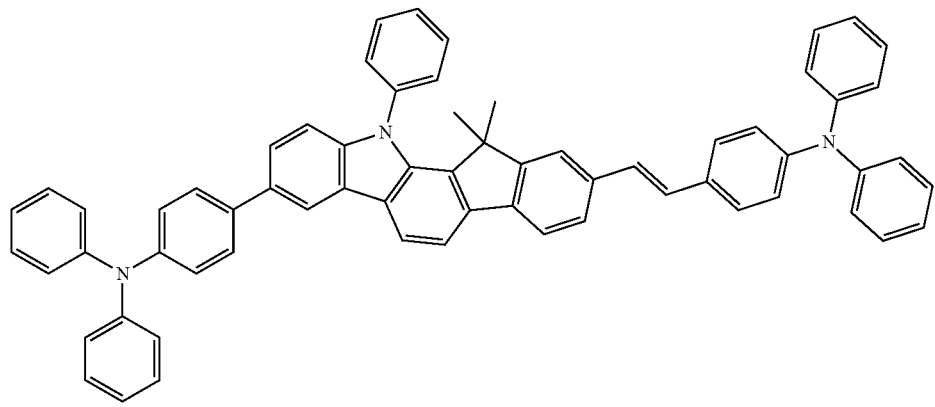
62

63
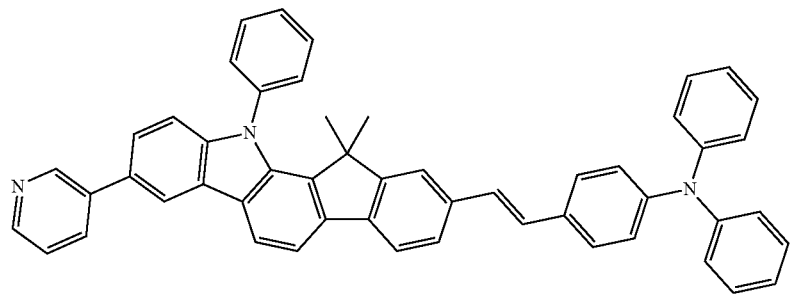
64
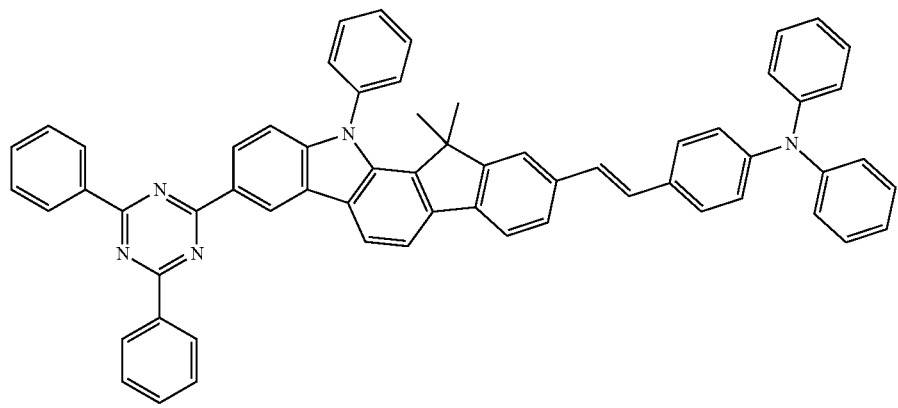
65
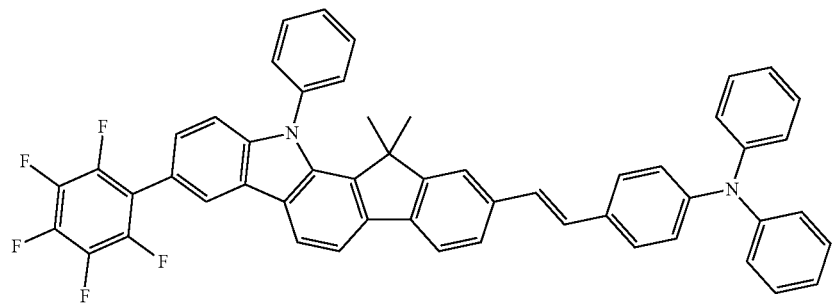
66 67
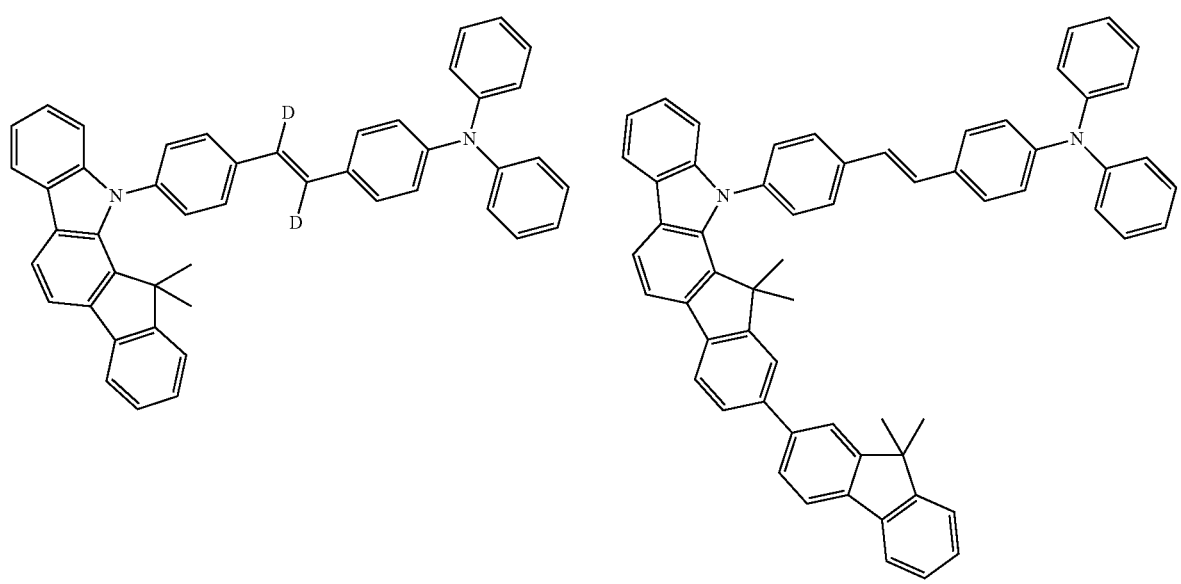

-continued
68
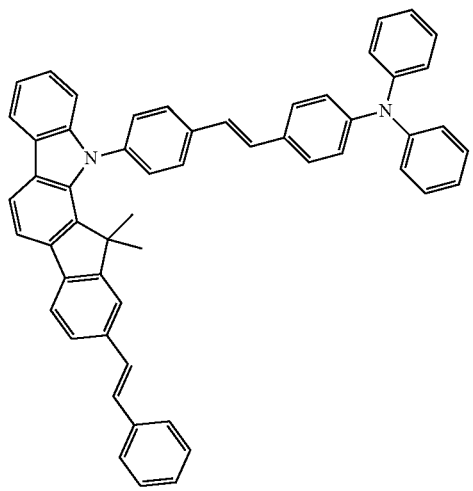
69
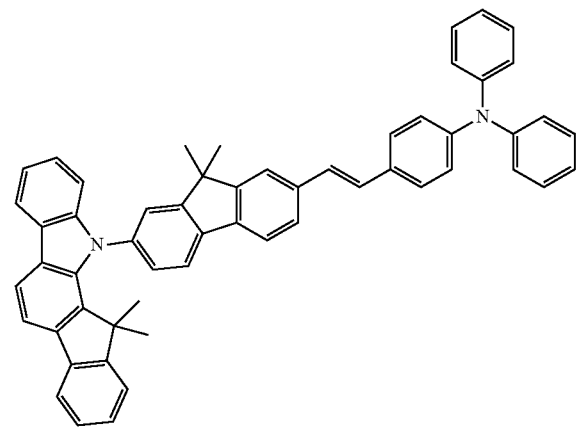
70
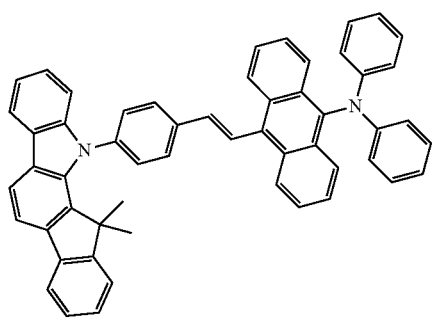
71
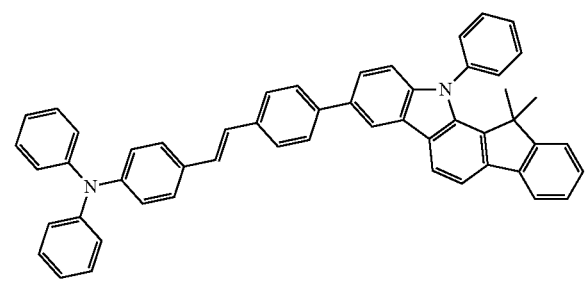
72
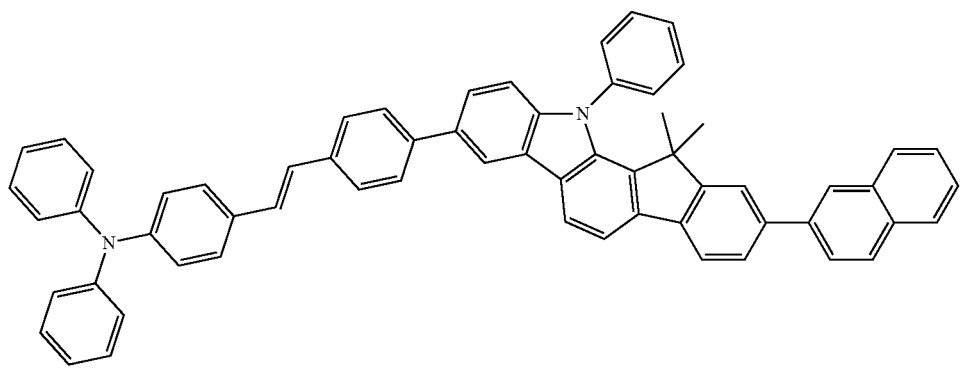
73
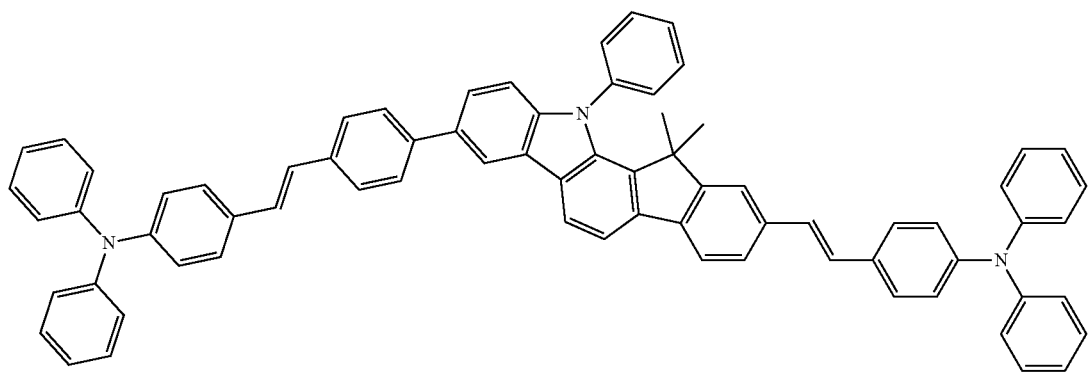

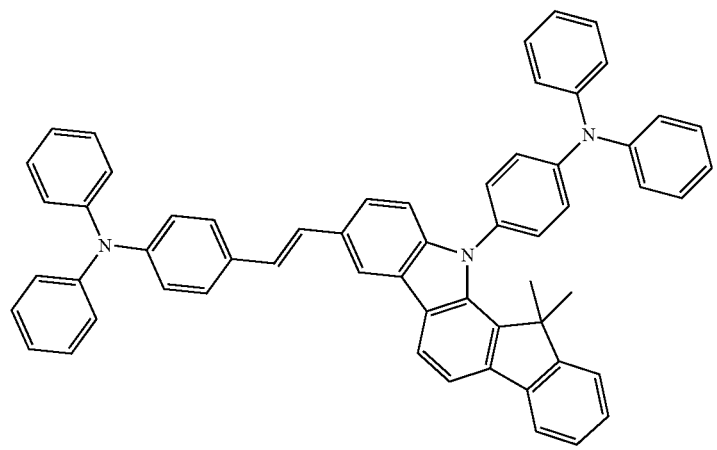

74

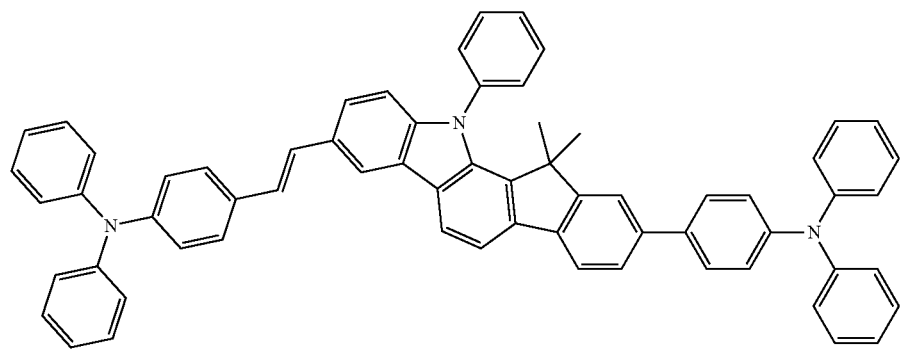

75

The heterocyclic compound of Formula 1A above may be used as an emitting material, a hole injecting material, and/or a hole transporting material of an organic light-emitting device. The heterocyclic compound of Formula 1 above, which has a heterocyclic group in the molecules thereof, has a high glass transition temperature (Tg) or a high melting point due to the inclusion of the heterocyclic group. Thus, the heterocyclic compound has high heat resistance against Joule's heat generated in an organic layer, between organic layers, or between an organic layer and a metal electrode when light emission occurs, and has high durability in high-temperature environments. When a substituent such as a fluorenyl group is introduced, the heterocyclic compound of Formula 1A above may improve morphology of the organic layer, and thus improving characteristics of an organic light-emitting device. In the compound of Formula 1A indenocarbazole moieties with fused aromatic rings possess abundant π-electrons. This is advantageous for π→π* transition, and appropriate arrangement of orbitals involved in light emission may lead to high light-emission efficiency. Double bonds are linked to indenocarbazole in a smooth resonance form, thus facilitating delocalization of π-electrons. This may also improve emission efficiency. Introduction of arylamine groups that may lead to a high light-emission efficiency via n→π* transition in the compound of Formula 1A may further improve the emission efficiency of the compound of Formula 1A.

As used herein, the term "substituted A" of the "substituted or unsubstituted A (wherein A is a certain substituent)" refers to a group A of which at least one hydrogen atom is substituted with one of a deuterium atom, a halogen atom, a hydroxyl group, a cyano group, a nitro group, an amino group, hydrazine, hydrazone, a carboxyl group or a salt derivative thereof, a sulfonic acid group or a salt derivative thereof, a phosphoric acid group or a salt derivative thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, a $C_3$-$C_{30}$ heteroaryl group, a group represented by $N(Q_{101})(Q_{102})$, and a group represented by $Si(Q_{103})(Q_{104})(Q_{105})$, wherein $Q_{101}$ to $Q_{105}$ may be each independently one of a hydrogen atom, a deuterium atom, a halogen atom, a hydroxyl group, a cyano group, an amino group, a nitro group, a carboxyl group, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{30}$ cycloalkyl group, a $C_3$-$C_{30}$ cycloalkenyl group, a $C_5$-$C_{30}$ aryl group, a $C_5$-$C_{30}$ aryloxy group, a $C_5$-$C_{30}$ arylthio group, and a $C_{20}$-$C_{30}$ heteroaryl group.

For example, the term "substituted A" may refer to a group A of which at least one hydrogen atom is substituted with one of a deuterium atom, a halogen atom, a hydroxyl group, a cyano group, a nitro group, a carboxyl group, a methyl group, an ethyl group, a propyl group, a butyl group, a pentyl group, a methoxy group, an ethoxy group, a phenyl group, a biphenyl group, a pentalenyl group, an indenyl group, a naphthyl group, an azulenyl group, a heptalenyl group, an indacenyl group, an acenaphthyl group, a fluorenyl group, a spirofluorenyl group, a phenalenyl group, a phenanthrenyl group, a phenantridinyl group, a phenanthrolinyl group, an anthryl group, a fluoranthenyl group, a triphenyllenyl group, a pyrenyl group, a chrycenyl group, a naphthacenyl group, a picenyl group, a perylenyl group, a pentaphenyl group, a hexacenyl group, a pyrrolyl group, an imidazolyl group, a benzoimidazolyl group, a pyrazolyl group, a pyridinyl group, a pyrazinyl group, a pyrimidinyl group, an imidazopyrimidinyl group, a pyridazinyl group, an indolyl group, an isoindolyl group, a pyridoindolyl group, an indazolyl group, a furinyl group, a quinolinyl group, a benzoquinolinyl group, a phthalazinyl group, a phthalazinyl group, a quinoxalinyl group, a quinazolinyl group, a carbazolyl group, a phenazinyl group, a furanyl group, a benzofuranyl group, a dibenzofuranyl group, a thiophenyl group, a benzothiophenyl group, a dibenzothiophenyl group, a thiazolyl group, an isothiazolyl group, a benzothiazolyl group, an oxazolyl group, a benzooxazolyl group, an isoxazolyl group, an oxadiazolyl group, a triazolyl group, a triazinyl group, a tetrazolyl group, a group represented by $N(Q_{101})(Q_{102})$, and a group represented by $Si(Q_{103})(Q_{104})(Q_{105})$.

As used herein, the unsubstituted $C_1$-$C_{30}$ alkyl group refers to a linear or branched saturated hydrocarbon that lacks one hydrogen atom from alkane. Non-limiting examples of the unsubstituted $C_1$-$C_{30}$ alkyl group include methyl, ethyl, propyl, isobutyl, sec-butyl, pentyl, isoamyl, and hexyl. Substituents of the substituted $C_1$-$C_{30}$ alkyl group are the same as described above in conjunction with the "substituted A".

As used herein, the unsubstituted $C_2$-$C_{30}$ alkenyl group indicates a hydrocarbon chain having at least one carbon-carbon double bond in the center or at a terminal of the unsubstituted $C_2$-$C_{30}$ alkyl group. Non-limiting examples of the unsubstituted $C_2$-$C_{30}$ alkenyl group include ethenyl, propenyl, butenyl, pentenyl, hexenyl, heptenyl, octenyl, propadienyl, isoprenyl, and allyl. Substituents of the substituted $C_2$-$C_{30}$ alkenyl group are the same as described above in conjunction with the "substituted A".

As used herein, the unsubstituted $C_2$-$C_{30}$ alkynyl group indicates a hydrocarbon chain having at least one carbon-carbon triple bond in the center or at a terminal of the unsubstituted $C_2$-$C_{60}$ alkyl group. Non-limiting examples of the unsubstituted $C_2$-$C_{30}$ alkynyl group include ethynyl, propynyl, and acetylenyl. Substituents of the substituted $C_2$-$C_{30}$ alkynyl group are the same as described above in conjunction with the "substituted A".

As used herein, the unsubstituted $C_1$-$C_{30}$ alkoxy group refers to a group represented by —OY, wherein Y is an unsubstituted $C_1$-$C_{30}$ alkyl group as described above. Non-limiting examples of the unsubstituted $C_1$-$C_{30}$ alkoxy group are a methoxy group, an ethoxy group, an isopropyloxy group, a butoxy group, and a pentoxy group. Substituents of the substituted $C_1$-$C_{30}$ alkoxy group are the same as described above in conjunction with the "substituted A".

As used herein, the unsubstituted $C_3$-$C_{30}$ cycloalkyl group indicates a cyclic saturated hydrocarbon group. Non-limiting examples of the unsubstituted $C_3$-$C_{30}$ cycloalkyl group are cyclopropyl, cyclobutyl, cyclopentyl, cyclohexyl, and cyclooctyl. Substituents of the substituted $C_3$-$C_{30}$ cycloalkyl group are the same as described above in conjunction with the "substituted A".

As used herein, the unsubstituted $C_3$-$C_{30}$ cycloalkenyl group refers to a non-aromatic, cyclic unsaturated hydrocarbon group with at least one carbon-carbon double bond. Non-limiting examples of the unsubstituted $C_3$-$C_{30}$ cycloalkenyl group are cyclopropenyl, cyclobutenyl, cyclopentenyl, cyclohexenyl, cycloheptenyl, 1,3-cyclohexadienyl, 1,4-cyclohexadienyl, 2,4-cycloheptadienyl, and 1,5-cyclooctadienyloctenyl. Substituents of the substituted $C_3$-$C_{60}$ cycloalkenyl group are the same as described above in conjunction with the "substituted A".

As used herein, the unsubstituted $C_5$-$C_{30}$ aryl group indicates a monovalent group including a $C_5$-$C_{30}$ carbocyclic aromatic system, which may be monocyclic or polycyclic. In a polycyclic group, at least two rings may be fused to each other. Non-limiting examples of the unsubstituted $C_5$-$C_{30}$ aryl group are phenyl, pentalenyl, indenyl, naphthyl, azulenyl, heptalenyl, indacenyl, acenaphthyl, fluorenyl, spiro-fluorenyl, phenalenyl, phenanthrenyl, anthryl, fluoranthenyl, triphenylenyl, pyrenyl, chrysenyl, naphthacenyl, picenyl, perylenyl, pentaphenyl, and hexacenyl. Substituents of the substituted $C_5$-$C_{30}$ aryl group are the same as described above in conjunction with the "substituted A".

As used herein, the unsubstituted $C_5$-$C_{30}$ aryloxy group refers to a monovalent group with a carbon atom of the $C_5$-$C_{30}$ aryl group attached via an oxygen linker (—O—). Substituents of the substituted $C_5$-$C_{30}$ aryloxy group are the same as described above in conjunction with the "substituted A".

As used herein, the unsubstituted $C_5$-$C_{30}$ arylthio group refers to a monovalent group with a carbon atom of the $C_5$-$C_{30}$ aryl group attached via a sulfur linker (—S—). Non-limiting examples of the unsubstituted $C_5$-$C_{30}$ arylthio group are a phenylthio group, a naphthylthio group, an indanylthio group, and an indenylthio group. Substitutes of the substituted $C_5$-$C_{30}$ arylthio group are the same as described above in conjunction with the "substituted A".

As used herein, the unsubstituted $C_3$-$C_{30}$ heteroaryl group indicates a monovalent group with at least one ring including at least one heteroatom selected from among N, O, P, and S, which may be a monocyclic or polycyclic group. In a polycyclic group, at least two rings may be fused to each other. Non-limiting examples of the unsubstituted $C_3$-$C_{30}$ heteroaryl group are pyrrolyl, imidazolyl, pyrazolyl, pyridinyl, pyrazinyl, pyrimidinyl, pyridazinyl, isoindolyl, indolyl, indazolyl, purinyl, quinolinyl, benzoquinolinyl, phthalazinyl, naphthyridinyl, quinoxalinyl, quinazolinyl, cinnolinyl, carbazolyl, phenanthridinyl, acridinyl, phenanthrolinyl, phenazinyl, benzooxazolyl, benzoimidazolyl, furanyl, benzofuranyl, thiophenyl, benzothiophenyl, thiazolyl, isothiazolyl, benzothiazolyl, isoxazolyl, oxazolyl, triazolyl, tetrazolyl, oxadiazolyl, triazinyl, and benzooxazolyl. Substituents of the substituted $C_3$-$C_{30}$ heteroaryl group are the same as described above in conjunction with the "substituted A".

In the specification, the unsubstituted $C_1$-$C_{30}$ alkylene group refers to a linear or branched divalent group that lacks two hydrogen atoms from the unsubstituted $C_1$-$C_{30}$ alkylene group. Examples of the unsubstituted $C_1$-$C_{30}$ alkylene group may be inferred based on those of the unsubstituted $C_1$-$C_{30}$ alkyl group described above. Substituents of the substituted $C_1$-$C_{30}$ alkylene group are the same as those described above in conjunction with the "substituted A".

As used herein, the unsubstituted $C_5$-$C_{30}$ arylene group indicates a divalent group including a $C_5$-$C_{30}$ carbocyclic aromatic system, which may be monocyclic or polycyclic. Examples of the unsubstituted $C_5$-$C_{30}$ arylene group may be inferred based on those of the unsubstituted $C_5$-$C_{30}$ alkyl group described above. Substituents of the substituted $C_5$-$C_{30}$ arylene group are the same as those described above in conjunction with the "substituted A".

The heterocyclic compound of Formula 1A may be synthesized using a known organic synthesis method. A synthesis method of the heterocyclic compound of Formula 1A may be understood by one of ordinary skill in the art from the examples that will be described below.

The heterocyclic compound of Formula 1A above may be used in an organic light-emitting device.

According to another aspect of the present invention, an organic light-emitting device includes: a first electrode; a second electrode disposed opposite to the first electrode; and an organic layer disposed between the first electrode and the second electrode. The organic layer, including at least one layer, may contain at least one of the heterocyclic compounds of Formula 1A described above.

As used herein, the term "organic layer" refers to a layer containing an organic compound and including at least one layer. For example, the organic layer may include at least one layer selected from among a hole injection layer, a hole transport layer, a hole injection and transport layer having both hole injection and hole transport capabilities, an electron blocking layer, an emission layer, a hole blocking layer, an electron injection layer, an electron transport layer, and an electron injection and transport layer having both electron injection and electron transport capabilities. The organic layer may further include an inorganic compound or an inorganic material such as an organometallic complex. In one embodiment, the organic layer may include both an organic compound and an inorganic compound or may include one layer including an organic compound and another layer including an inorganic compound or material. For example, the organic layer may include both an organic compound and an organometallic complex in one layer. In another embodiment, the organic layer may include a layer containing an organic compound and a layer containing an inorganic compound or an inorganic material.

At least one of the heterocyclic compounds listed above may be included in one layer of the organic layer, and in some other embodiments, at least one of the heterocyclic compounds listed above may be included in different layers of the organic layer. For example, the organic layer may include one of the heterocyclic compounds as an emitting dopant in an emission layer, and another heterocyclic compound as a hole transport material in a hole transport layer. In another embodiment, the organic layer may include one of the heterocyclic compounds as an emitting dopant and another heterocyclic compound as an emitting host in an emission layer. In another embodiment, the organic layer may include one of the heterocyclic compounds as an emitting dopant and another heterocyclic compound as an emitting host in an emission layer, and still another heterocyclic compound as a hole transport material in a hole transport layer.

The organic layer may include at least one of an emission layer, a hole injection layer, a hole transport layer, and a hole injection and transport layer having both hole injection and hole transport capabilities, and at least one of the emission layer, the hole injection layer, the hole transport layer, and the hole injection and transport layer may include the heterocyclic compound.

In some embodiments, the organic light-emitting device may have a first electrode/hole injection layer/hole transport layer/emission layer/electron transport layer/second electrode structure, wherein the emission layer, the hole transport layer, or the hole injection layer may include the heterocyclic compound. In some embodiments, at least two of the emission layer, the hole transport layer, and the hole injection layer may include the heterocyclic compound. In these embodiments, each of the at least two layers may include a different heterocyclic compound. As described above, a layer of the organic layer may include a mixture of at least two of the heterocyclic compounds listed above, or a mixture of one of the heterocyclic compounds and a non-heterocyclic compound.

In some embodiments, the organic layer may include an emission layer, which may include a host and a dopant, and the heterocyclic compound may be a fluorescent host, a phosphorescent host, or a fluorescent dopant of the emission layer.

In some embodiments, the organic layer may include an emission layer, which may further include an anthracene compound, an arylamine compound, or a styryl compound. The emission layer may or may not include the heterocyclic compound.

The organic layer may include an emission layer, which may include a host and a dopant. The emission layer may further include a phosphorescent dopant. For example, the phosphorescent dopant may be, but is not limited to, an organometallic complex including at least one of iridium (Ir), platinum (Pt), osmium (Os), rhenium (Re), titanium (Ti), zirconium (Zr), hafnium (Hf), and a combination of at least two thereof. The emission layer may or may not include the heterocyclic compound.

At least one of the hole injection layer, the hole transport layer, and the hole injection and transport layer may further include a charge generating material, in addition to the heterocyclic compound. The charge generating material may be, for example, a p-dopant. The hole injection layer, the hole transport layer, and the hole injection and transport layer may or may not include the heterocyclic compound.

The organic layer may further include an electron transport layer, which may include an electron transporting organic compound and a metal-containing material. The metal-containing material may include a lithium (Li) complex. The electron transport layer may or may not include the heterocyclic compound.

At least one organic layer disposed between the first electrode and the second electrode may be formed using deposition or a wet process.

As used herein, the terms "wet process" refers to a process involving applying a mixture of a specific material and a solvent to a predetermined substrate, and drying and/or thermally treating to remove at least part of the solvent, thereby forming a layer including the specific material on the substrate.

For example, the organic layer may be formed using a general vacuum deposition method. In some other embodiments, the organic layer may be formed by applying the mixture of the heterocyclic compound and the solvent to a region to form the organic layer (for example, on the hole transport layer) using spin coating, spraying, inkjet printing, dipping, casting, gravure coating, bar coating, roll coating, wire bar boating, screen coating, flexo coating, offset coating, laser transferring, or the like, and drying and/or thermally treating the mixture coating the region to form the organic layer to remove at least part of the solvent.

In another embodiment, the organic layer may be formed using a laser transfer method by which an organic layer is formed on a base film using vacuum deposition or a wet process described above, and then transferred to a region to form the organic layer of an organic light-emitting device (for example, on the hole transport layer of the organic light-emitting device) using laser.

FIG. 1 is a schematic sectional view of an organic light-emitting device 10 according to an embodiment of the present invention. Hereinafter, a structure of an organic light-emitting device according to an embodiment of the present invention and a method of manufacturing the same will now be described with reference to FIG. 1.

Referring to FIG. 1, the organic light-emitting device 10 according to the present embodiment includes a first electrode 13, an organic layer 15, and a second electrode 17, which are sequentially stacked on a substrate 11 in this order.

The substrate 11 may be any substrate that is used in conventional organic light-emitting devices. In some embodiments the substrate 11 may be a glass substrate or a transparent plastic substrate with strong mechanical strength, thermal stability, transparency, surface smoothness, ease of handling, and water resistance.

The first electrode 13 may be formed by depositing or sputtering a first electrode-forming material on the substrate 11. When the first electrode 13 constitutes an anode, a material having a high work function may be used as the first electrode-forming material to facilitate hole injection. The first electrode 13 may be a reflective electrode or a transmission electrode. Suitable first electrode-forming materials are transparent and conductive materials such as ITO, IZO, $SnO_2$, and ZnO. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The organic layer 15 may be disposed on the first electrode 13. As described above, the organic layer 15 indicates any layer interposed between the first electrode 13 and the second electrode 17. The organic layer 15 may further include an inorganic compound or material such as a metal complex.

The organic layer 15 may include a hole injection layer (HIL), a hole transport layer (HTL), an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using a wet process such as spin coating, the coating conditions may vary according to the compound that is used to form the HIL, and the desired structure and thermal properties of the HIL to be formed. For example, the coating rate may be from about 2,000 rpm to about 5,000 rpm, and a temperature at which heat treatment is performed to remove a solvent after coating may be from about 80° C. to about 200° C. However, the coating conditions are not limited thereto.

For example, as a HIL material, the heterocyclic compound of Formula 1A or any known hole injection materials may be used. Non-limiting examples of known hole injection materials include N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4"-tris(3-methylphenylphenylamino)triphenylamine (m-MTDATA), N,N'-di(1-naphthyl)-N,N'-diphenylbenzidine (NPB), 4,4'4"-Tris(N,N-diphenylamino)triphenylamine (TDATA), 4,4',4'-tris {N,-(2-naphthyl)-N-phenylamino}-triphenylamine (2T-NATA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), and polyaniline)/poly(4-styrenesulfonate (PANI/PSS).

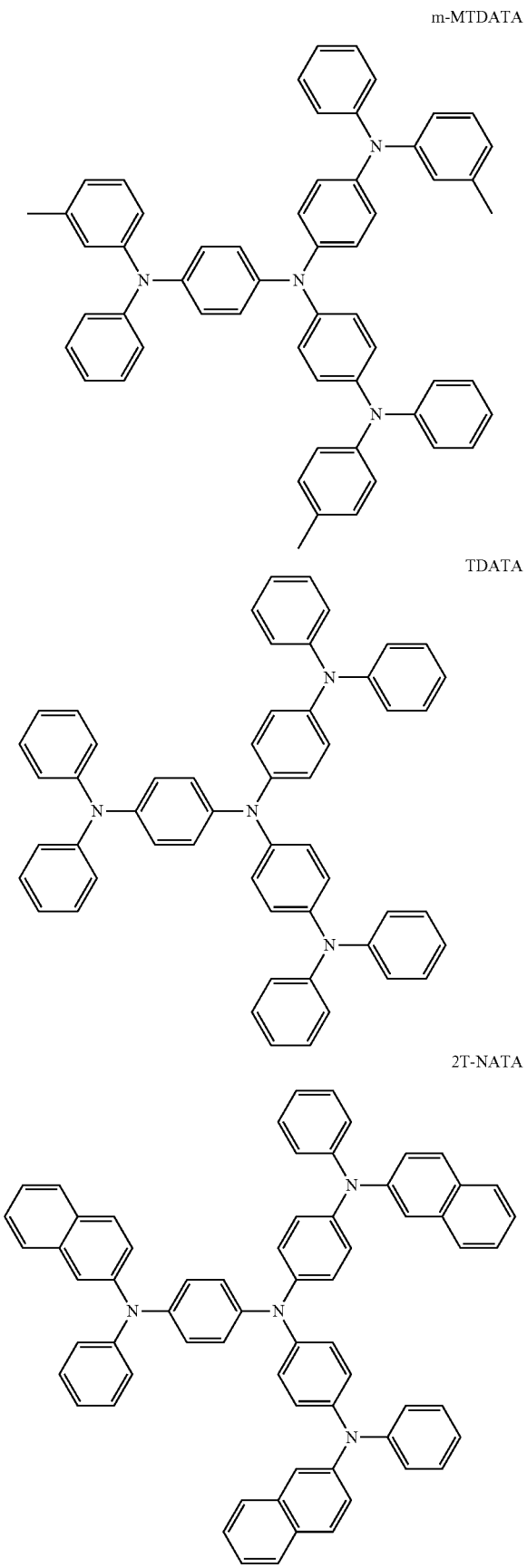

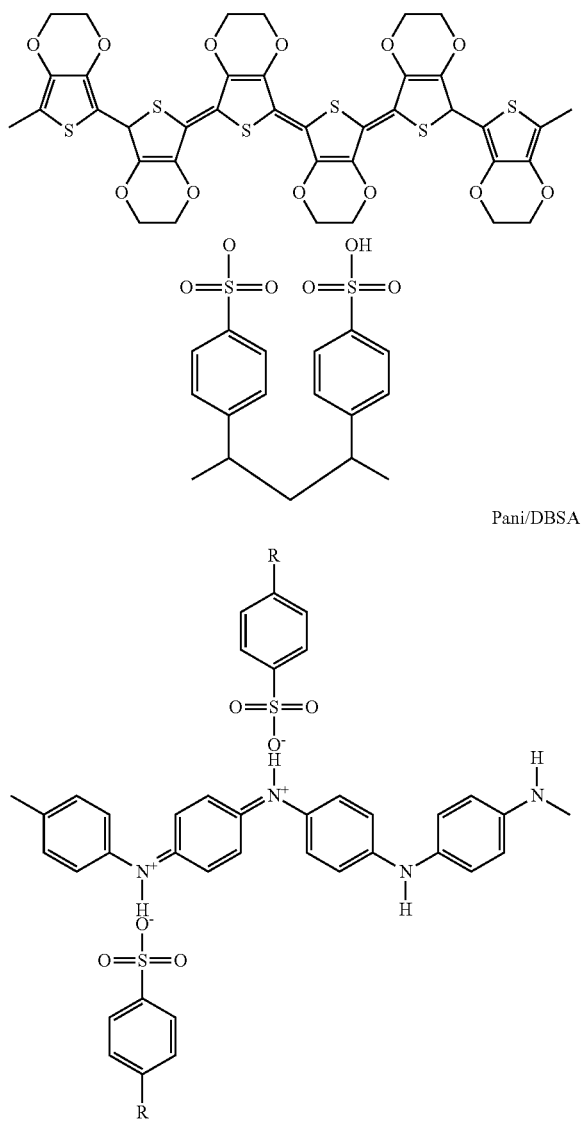

PEDOT/PSS

Pani/DBSA

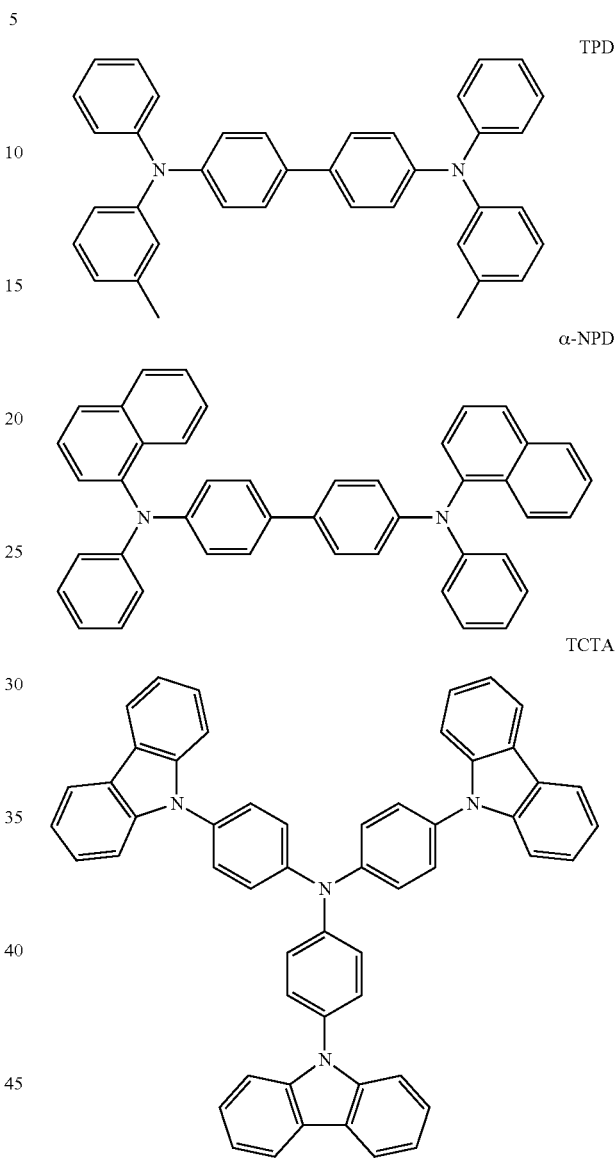

TPD

α-NPD

TCTA densed ring, such as α-NPD (4,4'-bis[N-(1-naphthyl)-N-phenylamino]biphenyl, TCTA (4,4',4''-tris(N-carbazolyl) triphenylamine), and the like.

The thickness of the HIL may be about 100 Å to about 10,000 Å, and in some embodiments, may be about 100 Å to about 1,000 Å. When the thickness of the HIL is within these ranges, the HIL may have improved hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

As a HTL material, the heterocyclic compound of Formula 1A or any known hole transporting materials may be used. Examples of known hole transporting materials include carbazole derivatives such as N-phenylcarbazole, polyvinylcarbazole, and the like; triphenylamine materials such as TPD (N,N'-bis(3-methylphenyl)-N,N'-diphenyl-[1,1-biphenyl]-4, 4'-diamine); and amine derivatives having an aromatic con- The thickness of the HTL may be about 50 Å to about 1,000 Å, and in some embodiments, may be about 100 Å to about 800 Å. When the thickness of the HTL is within these ranges, the HTL may have improved hole transporting ability without a substantial increase in driving voltage.

In some embodiments, instead of the HIL and the HTL, a hole injection and transport layer having both hole injection and hole transport capabilities may be formed. As a material for the hole injection and transport layer, the heterocyclic compound of Formula 1 or Formula 2, or any known materials may be used.

At least one of the hole injection layer, the hole transport layer, and the hole injection and transport layer may further include a charge generating material for improved layer conductivity, in addition to a known hole injection material and a known hole transport material.

The charge generating material may be, for example, a p-dopant. Non-limiting examples of the p-dopant include quinone derivatives such as tetracyanoquinonedimethane (TCNQ), 2,3,5,6-tetrafluoro-tetracyano-1,4-benzoquinonedimethane (F4TCNQ), and the like; metal oxides such as tungsten oxide, molybdenum oxide, and the like; and cyano-containing compounds such as Compound 100 below.

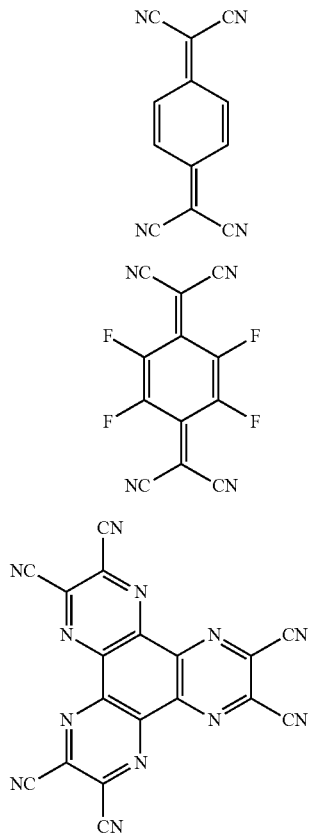

When the hole injection layer, the hole transport layer, or the hole injection and transport layer having both hole injection and hole transport capabilities further includes a charge generating material, the charge generating material may be, but is not limited to, homogeneous dispersed or inhomogeneously distributed in the layer.

Then, an EML may be formed on the HTL or the hole injection and transport layer having both hole injection and hole transport capabilities by using vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

As an EML material, at least one of the heterocyclic compound of Formula 1A, and known light-emitting materials (including hosts and dopants) may be used. When including the heterocyclic compound of Formula 1A, the EML may further include a known phosphorescent host, fluorescent host, phosphorescent dopant, or fluorescent dopant. The heterocyclic compound may also serve as a phosphorescent host, a fluorescent host, or a fluorescent dopant.

The heterocyclic compound of Formula 1A may be used as a host. In another embodiment a known dopant may be used. Non-limiting examples of known hosts include Alq3, CBP (4,4'-N,N'-dicabazole-biphenyl), PVK (poly(n-vinylcabazole), ADN (9,10-di(naphthalene-2-yl)anthracene), TCTA, TPBI ((1,3,5-tris(N-phenylbenzimidazole-2-yl)benzene), TBADN ((3-tert-butyl-9,10-di(naphth-2-yl)anthracene), DSA (distyrylarylene), and E3.

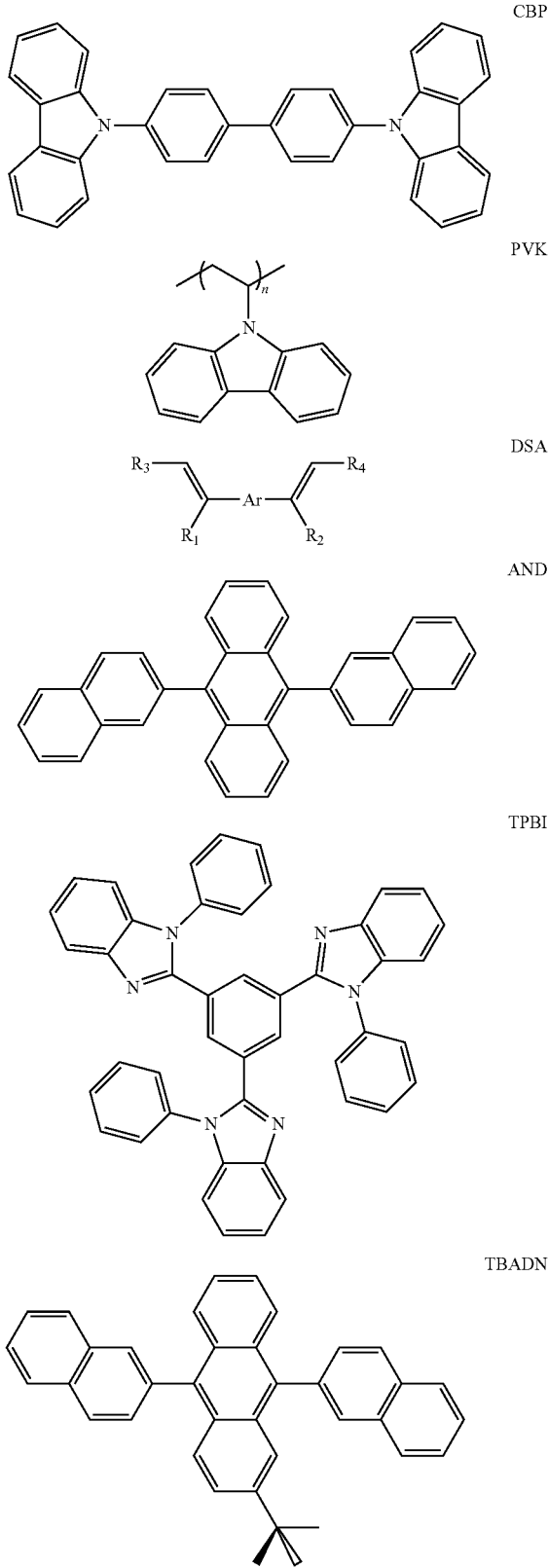

-continued

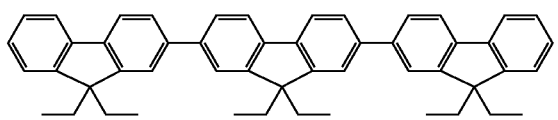
E3

The heterocyclic compound of Formula 1A may be used as a dopant. In another embodiment a known dopant may be used. For example, at least one of a fluorescent dopant and a phosphorescent dopant may be used. For example, the phosphorescent dopant may include, but is not limited to, an organometallic complex including at least one selected from the group consisting of iridium (Ir), platinum (Pt), osmium (Os), rhenium (Re), titanium (Ti), zirconium (Zr), hafnium (Hf), and a combination of at least two thereof.

Non-limiting examples of known red dopants include PtOEP (Pt(II) octaethylporphine), Ir(piq)$_3$ (tris(2-phenylisoquinoline)iridium), and Btp$_2$Ir(acac) (bis(2-(2'-benzothienyl)-pyridinato-N,C3')iridium(acetylacetonate)).

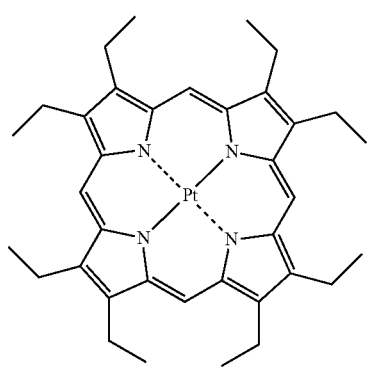

PtOEP

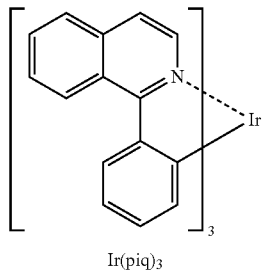

Ir(piq)$_3$

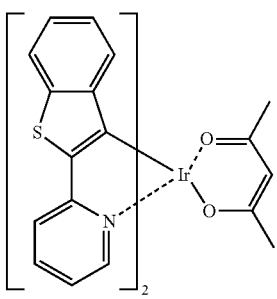

Btp$_2$Ir(acac)

Non-limiting examples of known green dopants include Ir(ppy)$_3$ (tris(2-phenylpyridine) iridium), Ir(ppy)$_2$(acac) (bis (2-phenylpyridine)(acetylacetonato)iridium(III), Ir(mppy)$_3$ (tris(2-(4-tolyl)phenylpiridine)iridium), and C545T (10-(2-benzothiazolyl)-1,1,7,7-tetramethyl-2,3,6,7-tetrahydro-1H, 5H,11H-[1]benzopyrano[6,7,8-ij]-quinolizin-11-one).

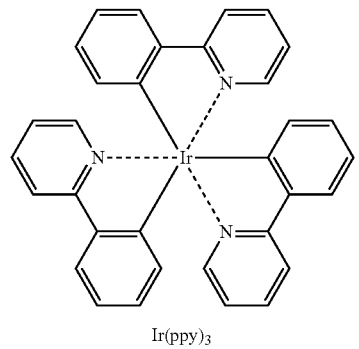

Ir(ppy)$_3$

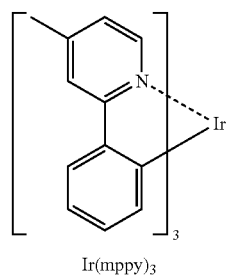

Ir(mppy)$_3$

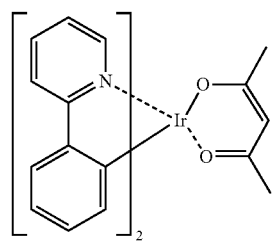

Ir(ppy)$_2$(acac)

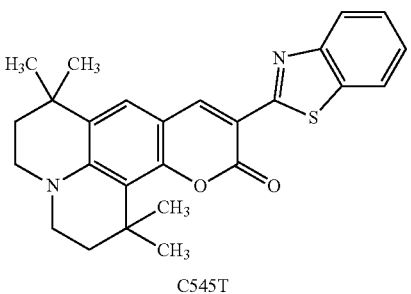

C545T

Non-limiting examples of known blue dopants include F$_2$Irpic (bis[3,5-difluoro-2-(2-pyridyl)phenyl](picolinato) iridium(III)), (F$_2$ ppy)$_2$Ir(tmd), Ir(dfppz)$_3$, DPVBi (4,4'-bis (2,2'-diphenylethen-1-yl)biphenyl), DPAVBi (4,4'-bis[4-(diphenylamino)styryl]biphenyl), and TBPe (2,5,8,11-tetratert-butyl perylene).

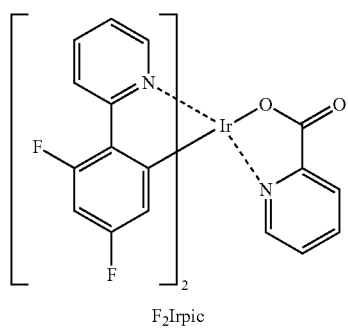
F₂Irpic

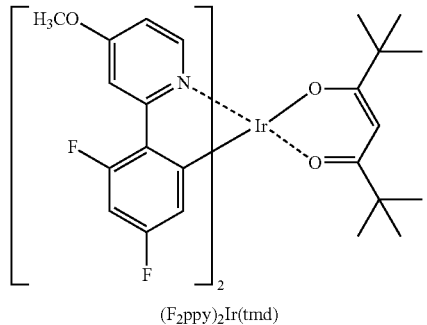
(F₂ppy)₂Ir(tmd)

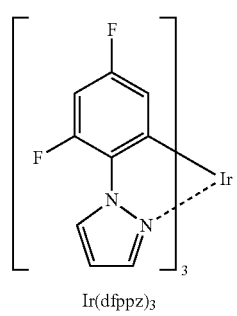
Ir(dfppz)₃

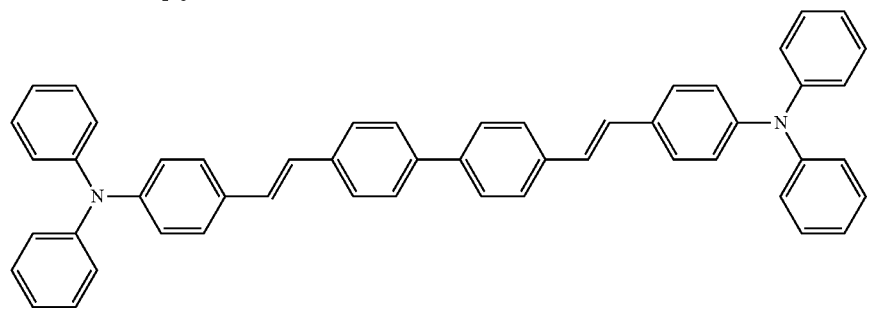
DPAVBi

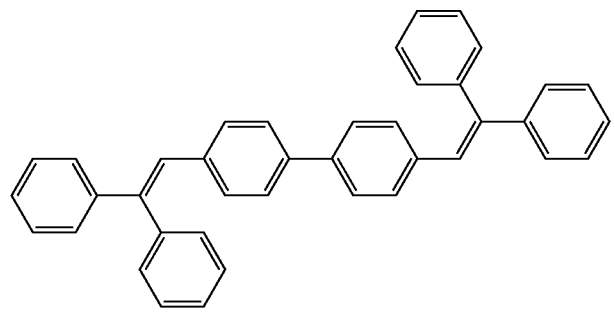
DPVBi

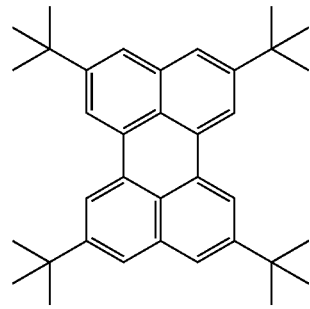
TBPe

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1,000 Å, and in some embodiments, may be from about 200 Å to about 600 Å. When the thickness of the EML is within these ranges, the EML may have improved light emitting ability without a substantial increase in driving voltage.

When a phosphorescent dopant is also used to form the EML, a HBL may be formed between the ETL and the EML by using vacuum deposition, spin coating, casting, Langmuir-Blodgett (LB) deposition, or the like, in order to prevent diffusion of triplet excitons or holes into an ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials include an oxadiazole derivative, a triazole derivative, and a phenanthroline derivative. For example, BCP may be used as a material for forming the HBL.

The thickness of the HBL may be from about 50 Å to about 1,000 Å, and in some embodiments, may be from about 100 Å to about 300 Å. When the thickness of the HBL is within these ranges, the HBL may have improved hole blocking ability without a substantial increase in driving voltage.

Then, an ETL may be formed on the HBL or EML by vacuum deposition, spin coating, casting, or the like. When the ETL is formed using vacuum deposition or spin coating, the deposition and coating conditions may be similar to those for the formation of the HIL, though the deposition and coating conditions may vary according to the material that is used to form the ETL.

The ETL may be formed of any known hole transporting material. Non-limiting examples of known ETL materials include quinoline derivatives, and in particular, Alq3 (tris(8-quinolinolate)aluminum), BCP (2,9-dimethyl-4,7-diphenyl-1,10-phenanthroline), Bphen (4,7-diphenyl-1,10-phenanthroline; 4,7-diphenyl-1,10-phenanthroline), TAZ (3-(4-biphenylyl)-4-phenyl-5-tert-butylphenyl-1,2,4-triazole), NTAZ (4-(Naphthalen-1-yl)-3,5-diphenyl-4H-1,2,4-triazole), tBu-PBD (2-(4-biphenylyl)-5-(4-tert-butylphenyl)-1,3,4-oxadiazole, BAlq (see the following formula), Bebq₂ (beryllium bis(benzoquinolin-10-olate), AND (9,10-di(naphthalene-2-yl)anthrascene), Compound 101, and Compound 102.

BAlq

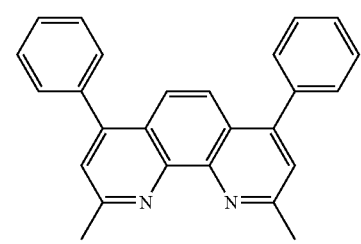

BCP

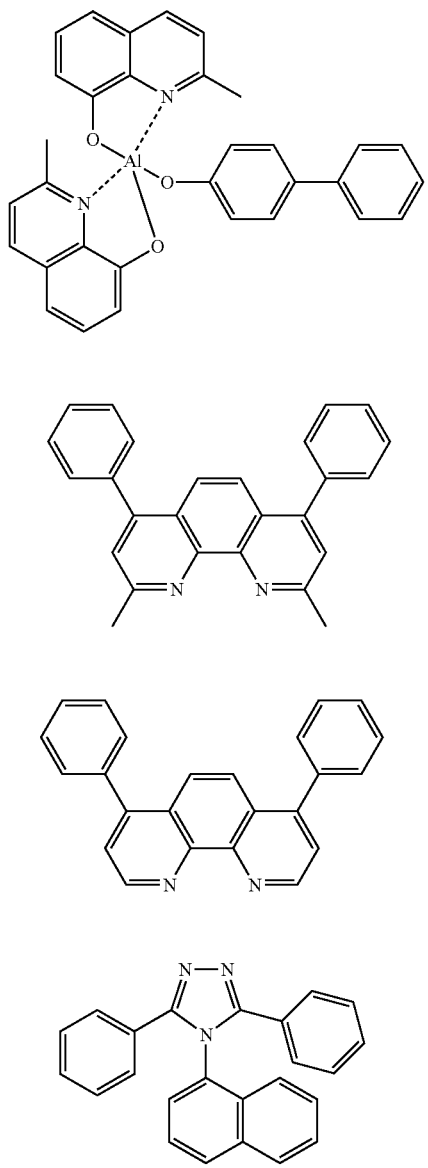

NTAZ

Bphen

TAZ tBu-PBD

Compound 101

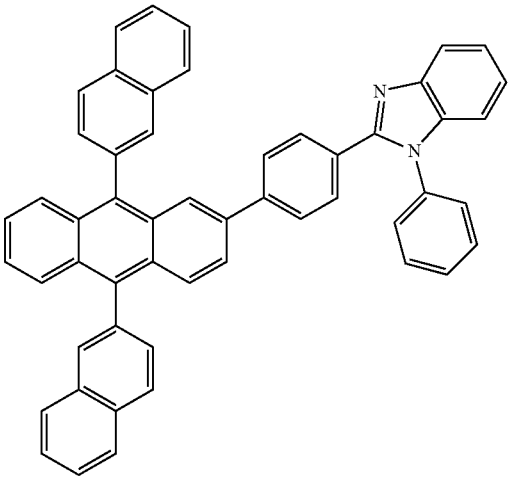

Compound 102

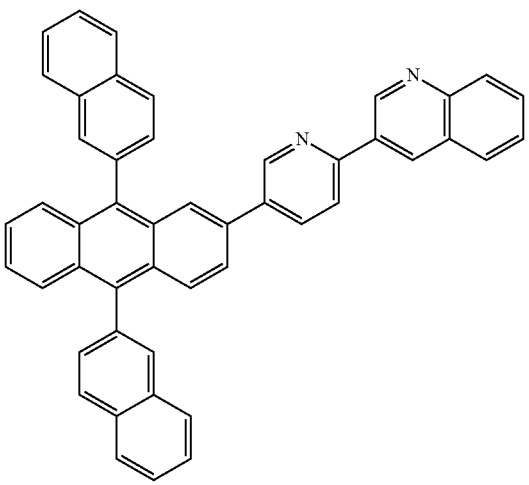

The thickness of the ETL may be from about 100 Å to about 1,000 Å, and in some other embodiments, may be from about 150 Å to about 500 Å. When the thickness of the ETL is within these ranges, the ETL may have satisfactory electron transporting ability without a substantial increase in driving voltage.

In some embodiments the ETL may include an electron-transporting organic compound and a metal-containing material. The metal-containing material may include a lithium (Li) complex. Non-limiting examples of the Li complex include lithium quinolate (LiQ) and Compound 103 below:

Compound 103

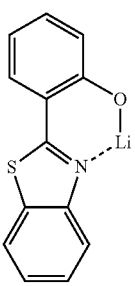

Then, an EIL, which facilitates injection of electrons from the cathode, may be formed on the ETL. Any suitable electron-injecting material may be used to form the EIL.

Examples of materials for forming the EIL include LiF, NaCl, CsF, Li$_2$O, and BaO, which are known in the art. The deposition and coating conditions for forming the EIL may be similar to those for the formation of the HIL, though the deposition and coating conditions may vary according to the material that is used to form the EIL.

The thickness of the EIL may be about 1 Å to about 100 Å, and in some embodiments, may be from about 3 Å to about 90 Å. When the thickness of the EIL is within these ranges, the EIL may have satisfactory electron injection ability without a substantial increase in driving voltage.

The second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In this regard, the second electrode 17 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. To manufacture a top-emission light-emitting device, the transmission electrode may be formed of indium tin oxide (ITO) or indium zinc oxide (IZO).

Hereinafter, the present invention will be described in detail with reference to the following synthesis examples and other examples. However, these examples are for illustrative purposes only and are not intended to limit the scope of the present invention.

Synthesis Example 1

Synthesis of Compound 8

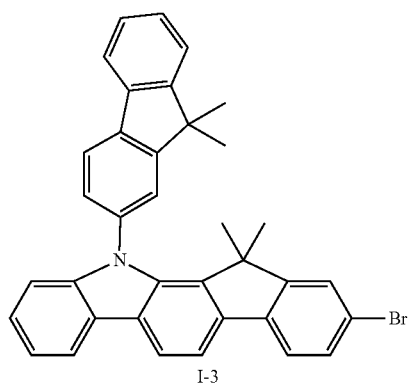

I-3

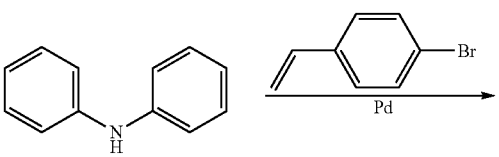

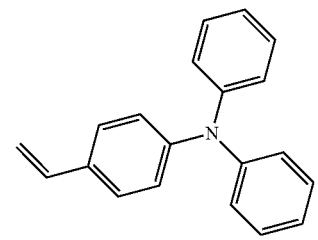

I-4

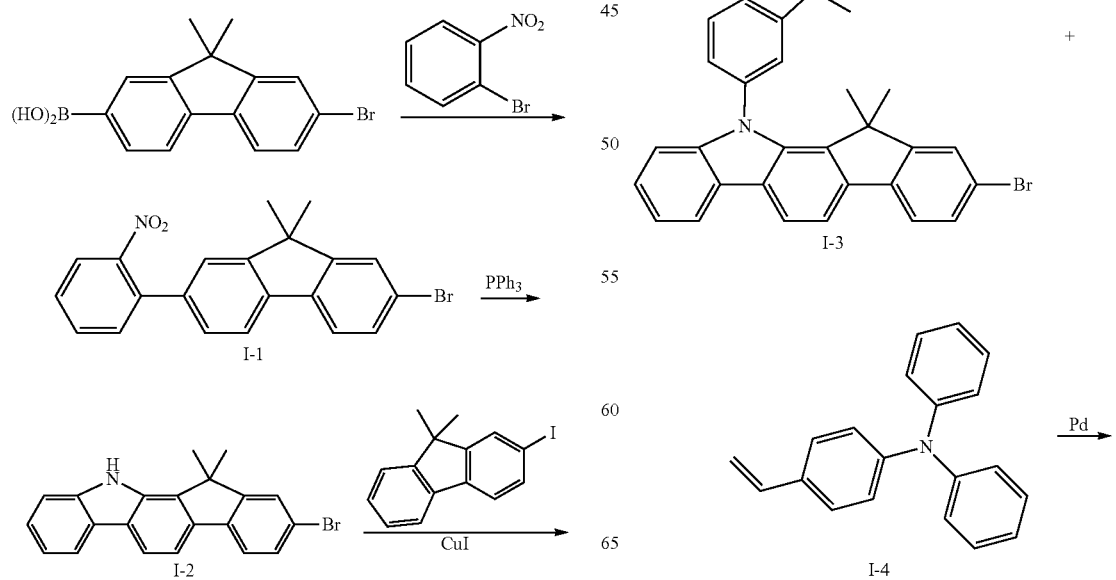

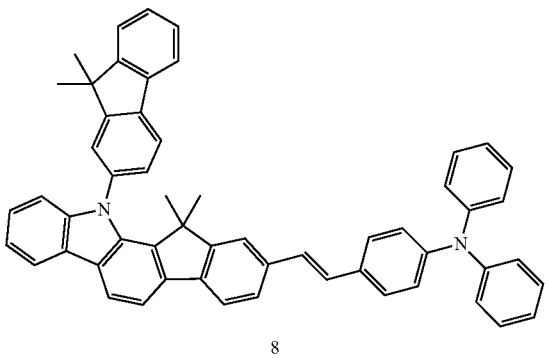

8

Synthesis of Intermediate I-1

6.34 g (20.0 mmol) of 2-bromo-9,9-dimethyl-7-fluoreneboronic acid, 4.04 g (20.0 mmol) of 2-bromonitrobenzene, 1.15 g (1.0 mmol) of Pd(PPh$_3$)-4(tetrakis(triphenylphosphine)palladium), and 8.29 g (60.0 mmol) of K$_2$CO$_3$ were dissolved in 60 mL of a mixed tetrahydrofuran (THF) and H$_2$O (2:1 by volume) solution to obtain a solution, which was then stirred at about 70° C. for about 5 hours. The reaction solution was cooled to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 6.86 g of Intermediate I-1 (Yield: 87%). This compound was identified using mass spectroscopy/fast atom bombardment (MS/FAB). C$_{21}$H$_{16}$BrNO$_2$: calc. 393.04. found 393.14

Synthesis of Intermediate I-2

3.94 g (10.0 mmol) of Intermediate I-1 and 5.77 g (22 mmol) of triphenylphosphine (PPh$_3$) were dissolved in 30 mL of 1,2-dichlorobenzene to obtain a solution, which was then stirred at about 220° C. for about 12 hours. The reaction solution was cooled to room temperature, and the solvent was removed therefrom under vacuum conditions, followed by three times of extraction with 50 mL of water and 50 mL of dichloromethane. The organic phase was collected and was dried using magnesium sulfate to evaporate the solvent. The residue was separated and purified using silica gel column chromatography to obtain 2.83 g of Intermediate I-2 (Yield: 78%). This compound was identified using MS/FAB. C$_{21}$H$_{16}$BrN: calc. 361.05. found 361.26

Synthesis of Intermediate I-3

3.62 g (10.0 mmol) of Intermediate I-2, 4.80 g (15.0 mmol) of 9,9-dimethyl-2-iodofluorene, 0.19 g (1.0 mmol) of CuI, 0.05 g (0.2 mmol) of 18-Crown-6, and 4.15 g (30.0 mmol) of K$_2$CO$_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled to room temperature, followed by three times of extraction with 50 mL of water and 50 mL of dichloromethane. The organic phase was collected and was dried using magnesium sulfate to evaporate the solvent. The residue was separated and purified using silica gel column chromatography to obtain 4.03 g of Intermediate I-3 (Yield: 92%). This compound was identified using MS/FAB. C$_{36}$H$_{28}$BrN: calc. 553.14. found 553.25

Synthesis of Intermediate I-4

8.461 g (50 mmol) of diphenylamine, 10.983 g (60 mmol) of bromostyrene (Compound E), 0.915 g (1 mmol) of Pd$_2$(dba)$_3$, 0.202 g (1 mmol) of PtBu$_3$, and 69.611 g (100 mmol) of KOtBu were dissolved in 300 mL of toluene to obtain a solution, which was then stirred at about 85° C. for about 4 hours. The reaction solution was cooled to room temperature, followed by three times of extraction with 100 mL of water and 100 mL of diethyl ether. The organic phase was collected and was dried using magnesium sulfate to evaporate the solvent. The residue was separated and purified using silica gel column chromatography to obtain 7.33 g of Intermediate I-4 (Yield: 54%). This compound was identified using MS/FAB. C$_{20}$H$_{17}$N: calc. 271.13. found 271.36

Synthesis of Compound 8

2.76 g (5 mmol) of Intermediate I-3, 1.36 g (5 mmol) of Intermediate I-4, 0.056 g (0.25 mmol) of Pd(OAc)$_2$, 0.76 g (0.25 mmol) of tri(o-tolyl)phosphinen ((p-tolyl)$_3$P), and 1.019 g (10 mmol) of triethylamine were dissolved in 100 mL of dimethylacetamide (DMAc) to obtain a solution, which was then stirred at about 85° C. for about 4 hours. The reaction solution was cooled to room temperature, followed by three times of extraction with 100 mL of water and 100 mL of diethyl ether. The organic phase was collected and was dried using magnesium sulfate to evaporate the solvent. The residue was separated and purified using silica gel column chromatography to obtain 1.71 g of Compound 8 (Yield: 46%). This compound was identified using MS/FAB. C$_{56}$H$_{44}$N$_2$: calc. 744.35. found 744.53

$^1$H NMR (CDCl$_3$, 400 MHz) δ (ppm) 8.18-8.14 (m, 1H), 7.93 (d, 1H), 7.88-7.85 (m, 1H), 7.76 (d, 1H), 7.71-7.69 (m, 1H), 7.64-7.60 (m, 2H), 7.48-7.45 (m, 3H), 7.40-7.38 (m, 1H), 7.35-7.30 (m, 3H), 7.23-7.03 (m, 9H), 6.70-6.63 (m, 5H), 617-6.13 (m, 4H), 1.76 (s, 6H), 1.64 (s, 6H)

Synthesis Example 2

Synthesis of Compound 16

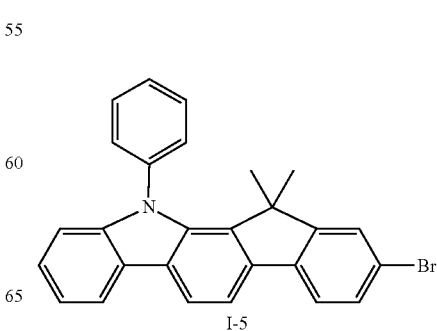

I-5

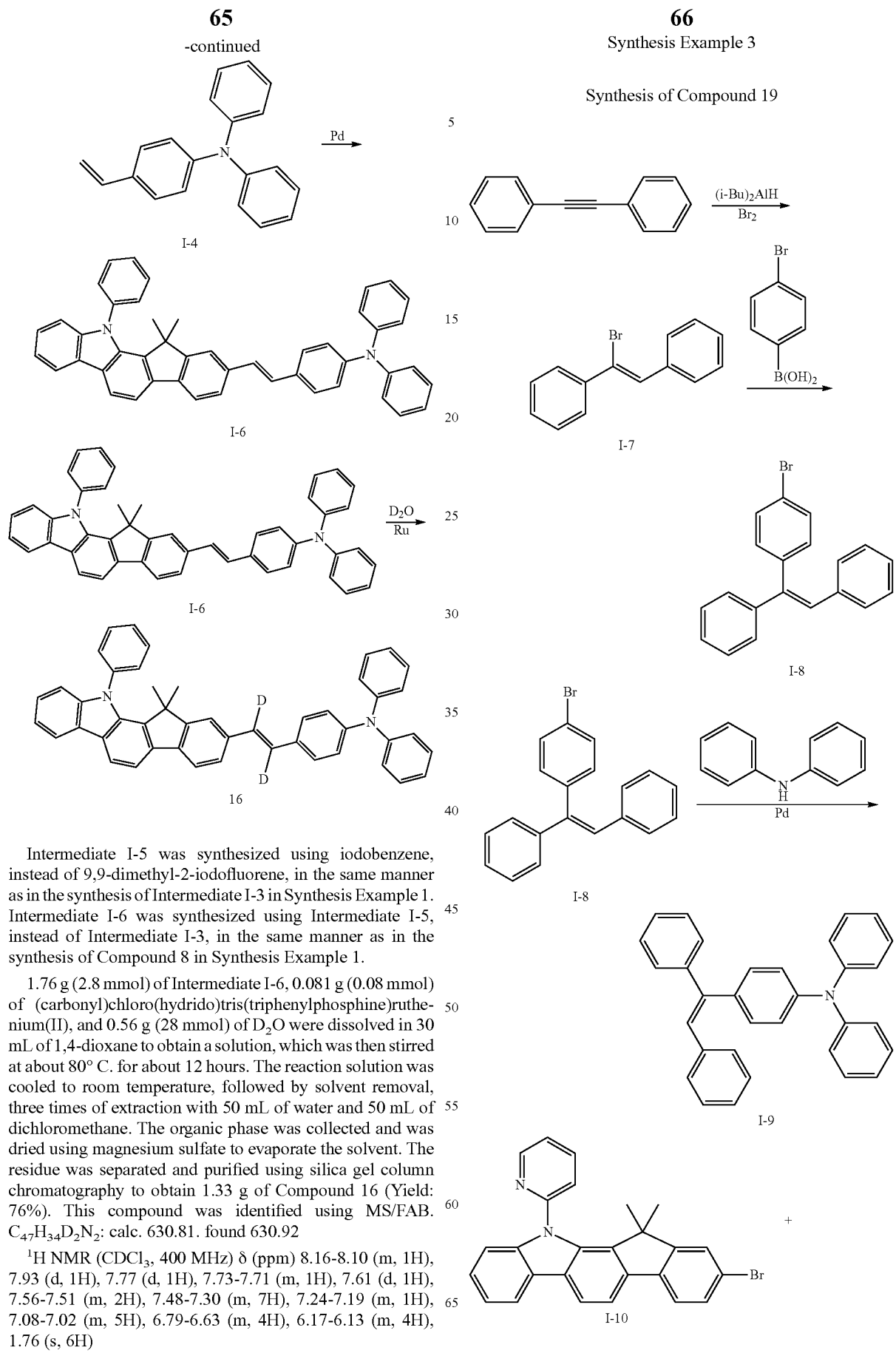

Synthesis Example 3

Synthesis of Compound 19

Intermediate I-5 was synthesized using iodobenzene, instead of 9,9-dimethyl-2-iodofluorene, in the same manner as in the synthesis of Intermediate I-3 in Synthesis Example 1. Intermediate I-6 was synthesized using Intermediate I-5, instead of Intermediate I-3, in the same manner as in the synthesis of Compound 8 in Synthesis Example 1.

1.76 g (2.8 mmol) of Intermediate I-6, 0.081 g (0.08 mmol) of (carbonyl)chloro(hydrido)tris(triphenylphosphine)ruthenium(II), and 0.56 g (28 mmol) of $D_2O$ were dissolved in 30 mL of 1,4-dioxane to obtain a solution, which was then stirred at about 80° C. for about 12 hours. The reaction solution was cooled to room temperature, followed by solvent removal, three times of extraction with 50 mL of water and 50 mL of dichloromethane. The organic phase was collected and was dried using magnesium sulfate to evaporate the solvent. The residue was separated and purified using silica gel column chromatography to obtain 1.33 g of Compound 16 (Yield: 76%). This compound was identified using MS/FAB. $C_{47}H_{34}D_2N_2$: calc. 630.81. found 630.92

$^1$H NMR (CDCl$_3$, 400 MHz) δ (ppm) 8.16-8.10 (m, 1H), 7.93 (d, 1H), 7.77 (d, 1H), 7.73-7.71 (m, 1H), 7.61 (d, 1H), 7.56-7.51 (m, 2H), 7.48-7.30 (m, 7H), 7.24-7.19 (m, 1H), 7.08-7.02 (m, 5H), 6.79-6.63 (m, 4H), 6.17-6.13 (m, 4H), 1.76 (s, 6H)

-continued

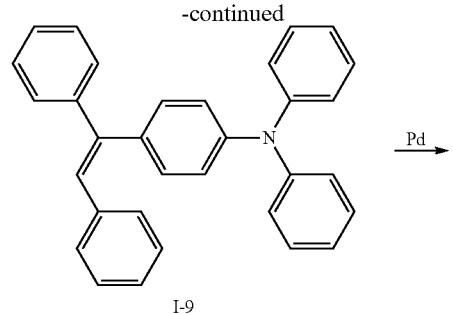

I-9

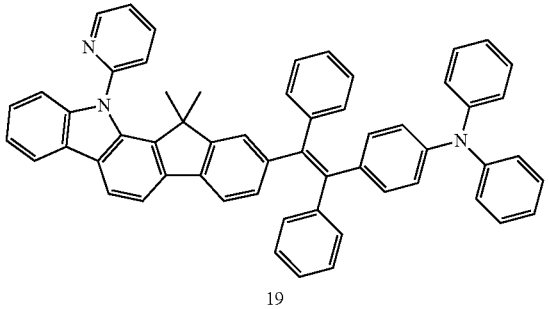

19

Synthesis of Intermediate I-7

1.96 ml (11.0 mmol) of diisobutylaluminiumhydride was added to 10 mL of tetrahydrofuran (THF) to obtain a solution, followed by temperature control to about 0° C., a slow dropwise addition of 1.78 mL (10.0 mL) of diphenylacetylene, and stirring at room temperature for about 6 hours. The reaction solution was cooled to about −78° C., and 0.77 mL (15.0 mmol) of a bromine solution was slowly added thereto over about 10 minutes. The temperature of the reaction solution was then raised to room temperature and stirred for about 1 hour. 10.0 mL of sodium potassium tartrate was slowly dropwise added to the reaction solution at about 0° C., followed by stirring at room temperature for about 30 minutes, and three times of extraction with 20 mL of water and 20 mL of diethylether. The organic phase was collected and was dried using magnesium sulfate to evaporate the solvent. The residue was separated and purified using silica gel column chromatography to obtain 1.74 g of Intermediate I-7 (Yield: 67%). This compound was identified using MS/FAB. $C_{56}H_{44}N_2$: calc. 258.00. found 258.13

Synthesis of Intermediate I-8

5.18 g (20.0 mmol) of Intermediate I-7, 4.02 g (20.0 mmol) of 4-bromophenyl boronic acid, 1.15 g (1.0 mmol) of tetrakis (triphenylphosphine)palladium (Pd(PPh$_3$)$_4$), and 8.29 g (60.0 mmol) of $K_2CO_3$ were dissolved in 60 mL of a mixed tetrahydrofuran (THF) and $H_2O$ (2:1 by volume) solution to obtain a solution, which was then stirred at about 70° C. for about 5 hours. The reaction solution was cooled to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 5.49 g of Intermediate I-8 (Yield: 82%). This compound was identified using MS/FAB. $C_{20}H_{15}Br$: calc. 334.04. found 334.14

Synthesis of Intermediate I-9

Intermediate I-9 was synthesized using Intermediate I-8, instead of 4-bromostyrene, in the same manner as in the synthesis of Intermediate I-4 in Synthesis Example 1.

Synthesis of Intermediate I-10

Intermediate I-10 was synthesized using 2-bromopyridine, instead of 9,9-dimethyl-2-iodofluorene, in the same manner as in the synthesis of Intermediate I-3 in Synthesis Example 1.

Synthesis of Compound 19

Compound 19 was synthesized using Intermediates I-10 and I-9, instead of Intermediates I-3 and I-4, in the same manner as in the synthesis of Compound 8 in Synthesis Example 1. This compound was identified using MS/FAB. $C_{58}H_{43}N_3$: calc. 781.34. found 781.53

$^1$H NMR (CDCl$_3$, 400 MHz) δ (ppm) 8.73-8.71 (m, 1H), 8.12-8.05 (m, 1H), 7.84-7.79 (m, 1H), 7.74-7.73 (m, 1H), 7.69-7.56 (m, 4H), 7.48-7.32 (m, 13H), 7.27-7.25 (m, 1H), 7.11-7.03 (m, 5H), 6.91-6.88 (m, 2H), 6.72-6.63 (m, 4H), 6.17-6.13 (m, 4H), 1.76 (s, 6H)

Synthesis Example 4

Synthesis of Compound 29

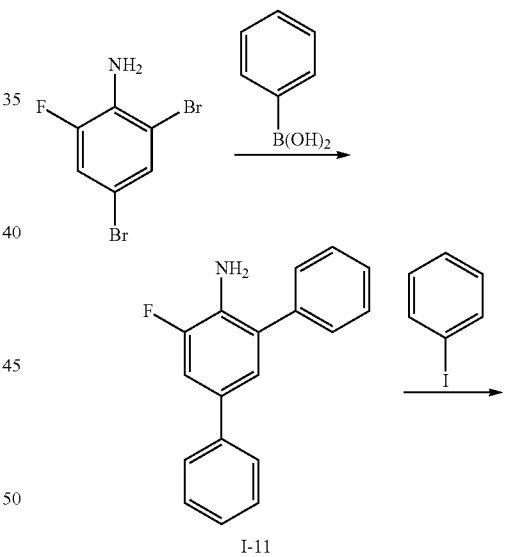

I-11

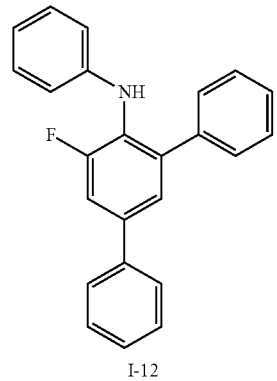

I-12

-continued

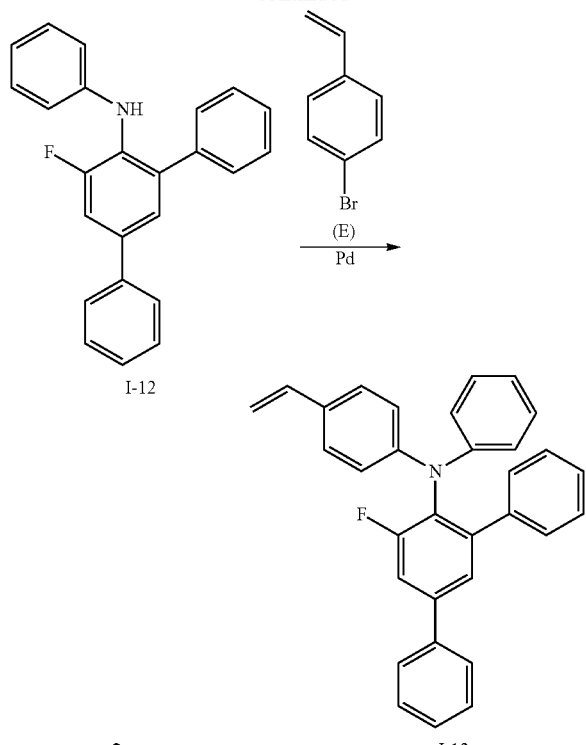

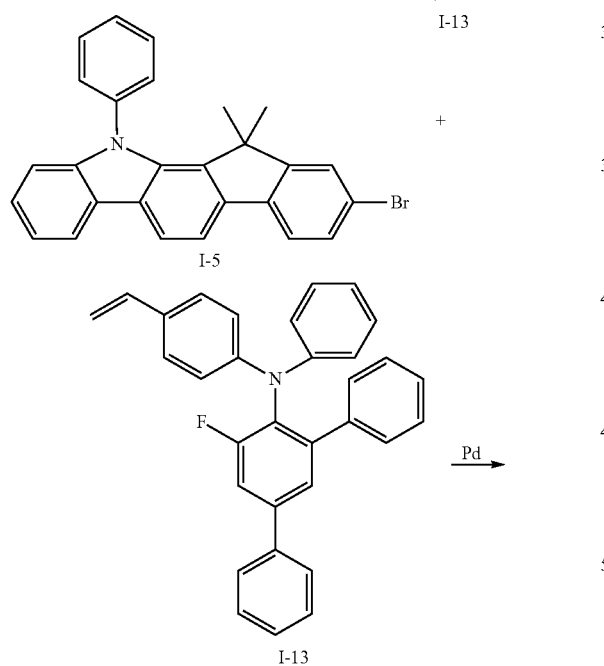

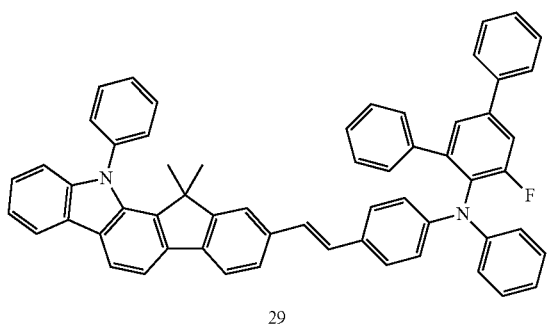

Synthesis of Intermediate I-11

5.37 g (20.0 mmol) of 2,4-dibromo-6-fluoro-phenylamine, 4.88 g (40.0 mmol) of phenylboronic acid, 1.15 g (1.0 mmol) of tetrakis(triphenylphosphine)palladium (Pd(PPh$_3$)$_4$), and 8.29 g (60.0 mmol) of K$_2$CO$_3$ were dissolved in 60 mL of a mixed tetrahydrofuran (THF) and H$_2$O (2:1 by volume) solution to obtain a solution, which was then stirred at about 70° C. for about 5 hours. The reaction solution was cooled to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 3.95 g of Intermediate I-11 (Yield: 75%). This compound was identified using MS/FAB. C$_{18}$H$_{14}$FN: calc. 263.11. found 263.25

Synthesis of Intermediate I-12

2.63 g (10 mmol) of Intermediate I-11, 2.45 g (12 mmol) of iodobenzene, 0.83 g (0.2 mmol) of Pd$_2$(dba)$_3$, 0.040 g (0.2 mmol) of PtBu$_3$, and 13.9 g (20 mmol) of KOtBu were dissolved in 60 mL of toluene to obtain a solution, which was then stirred at about 85° C. for about 4 hours. The reaction solution was cooled to room temperature, followed by three times of extraction with 100 mL of water and 100 mL of diethyl ether. The organic phase was collected and was dried using magnesium sulfate to evaporate the solvent. The residue was separated and purified using silica gel column chromatography to obtain 2.14 g of Intermediate I-12 (Yield: 63%). This compound was identified using MS/FAB. C$_{24}$H$_{18}$FN: calc. 339.14. found 339.29

Synthesis of Intermediate I-13

Intermediate I-13 was synthesized using Intermediate I-12, instead of diphenylamine, in the same manner as in the synthesis of Intermediate I-4 in Synthesis Example 1. This compound was identified using MS/FAB. C$_{32}$H$_{24}$FN: calc. 441.53. found 441.71

Synthesis of Compound 29

Compound 29 was synthesized using Intermediates I-5 and I-13, instead of Intermediates I-3 and I-4, in the same manner as in the synthesis of Compound 8 in Synthesis Example 1. This compound was identified using MS/FAB. C$_{59}$H$_{43}$FN$_2$: calc. 798.34. found 798.53

$^1$H NMR (CDCl$_3$, 400 MHz) δ (ppm) 8.16-8.11 (m, 1H), 7.93 (d, 1H), 7.77-7.76 (m, 1H), 7.72-7.70 (m, 2H), 7.65-7.59 (m, 3H), 7.55-7.29 (m, 18H), 7.24-7.19 (m, 1H), 7.14-7.04 (m, 5H), 6.66-6.60 (m, 3H), 6.15-6.12 (m, 2H), 1.78 (s, 6H)

Synthesis Example 5

Synthesis of Compound 39

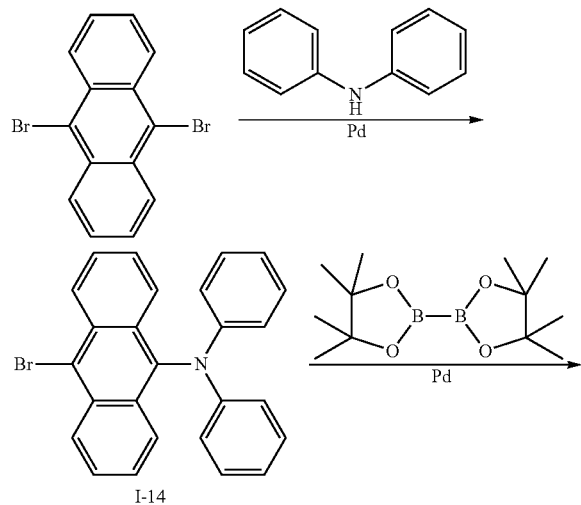

I-14

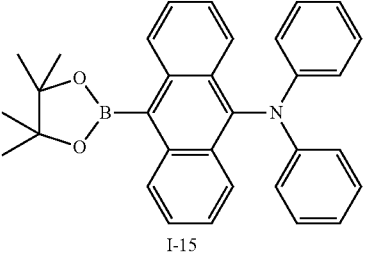

I-15

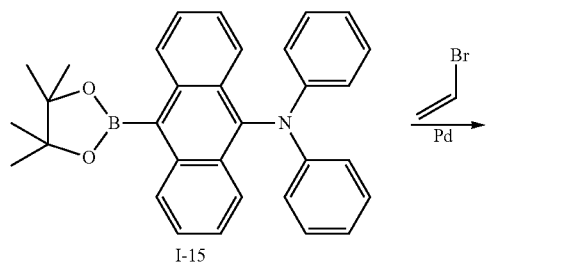

I-15

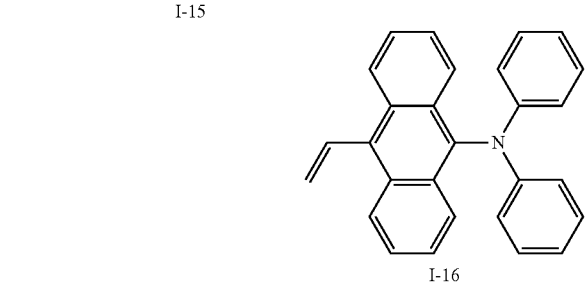

I-16

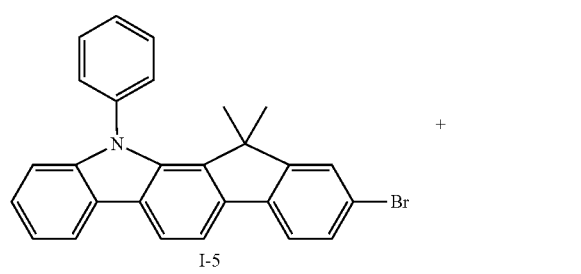

I-5

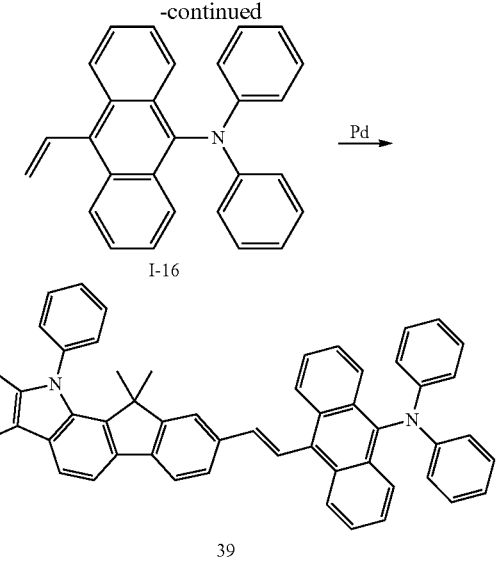

I-16

39

Synthesis of Intermediate I-14

20.1 g (60 mmol) of 9,10-dibromoanthracene, 8.461 g (50 mmol) of diphenylamine, 0.915 g (1 mmol) of $Pd_2(dba)_3$, 0.202 g (1 mmol) of $PtBu_3$, and 69.611 g (100 mmol) of KOtBu were dissolved in 300 mL of toluene to obtain a solution, which was then stirred at about 85° C. for about 4 hours. The reaction solution was cooled to room temperature, followed by three times of extraction with 100 mL of water and 100 mL of diethyl ether. The organic phase was collected and was dried using magnesium sulfate to evaporate the solvent. The residue was separated and purified using silica gel column chromatography to obtain 12.9 g of Intermediate I-14 (Yield: 61%). This compound was identified using MS/FAB. $C_{26}H_{18}BrN$: calc. 423.06. found 423.13

Synthesis of Intermediate I-15

4.24 g (10.0 mmol) of Intermediate I-14, 2.54 g (10.0 mmol) of bis(pinacolato)diborane, 0.36 g (0.5 mmol) of [1,1'-bis(diphenylphosphino)ferrocene]dichloro palladium (II) $(PdCl_2(dppf)_2)$, and 2.94 g (30.0 mmol) of KOAc were dissolved in 40 mL of DMSO to obtain a solution, which was then stirred at about 80° C. for about 6 hours. The reaction solution was cooled to room temperature, followed by three times of extraction with 50 mL of water and 50 mL of diethylether. The organic phase was collected and was dried using magnesium sulfate to evaporate the solvent. The residue was separated and purified using silica gel column chromatography to obtain 1.88 g of Intermediate I-15 (Yield: 74%). This compound was identified using MS/FAB. $C_{32}H_{30}BNO_2$: calc. 471.23. found 471.33

Synthesis of Intermediate I-16

Intermediate I-16 was synthesized using Intermediate I-15 and vinyl bromide, instead of 4-bromophenyl boronic acid and Intermediate I-7, in the same manner as in the synthesis of Intermediate I-8 in Synthesis Example 3. This compound was identified using MS/FAB. $C_{28}H_{21}N$: calc. 371.47. found 371.61

Synthesis of Compound 39

Compound 39 was synthesized using Intermediates I-5 and I-16, instead of Intermediates I-3 and I-4, in the same manner as in the synthesis of Compound 8 in Synthesis Example 1. This compound was identified using MS/FAB. $C_{55}H_{40}N_2$: calc. 728.31. found 728.54

$^1$H NMR (CDCl$_3$, 400 MHz) δ (ppm) 8.17-8.11 (m, 1H), 7.93 (d, 1H), 7.89-7.86 (d, 1H), 7.75-7.72 (m, 2H), 7.62-7.58 (m, 3H), 7.56-7.48 (m, 3H), 7.44-7.41 (m, 2H), 7.38-7.30 (m, 4H), 7.24-7.19 (m, 1H), 7.15 (s, 1H), 7.11 (s, 1H), 7.04-6.98 (m, 6H), 6.88-6.84 (m, 2H), 6.63-6.60 (m, 2H), 5.96-5.94 (m, 4H), 1.77 (s, 6H)

Synthesis Example 6

Synthesis of Compound 47

Synthesis of Intermediate I-17

Intermediate I-17 was synthesized using Intermediate I-5, instead of Intermediate I-14, in the same manner as in the synthesis of Intermediate I-15 in Synthesis Example 5. This compound was identified using MS/FAB. $C_{33}H_{32}BNO_2$: calc. 485.25. found 485.33

Synthesis of Intermediate I-18

Intermediate I-18 was synthesized using Intermediate I-17 and 2,5-dibromopyridine, instead of 2-bromonitrobenzene and 2-bromo-9,9-dimethyl-7-fluoreneboronic acid, in the

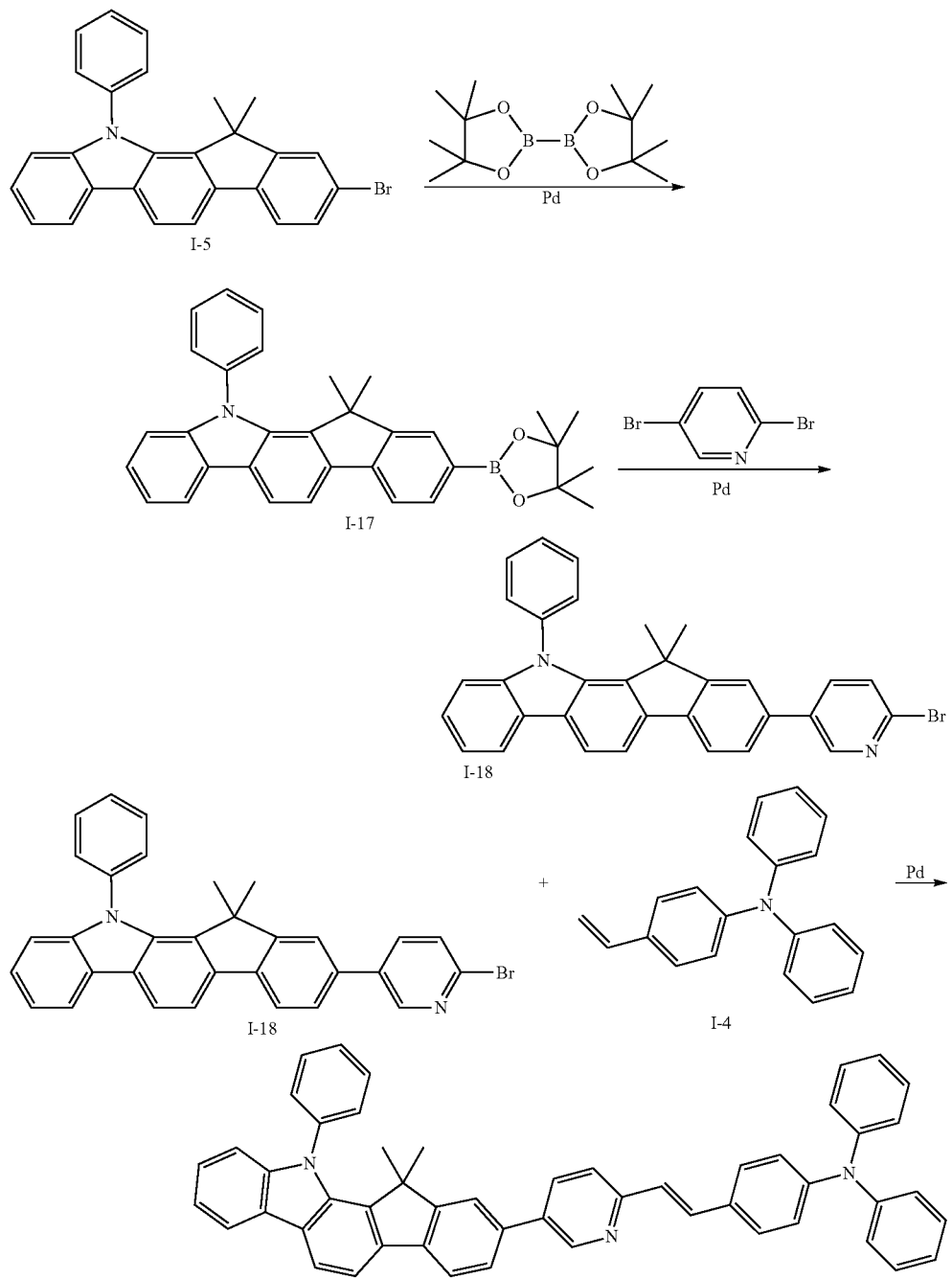

same manner as in the synthesis of Intermediate I-1 in Synthesis Example 1. This compound was identified using MS/FAB. $C_{32}H_{23}BrN_2$: calc. 515.44. found 515.62

Synthesis of Compound 47

Compound 47 was synthesized using Intermediate I-18, instead of Intermediate I-3, in the same manner as in the synthesis of Compound 8 in Synthesis Example 1. This compound was identified using MS/FAB. $C_{52}H_{39}N_3$: calc. 705.31. found 705.43

$^1$H NMR (CDCl$_3$, 400 MHz) δ (ppm) 8.87-8.85 (m, 1H), 8.16-8.12 (m, 1H), 8.07-8.04 (m, 1H), 7.92 (d, 1H), 7.86-7.83 (m, 1H), 7.78 (d, 1H), 7.69-7.67 (m, 1H), 7.62-7.57 (m, 2H), 7.56-7.48 (m, 4H), 7.44-7.41 (m, 2H), 7.38-7.30 (m, 4H), 7.26-7.19 (m, 2H), 7.08-7.03 (m, 4H), 6.85-6.82 (m, 2H), 6.66-6.63 (m, 2H), 6.17-6.13 (m, 4H), 1.76 (s, 6H)

Synthesis Example 7

Synthesis of Compound 1

Compound 1 was synthesized using ethyliodide (C$_2$H$_5$I), instead of 9,9-dimethyl-2-iodofluorene, in the same manner as in the synthesis of Compound 8 in Synthesis Example 1. This compound was identified using MS/FAB. $C_{43}H_{36}N_2$: calc. 580.28. found 580.42

$^1$H NMR (CDCl$_3$, 400 MHz) δ (ppm) 8.17 (d, 1H), 8.00 (d, 1H), 7.75 (d, 1H), 7.69-7.65 (m, 2H), 7.49-7.36 (m, 6H), 7.24-7.20 (m, 1H), 7.08-7.00 (m, 5H), 6.69-6.63 (m, 4H), 6.17-6.12 (m, 4H), 4.71 (q, 2H), 1.77 (s, 6H), 1.31 (t, 3H)

Synthesis Example 8

Synthesis of Compound 3

Compound 3 was synthesized using iodobenzene (C$_6$H$_5$I), instead of 9,9-dimethyl-2-iodofluorene, in the same manner as in the synthesis of Compound 8 in Synthesis Example 1. This compound was identified using MS/FAB. $C_{47}H_{36}N_2$: calc. 628.28. found 628.41

$^1$H NMR (CDCl$_3$, 400 MHz) δ (ppm) 8.16-8.10 (m, 1H), 7.93 (d, 1H), 7.77 (d, 1H), 7.73-7.71 (m, 1H), 7.61 (d, 1H), 7.56-7.51 (m, 3H), 7.48-7.30 (m, 9H), 7.24-7.19 (m, 1H), 7.08-7.02 (m, 4H), 6.79-6.63 (m, 4H), 6.17-6.13 (m, 4H), 1.76 (s, 6H)

Synthesis Example 9

Synthesis of Compound 4

Compound 4 was synthesized using 2-iodonaphthalene, instead of 9,9-dimethyl-2-iodofluorene, in the same manner as in the synthesis of Compound 8 in Synthesis Example 1. This compound was identified using MS/FAB. $C_{51}H_{38}N_2$: calc. 678.30. found 678.61

$^1$H NMR (CDCl$_3$, 400 MHz) δ (ppm) 8.16-8.10 (m, 1H), 7.93 (d, 2H), 7.84 (d, 1H), 7.75 (d, 1H), 7.72-7.70 (m, 1H), 7.65-7.61 (m, 2H), 7.57-7.52 (m, 2H), 7.48-7.30 (m, 9H), 7.22-7.18 (m, 1H), 7.08-7.03 (m, 5H), 6.7-6.63 (m, 4H), 6.17-6.13 (m, 3H), 1.76 (s, 6H)

Synthesis Example 10

Synthesis of Compound 5

Compound 5 was synthesized using 9-bromophenanthrene, instead of 9,9-dimethyl-2-iodofluorene, in the same manner as in the synthesis of Compound 8 in Synthesis Example 1. This compound was identified using MS/FAB. $C_{55}H_{40}N_2$: calc. 728.31. found 728.62

$^1$H NMR (CDCl$_3$, 400 MHz) δ (ppm) 8.66-8.64 (m, 1H), 8.31-8.29 (m, 1H), 8.17-8.12 (m, 2H), 7.98 (d, 1H), 7.76 (d, 1H), 7.71-7.64 (m, 3H), 7.59-7.54 (m, 1H), 7.51-7.30 (m, 9H), 7.35-7.30 (m, 2H), 7.08-7.03 (m, 5H), 6.70-6.63 (m, 4H), 617-6.13 (m, 4H), 1.76 (s, 6H)

Synthesis Example 11

Synthesis of Compound 7

Compound 7 was synthesized using 4-bromobiphenyl, instead of 9,9-dimethyl-2-iodofluorene, in the same manner as in the synthesis of Compound 8 in Synthesis Example 1. This compound was identified using MS/FAB. $C_{53}H_{40}N_2$: calc. 704.31. found 704.65

$^1$H NMR (CDCl$_3$, 400 MHz) δ (ppm) 8.16-8.10 (m, 1H), 7.93 (d, 1H), 7.76 (d, 1H), 7.71-7.69 (m, 1H), 7.64-7.59 (m, 3H), 7.53-7.38 (m, 9H), 7.35-7.29 (m, 3H), 7.20-7.16 (m, 2H), 7.08-7.03 (m, 5H), 6.70-6.63 (m, 4H), 6.17-6.13 (m, 4H), 1.76 (s, 6H)

Synthesis Example 12

Synthesis of Compound 9

Compound 9 was synthesized using iodobenzene-d5, instead of 9,9-dimethyl-2-iodofluorene, in the same manner as in the synthesis of Compound 8 in Synthesis Example 1. This compound was identified using MS/FAB. $C_{47}H_{31}D_5N_2$: calc. 633.31. found 633.59

$^1$H NMR (CDCl$_3$, 400 MHz) δ (ppm) 8.16-8.10 (m, 1H), 7.93 (d, 1H), 7.76 (d, 1H), 7.71-7.69 (m, 1H), 7.62-7.59 (m, 1H), 7.48-7.44 (m, 2H), 7.35-7.30 (m, 3H), 7.23-7.19 (m, 1H), 7.08-7.03 (m, 6H), 6.70-6.63 (m, 4H), 6.17-6.13 (m, 4H), 1.76 (s, 6H)

Synthesis Example 13

Synthesis of Compound 12

Compound 9 was synthesized using Intermediate I-19, instead of 9,9-dimethyl-2-iodofluorene, in the same manner as in the synthesis of Compound 8 in Synthesis Example 1. This compound was identified using MS/FAB. $C_{56}H_{41}N_5$: calc. 783.33. found 783.54

$^1$H NMR (CDCl$_3$, 400 MHz) δ (ppm) 8.83 (d, 1H), 8.78-8.75 (m, 3H), 8.15 (m, 1H), 7.92-7.88 (m, 1H), 7.77 (d, 1H), 7.71-7.57 (m, 7H), 7.48-7.35 (m, 8H), 7.08-7.03 (m, 5H), 6.68-6.63 (m, 4H), 617-6.13 (m, 4H), 1.76 (s, 6H)

Synthesis Example 14

Synthesis of Compound 14

Intermediate I-20 was synthesized using 2-bromo-9,9-diphenyl-7-fluoreneboronic acid and iodobenzene, instead of 2-bromo-9,9-dimethyl-7-fluoreneboronic acid and 9,9-dimethyl-2-iodofluorene, in the same manner as in the synthesis of Compound 8 in Synthesis Example 1.

Intermediate 14 was synthesized using Intermediate I-20, instead of Intermediate I-6, in the same manner as in the synthesis of Compound 16 in Synthesis Example 2. This compound was identified using MS/FAB.

$C_{57}H_{38}D_2N_2$: calc. 754.33. found 754.61

¹H NMR (CDCl₃, 400 MHz) δ (ppm) 8.16-8.10 (m, 2H), 7.74 (d, 1H), 7.56-7.51 (m, 2H), 7.47-7.31 (m, 12H), 7.26-7.22 (m, 1H), 7.15-7.11 (m, 1H), 7.08-6.98 (m, 13H), 6.69-6.63 (m, 3H), 6.16-6.13 (m, 3H), Synthesis Example 15

Synthesis of Compound 17

Compound 17 was synthesized using Intermediate I-5, instead of Intermediate I-10, in the same manner as in the synthesis of Compound 19 in Synthesis Example 3. This compound was identified using MS/FAB.

$C_{59}H_{44}N_2$: calc. 780.35. found 780.58

¹H NMR (CDCl₃, 400 MHz) δ (ppm) 8.16-8.10 (m, 1H), 7.77 (d, 1H), 7.69-7.66 (m, 2H), 7.61-7.59 (m, 1H), 7.56-7.51 (m, 2H), 7.48-7.30 (m, 14H), 7.24-7.19 (m, 1H), 7.11-7.03 (m, 6H), 6.91-6.88 (m, 2H), 6.72-6.63 (m, 4H), 6.17-6.13 (m, 4H), 1.76 (s, 6H)

Synthesis Example 16

Synthesis of Compound 20

Intermediate I-22 was synthesized using Intermediate I-21, instead of 9,9-dimethyl-2-iodofluorene, in the same manner as in the synthesis of Compound 8 in Synthesis Example 1.

Compound 20 was synthesized using Intermediate I-22, instead of Intermediate I-6, in the same manner as in the synthesis of Compound 16 in Synthesis Example 2. This compound was identified using MS/FAB.

$C_{59}H_{42}D_2N_2$: calc. 782.36. found 782.59

¹H NMR (CDCl₃, 400 MHz) δ (ppm) 8.26-8.21 (m, 1H), 7.93 (d, 1H), 7.81-7.76 (m, 5H), 7.72-7.70 (m, 1H), 7.66-7.64 (m, 1H), 7.55-7.50 (m, 5H), 7.47-7.29 (m, 9H), 7.08-7.03 (m, 4H), 6.69-6.63 (m, 5H), 6.16-6.13 (m, 4H), 1.78 (s, 6H)

Synthesis Example 17

Synthesis of Compound 21

Compound 21 was synthesized using tert-butyl iodide and Intermediates I-23 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB. $C_{47}H_{44}N_2$: calc. 636.35. found 636.59

¹H NMR (CDCl₃, 400 MHz) δ (ppm) 7.97-7.94 (m, 1H), 7.92 (d, 1H), 7.77-7.74 (m, 1H), 7.70 (d, 1H), 7.65-7.63 (m, 1H), 7.48-7.39 (m, 5H), 7.35-7.19 (m, 5H), 7.07-7.03 (m, 4H), 6.99-6.94 (m, 3H), 6.82-6.78 (m, 3H), 6.63-6.61 (m, 2H), 6.53-6.50 (m, 2H), 1.87 (s, 3H), 1.80 (s, 6H), 1.79 (s, 6H)

Synthesis Example 18

Synthesis of Compound 22

Compound 22 was synthesized using iodobenzene and Intermediate I-24 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB. $C_{48}H_{37}FN_2$: 22. calc. 660.29. found 660.42

¹H NMR (CDCl₃, 400 MHz) δ (ppm) 8.16-8.10 (m, 1H), 7.93 (d, 1H), 7.77 (d, 1H), 7.72-7.70 (m, 1H), 7.62-7.59 (m, 1H), 7.56-7.51 (m, 2H), 7.48-7.31 (m, 9H), 7.24-7.19 (m, 1H), 7.10-7.03 (m, 3H), 7.00-6.92 (m, 3H), 6.82-6.78 (m, 1H), 6.70-6.67 (m, 1H), 6.63-6.57 (m, 3H), 2.01 (s, 3H), 1.76 (s, 6H)

Synthesis Example 19

Synthesis of Compound 23

Compound 23 was synthesized using iodobenzene and Intermediate I-25 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB.

$C_{48}H_{35}N_3$: calc. 653.28. found 653.49

¹H NMR (CDCl₃, 400 MHz) δ (ppm) 8.16-8.10 (m, 1H), 7.93 (d, 1H), 7.77 (d, 1H), 7.72-7.70 (m, 1H), 7.62-7.59 (m, 1H), 7.56-7.51 (m, 2H), 7.48-7.30 (m, 11H), 7.24-7.19 (m, 1H), 7.10-7.03 (m, 3H), 6.78-6.73 (m, 4H), 6.66-6.63 (m, 1H), 6.22-6.20 (m, 2H), 1.73 (s, 6H)

Synthesis Example 20

Synthesis of Compound 26

Compound 26 was synthesized using Intermediate I-26, instead of Intermediate I-4, in the same manner as in the synthesis of Compound 16 in Synthesis Example 2. This compound was identified using MS/FAB.

$C_{57}H_{38}D_2N_2$: calc. 754.33. found 754.51

¹H NMR (CDCl₃, 400 MHz) δ (ppm) 8.16-8.12 (m, 3H), 8.04-8.00 (m, 2H), 7.93 (d, 1H), 7.82-7.76 (m, 4H), 7.71-7.69 (m, 1H), 7.62-7.51 (m, 5H), 7.46-7.31 (m, 9H), 7.24-7.19 (m, 1H), 7.06-7.01 (m, 2H), 6.73-6.70 (m, 2H), 6.65-6.61 (m, 1H), 6.22-6.17 (m, 2H), 1.75 (s, 6H)

Synthesis Example 21

Synthesis of Compound 27

Compound 27 was synthesized using Intermediate I-27, instead of Intermediate I-4, in the same manner as in the synthesis of Compound 16 in Synthesis Example 2. This compound was identified using MS/FAB.

$C_{56}H_{42}D_2N_2$: calc. 746.36. found 746.41

¹H NMR (CDCl₃, 400 MHz) δ (ppm) 8.17-8.11 (m, 1H), 7.93 (d, 1H), 7.77-7.71 (m, 2H), 7.72-7.71 (m, 1H), 7.61 (d, 1H), 7.56-7.51 (m, 3H), 7.48-7.30 (m, 7H), 7.23-7.19 (m, 1H), 7.14-7.04 (m, 5H), 6.73-6.63 (m, 5H), 6.39-6.37 (m, 1H), 6.23-6.20 (m, 2H), 1.76 (s, 6H), 1.61 (s, 6H)

Synthesis Example 22

Synthesis of Compound 28

Compound 28 was synthesized using Intermediate I-28, instead of Intermediate I-4, in the same manner as in the synthesis of Compound 16 in Synthesis Example 2. This compound was identified using MS/FAB.

$C_{59}H_{41}D_2N_3$: calc. 795.35. found 795.53

¹H NMR (CDCl₃, 400 MHz) δ (ppm) 8.22-8.20 (m, 1H), 8.16-8.11 (m, 1H), 7.93 (d, 1H), 7.77-7.76 (m, 1H), 7.72-7.70

(m, 1H), 7.62-7.59 (m, 1H), 7.56-7.19 (m, 21H), 7.09-7.04 (m, 2H), 6.87-6.81 (m, 3H), 6.66-6.63 (m, 1H), 6.31-6.29 (m, 2H), 1.77 (s, 6H)

Synthesis Example 23

Synthesis of Compound 30

Compound 30 was synthesized using Intermediate I-30, instead of Intermediate I-4, in the same manner as in the synthesis of Compound 16 in Synthesis Example 2. This compound was identified using MS/FAB.

$C_{47}H_{24}D_{12}N_2$: calc. 640.36. found 640.58

$^1$H NMR (CDCl$_3$, 400 MHz) δ (ppm) 8.16-8.11 (m, 1H), 7.93 (d, 1H), 7.77 (d, 1H), 7.72-7.70 (m, 1H), 7.62-7.59 (m, 1H), 7.54-7.51 (m, 2H), 7.46-7.29 (m, 8H), 7.23-7.19 (m, 1H), 6.69-6.66 (m, 2H), 1.76 (s, 6H)

Synthesis Example 24

Synthesis of Compound 31

Compound 31 was synthesized using iodobenzene and Intermediate I-31 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB.

$C_{45}H_{34}N_4$: calc. 630.27. found 630.39

$^1$H NMR (CDCl$_3$, 400 MHz) δ (ppm) 8.53-8.50 (m, 2H), 8.16-8.11 (m, 1H), 8.08-8.06 (m, 2H), 7.93 (d, 1H), 7.77-7.76 (m, 1H), 7.72-7.70 (m, 1H), 7.62-7.59 (m, 1H), 7.55-7.30 (m, 12H), 7.24-7.20 (m, 1H), 7.17-7.14 (m, 2H), 7.07 (s, 1H), 7.03 (s, 1H), 6.97-6.93 (m, 2H), 1.75 (s, 6H)

Synthesis Example 25

Synthesis of Compound 35

Compound 35 was synthesized using iodobenzene and Intermediate I-32 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB.

$C_{53}H_{38}N_2S$: calc. 734.27. found 734.59

$^1$H NMR (CDCl$_3$, 400 MHz) δ (ppm) 8.16-8.12 (m, 1H), 8.06-8.04 (m, 1H), 7.93 (d, 1H), 7.82 (d, 1H), 7.75 (d, 1H), 7.72-7.70 (m, 2H), 7.68-7.66 (m, 1H), 7.62-7.57 (m, 2H), 7.56-7.29 (m, 12H), 7.24-7.19 (m, 1H), 7.09-7.03 (m, 3H), 6.87-6.81 (m, 3H), 6.66-6.63 (m, 1H), 6.32-6.29 (m, 2H), 1.78 (s, 6H)

Synthesis Example 26

Synthesis of Compound 36

Compound 36 was synthesized using iodobenzene and Intermediate I-33 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB.

$C_{53}H_{38}N_2O$: calc. 718.29. found 718.59

$^1$H NMR (CDCl$_3$, 400 MHz) δ (ppm) 8.17-8.12 (m, 1H), 7.93 (d, 1H), 7.83 (d, 1H), 7.77-7.71 (m, 4H), 7.62-7.56 (m, 3H), 7.55-7.30 (m, 12H), 7.24-7.19 (m, 1H), 7.09-7.03 (m, 3H), 6.92-6.88 (m, 1H), 6.84-6.81 (m, 2H), 6.66-6.63 (m, 1H), 6.32-6.29 (m, 2H), 1.78 (s, 6H)

Synthesis Example 27

Synthesis of Compound 37

Compound 37 was synthesized using iodobenzene and Intermediate I-34 in the synthesis of Intermediate I-3, instead of 9,9-dimethyl-2-iodofluorene and diphenylamine, in the same manner as in the synthesis of Compound 8 in Synthesis Example 1. This compound was identified using MS/FAB.

$C_{53}H_{52}N_2Si_2$: calc. 772.36. found 772.55

$^1$H NMR (CDCl$_3$, 400 MHz) δ (ppm) 8.17-8.11 (m, 1H), 7.93 (d, 1H), 7.83 (d, 1H), 7.77-7.75 (m, 1H), 7.72-7.70 (m, 1H), 7.62-7.59 (m, 1H), 7.56-7.51 (m, 2H), 7.48-7.41 (m, 4H), 7.39-7.30 (m, 7H), 7.22-7.19 (m, 1H), 7.07 (s, 1H), 7.03 (s, 1H), 6.83-6.80 (m, 2H), 6.60-6.56 (m, 4H), 1.76 (s, 6H), 0.24 (s, 18H)

Synthesis Example 28

Synthesis of Compound 40

Compound 40 was synthesized using 1,4-dibromobenzene, instead of 9,10-dibromoanthracene, in the same manner as in the synthesis of Compound 39 in Synthesis Example 5. This compound was identified using MS/FAB.

$C_{53}H_{40}N_2$: calc. 704.31. found 704.54

$^1$H NMR (CDCl$_3$, 400 MHz) δ (ppm) 8.17-8.11 (m, 1H), 7.93 (d, 1H), 7.77 (d, 1H), 7.71-7.70 (m, 1H), 7.62-7.59 (m, 1H), 7.56-7.41 (m, 11H), 7.38-7.30 (m, 3H), 7.24-7.19 (m, 1H), 7.08-7.01 (m, 6H), 6.86-6.82 (m, 2H), 6.66-6.63 (m, 2H), 6.16-6.13 (m, 4H), 1.78 (s, 6H)

Synthesis Example 29

Synthesis of Compound 41

Intermediate I-35 was synthesized using 2,7-dibromo-9,9-dimethylfluorene, instead of 9,10-dibromoanthracene, in the same manner as in the synthesis of Compound 39 in Synthesis Example 5.

Compound 41 was synthesized using Intermediate I-35, instead of Intermediate I-6, in the same manner as in the synthesis of Compound 16 in Synthesis Example 2. This compound was identified using MS/FAB.

$C_{56}H_{42}D_2N_2$: calc. 746.36. found 746.62

$^1$H NMR (CDCl$_3$, 400 MHz) δ (ppm) 8.17-8.11 (m, 1H), 7.93 (d, 1H), 7.77-7.59 (m, 6H), 7.56-7.52 (m, 2H), 7.44-7.30 (m, 7H), 7.24-7.19 (m, 1H), 7.09-7.04 (m, 4H), 6.67-6.63 (m, 3H), 6.46-6.45 (m, 1H), 6.16-6.13 (m, 4H), 1.78 (s, 6H), 1.61 (s, 6H)

Synthesis Example 30

Synthesis of Compound 44

Compound 44 was synthesized using 1,4-dibromobenzene in the synthesis of Intermediate I-18, instead of 2,5-dibromopyridine, in the same manner as in the synthesis of Compound 47 in Synthesis Example 6. This compound was identified using MS/FAB. $C_{53}H_{40}N_2$: calc. 704.31. found 704.43

$^1$H NMR (CDCl$_3$, 400 MHz) δ (ppm) 8.17-8.11 (m, 1H), 7.83-7.77 (m, 3H), 7.66-7.59 (m, 2H), 7.54-7.50 (m, 2H), 7.48-7.30 (m, 6H), 7.38-7.30 (m, 4H), 7.26 (s, 1H), 7.22-7.19 (m, 1H), 7.08-7.03 (m, 4H), 6.91 (s, 1H), 6.87 (s, 1H), 6.70-6.63 (m, 4H), 6.17-6.13 (m, 4H), 1.78 (s, 6H)

Synthesis Example 31

Synthesis of Compound 48

Compound 48 was synthesized using 2,5-dibromofuran, instead of 2,5-dibromopyridine, in the same manner as in the synthesis of Compound 47 in Synthesis Example 6. This compound was identified using MS/FAB. $C_{51}H_{38}N_2O$: calc. 694.29. found 694.51

$^1$H NMR (CDCl$_3$, 400 MHz) . . . 8.17-8.11 (m, 1H), 7.96-7.93 (m, 1H), 7.79-7.76 (m, 2H), 7.62-7.51 (m, 5H), 7.46-7.41 (m, 3H), 7.38-7.30 (m, 3H), 7.24-7.19 (m, 2H), 7.08-7.00 (m, 5H), 6.93-6.91 (m, 1H), 6.70-6.63 (m, 5H), 6.16-6.13 (m, 4H), 1.79 (s, 6H)

Synthesis Example 32

Synthesis of Compound 49

Compound 49 was synthesized using 2,5-dibromothiophene, instead of 2,5-dibromopyridine, in the same manner as in the synthesis of Compound 47 in Synthesis Example 6. This compound was identified using MS/FAB. $C_{51}H_{38}N_2S$: calc. 710.27. found 710.46

$^1$H NMR (CDCl$_3$, 400 MHz) . . . 8.17-8.11 (m, 1H), 7.85-7.83 (m, 1H), 7.78 (d, 1H), 7.62-7.59 (m, 1H), 7.56-7.50 (m, 4H), 7.44-7.41 (m, 2H), 7.38-7.30 (m, 5H), 7.28-7.19 (m, 2H), 7.12-7.02 (m, 7H), 6.76-6.73 (m, 2H), 6.66-6.63 (m, 2H), 6.16-6.13 (m, 4H), 1.79 (s, 6H)

Synthesis Example 33

Synthesis of Compound 51

Compound 51 was synthesized using 2,7-dibromo-9,9-dimethyl-9H-fluorene, instead of 2,5-dibromopyridine, in the same manner as in the synthesis of Compound 47 in Synthesis Example 6. This compound was identified using MS/FAB. $C_{62}H_{48}N_2$: calc. 820.38. found 820.46 $^1$H NMR (CDCl$_3$, 400 MHz) . . . 8.17-8.11 (m, 1H), 7.82-7.77 (m, 2H), 7.69-7.64 (m, 4H), 7.62-7.59 (m, 1H), 7.57-7.30 (m, 14H), 7.24-7.19 (m, 1H), 7.08-7.03 (m, 5H), 6.70-6.63 (m, 4H), 6.16-6.13 (m, 4H), 1.70 (s, 6H), 1.60 (s, 6H)

Synthesis Example 34

Synthesis of Compound 54

Intermediate I-36 was synthesized using 2-bromo-4-(trifluoromethyl)-1-nitrobenzene in the synthesis of Intermediate I-1, instead of 2-bromonitrobenzene, in the same manner as in the synthesis of Compound 8 in Synthesis Example 1.

Intermediate 54 was synthesized using Intermediate I-36, instead of Intermediate I-6, in the same manner as in the synthesis of Compound 16 in Synthesis Example 2. This compound was identified using MS/FAB.

$C_{48}H_{33}D_2F_3N_2$: calc. 698.28. found 698.41

$^1$H NMR (CDCl$_3$, 400 MHz) δ (ppm) 8.12-8.10 (m, 1H), 7.90 (d, 1H), 7.77-7.74 (m, 2H), 7.71-7.70 (m, 1H), 7.63 (d, 1H), 7.56-7.50 (m, 2H), 7.47-7.34 (m, 6H), 7.08-7.04 (m, 5H), 6.69-6.63 (m, 4H), 6.17-6.13 (m, 4H), 1.76 (s, 6H)

Synthesis Example 35

Synthesis of Compound 56

Intermediate I-38 was synthesized using Intermediate I-37 in the synthesis of Intermediate I-1, instead of 2-bromonitrobenzene, in the same manner as in the synthesis of Compound 8 in Synthesis Example 2.

Intermediate 56 was synthesized using Intermediate I-38, instead of Intermediate I-6, in the same manner as in the synthesis of Compound 16 in Synthesis Example 2. This compound was identified using MS/FAB.

$C_{53}H_{38}D_2N_2$: calc. 706.33. found 706.57

$^1$H NMR (CDCl$_3$, 400 MHz) δ (ppm) 8.00-7.99 (m, 1H), 7.91 (d, 1H), 7.78-7.76 (m, 1H), 7.73-7.69 (m, 2H), 7.66-7.61 (m, 2H), 7.56-7.34 (m, 13H), 7.08-7.03 (m, 4H), 6.70-6.63 (m, 4H), 6.17-6.13 (m, 4H), 1.78 (s, 6H)

Synthesis Example 36

Synthesis of Compound 61

Compound 61 was synthesized using Intermediate I-39 and iodobenzene in the synthesis of Intermediate I-1, instead of 2-bromonitrobenzene and 9,9-dimethyl-2-iodofluorene, in the same manner as in the synthesis of Compound 8 in Synthesis Example 1. This compound was identified using MS/FAB. $C_{59}H_{45}N_3$: calc. 795.36. found 795.61

$^1$H NMR (CDCl$_3$, 400 MHz) δ (ppm) 7.96 (d, 1H), 7.77 (d, 1H), 7.72-7.70 (m, 1H), 7.65-7.64 (m, 1H), 7.56-7.51 (m, 2H), 7.49-7.42 (m, 5H), 7.39-7.34 (m, 3H), 7.15-7.13 (m, 1H), 7.09-7.03 (m, 9H), 6.76-6.73 (m, 1H), 6.70-6.62 (m, 6H), 6.25-6.21 (m, 4H), 6.17-6.12 (m, 4H), 1.80 (s, 6H)

Synthesis Example 37

Synthesis of Compound 62

Compound 62 was synthesized using Intermediate I-40 and iodobenzene in the synthesis of Intermediate I-1, instead of 2-bromonitrobenzene and 9,9-dimethyl-2-iodofluorene, in the same manner as in the synthesis of Compound 8 in Synthesis Example 1. This compound was identified using MS/FAB. $C_{65}H_{49}N_3$: calc. 871.39. found 871.51

$^1$H NMR (CDCl$_3$, 400 MHz) δ (ppm) 8.12-8.10 (m, 1H), 7.91 (d, 1H), 7.77-7.76 (m, 1H), 7.71-7.69 (m, 2H), 7.63-7.51 (m, 6H), 7.48-7.42 (m, 6H), 7.39-7.34 (m, 2H), 7.08-7.02 (m, 8H), 6.86-6.82 (m, 2H), 6.70-6.63 (m, 6H), 6.16-6.13 (m, 8H), 1.77 (s, 6H)

Synthesis Example 38

Synthesis of Compound 64

Compound 64 was synthesized using Intermediate I-41 and iodobenzene in the synthesis of Intermediate I-1, instead of 2-bromonitrobenzene and 9,9-dimethyl-2-iodofluorene, in the same manner as in the synthesis of Compound 8 in Synthesis Example 1. This compound was identified using MS/FAB. $C_{62}H_{45}N_5$: calc. 859.36. found 859.47

$^1$H NMR (CDCl$_3$, 400 MHz) δ (ppm) 9.07-9.06 (m, 1H), 8.80-8.76 (m, 4H), 8.56-8.54 (m, 1H), 7.95-7.89 (m, 3H), 7.77-7.76 (m, 1H), 7.71-7.70 (m, 1H), 7.63-7.60 (m, 4H), 7.55-7.34 (m, 11H), 7.08-7.03 (m, 5H), 6.69-6.63 (m, 4H), 6.16-6.13 (m, 4H), 1.75 (s, 6H)

Synthesis Example 39

Synthesis of Compound 66

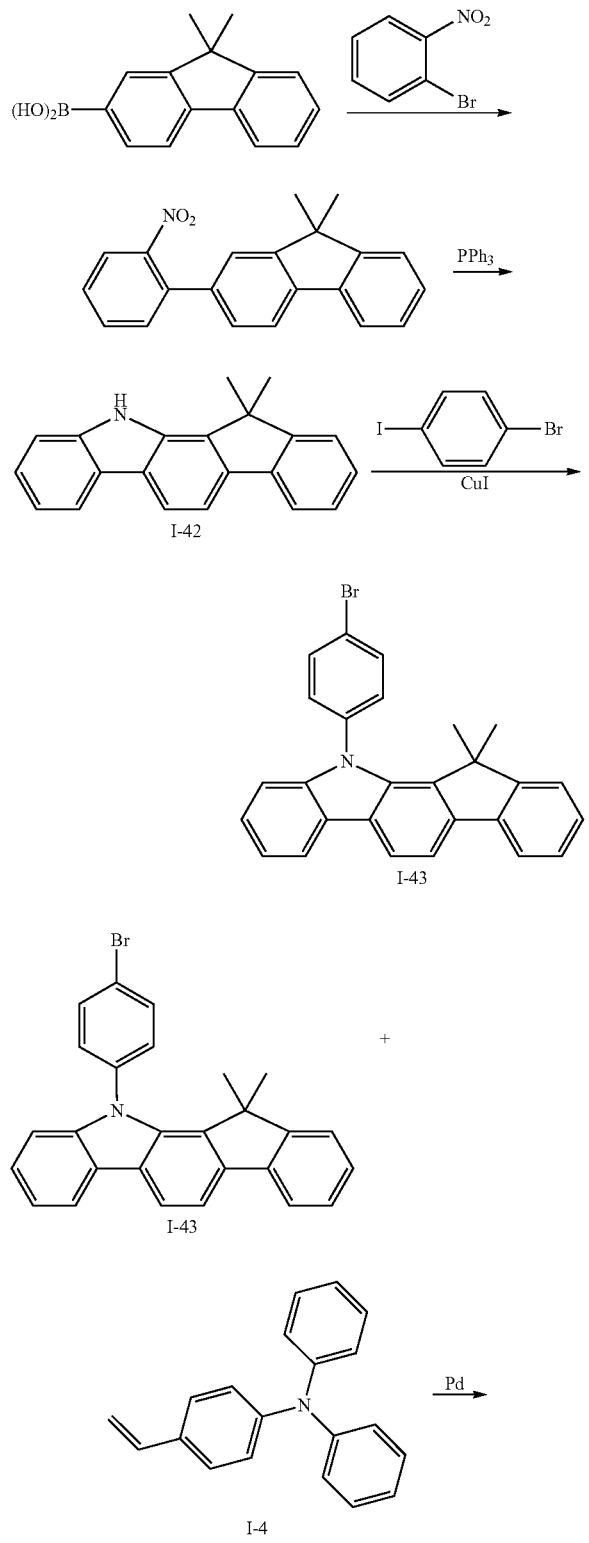

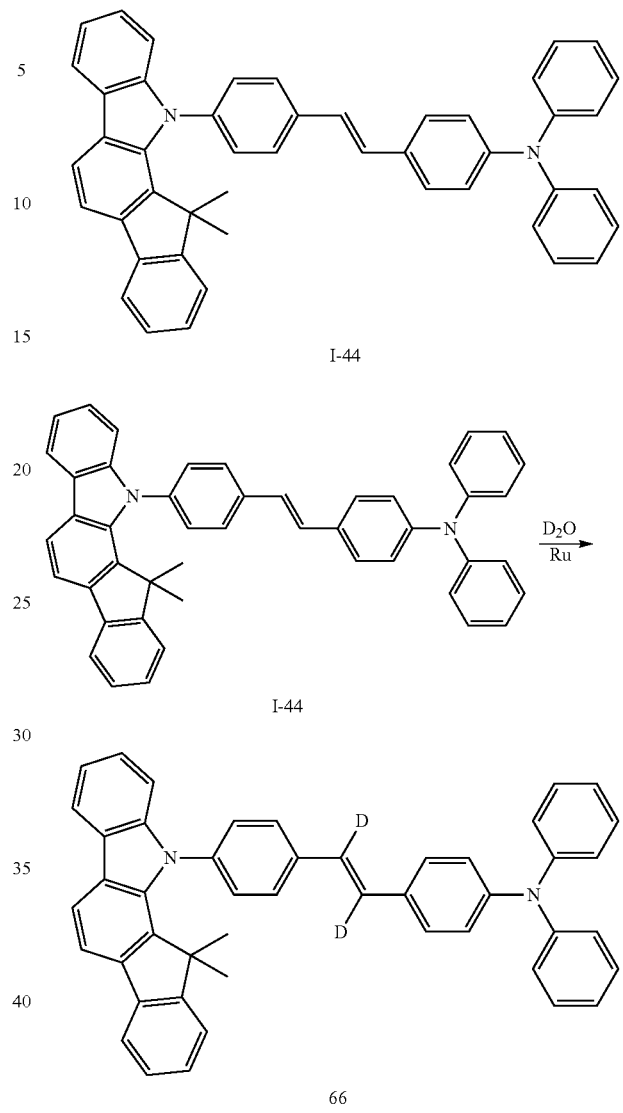

Intermediate I-42, instead of Intermediate I-2, was synthesized using Intermediate 9,9-dimethyl-7-fluoreneboronic acid, instead of 2-bromo-9,9-dimethyl-7-fluoreneboronic acid, in the same manner as in the synthesis of Compound 8 in Synthesis Example 1. Subsequently, Intermediate I-43, instead of Intermediate I-3, was synthesized using 1-bromo-4-iodobenzene, instead of 9,9-dimethyl-2-iodofluorene. Next, Intermediate I-44, instead of Compound 8, was synthesized by reacting Intermediate I-43, instead of Intermediate I-3, with Intermediate I-4.

Compound 66 was synthesized using Intermediate I-44, instead of Intermediate I-6, in the same manner as in the synthesis of Compound 16 in Synthesis Example 2. This compound was identified using MS/FAB.

$C_{47}H_{34}D_2N_2$: calc. 630.30. found 630.41

$^1$H NMR (CDCl$_3$, 400 MHz) δ (ppm) 8.16-8.11 (m, 1H), 7.86-7.84 (m, 1H), 7.77 (d, 1H), 7.72-7.68 (m, 2H), 7.63-7.61 (m, 1H), 7.44-7.40 (m, 4H), 7.35-7.29 (m, 2H), 7.22-7.16 (m, 3H), 7.09-7.03 (m, 5H), 6.69-6.63 (m, 4H), 6.16-6.13 (m, 4H), 1.74 (s, 6H)

Synthesis Example 40

Synthesis of Compound 68

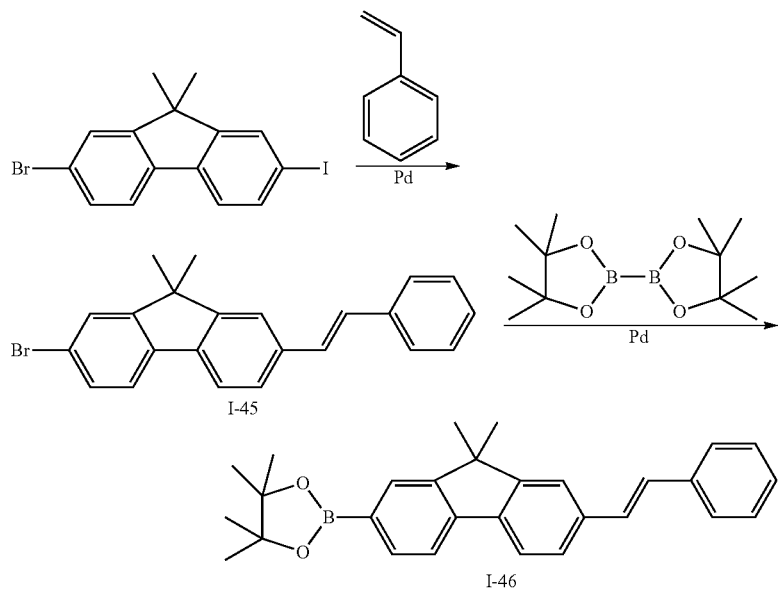

Synthesis of Intermediate I-46

As illustrated in a synthesis flow diagram above, 2-bromo-7-iodo-9,9-dimethyl-9H-fluorene was reacted with styrene to obtain Intermediate I-45, which was then reacted with bis(pinacolato)diborane to obtain Intermediate I-46.

Synthesis of Compound 68

Intermediate 68 was synthesized using Intermediate I-46, instead of 9,9-dimethyl-7-fluoreneboronic acid, in the same manner as in the synthesis of Intermediate I-44 in Synthesis Example 39. This compound was identified using MS/FAB.

$C_{55}H_{42}N_2$: calc. 730.33. found 730.42

$^1$H NMR (CDCl$_3$, 400 MHz) δ (ppm) 8.16-8.11 (m, 1H), 7.93 (d, 1H), 7.77 (d, 1H), 7.73-7.69 (m, 2H), 7.62-7.59 (m, 1H), 7.52-7.46 (m, 2H), 7.45-7.26 (m, 13H), 7.20-7.15 (m, 2H), 7.08-7.03 (m, 5H), 6.70-6.63 (m, 4H), 6.17-6.13 (m, 4H), 1.76 (s, 6H)

Synthesis Example 41

Synthesis of Compound 71

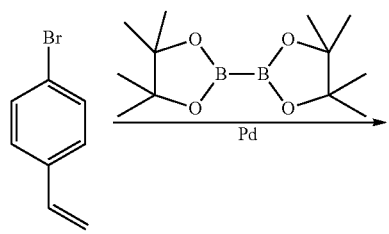

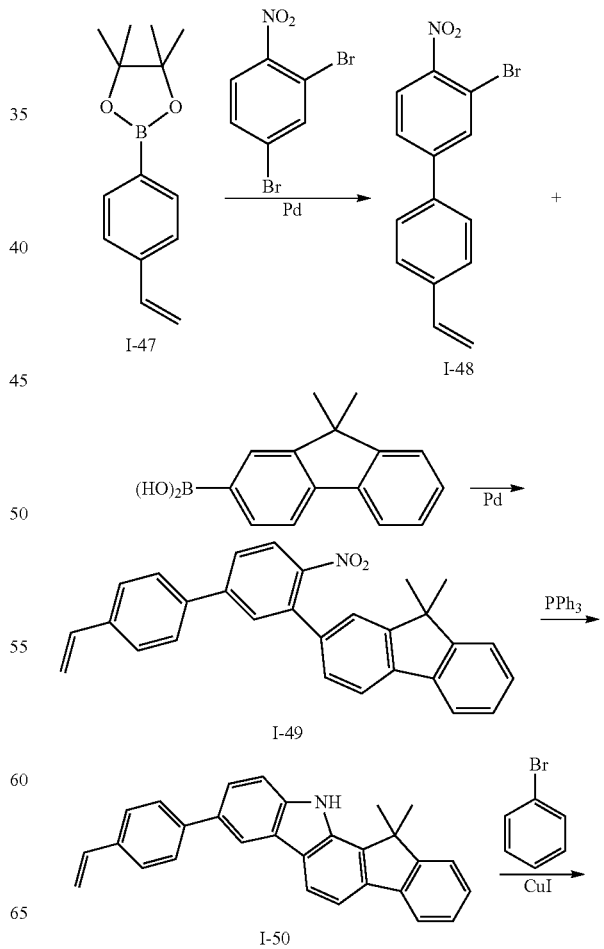

-continued

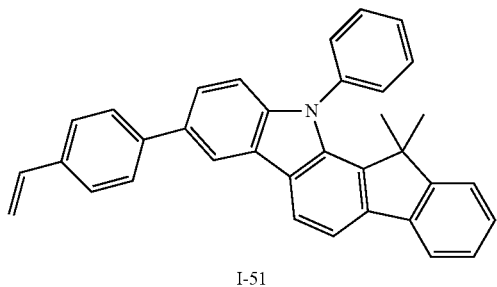
I-51

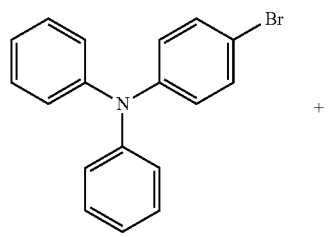

+

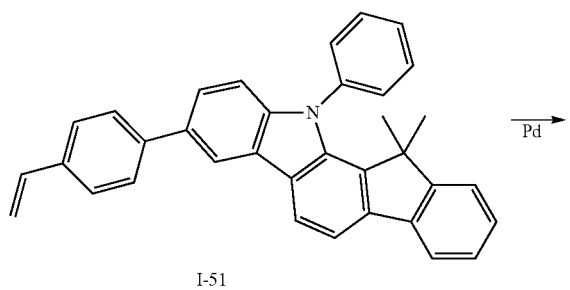
I-51

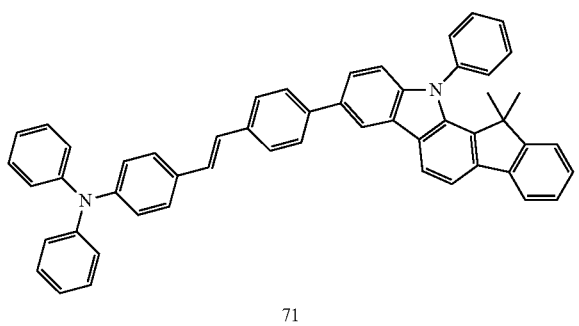
71

Synthesis of Compound I-47

Intermediate I-47 was synthesized using 4-bromostyrene, instead of Intermediate I-14, in the same manner as in the synthesis of Intermediate I-15 in Synthesis Example 5. This compound was identified using MS/FAB. $C_{14}H_{19}BO_2$: calc. 230.14. found 230.25

Synthesis of Compound I-48

Intermediate I-48 was synthesized using Compound I-47 and 2,4-dibromo-1-nitrobenzene, instead of 2-bromo-9,9-dimethyl-7-fluoreneboronic acid and 2-bromonitrobenzene, in the same manner as in the synthesis of Intermediate I-1 in Synthesis Example 1. This compound was identified using MS/FAB. $C_{14}H_{10}BrNO_2$: calc. 302.98. found 303.07

Synthesis of Intermediate I-49

Intermediate I-49 was synthesized using Intermediate 9,9-dimethyl-7-fluoreneboronic acid and Compound I-47, instead of 2-bromo-9,9-dimethyl-7-fluoreneboronic acid and 2-bromonitrobenzene, in the same manner as in the synthesis of Intermediate I-1 in Synthesis Example 1. This compound was identified using MS/FAB. $C_{29}H_{23}NO_2$: calc. 417.17. found 417.25

Synthesis of Intermediate I-50

Intermediate I-50 was synthesized using Intermediate I-49, instead of Intermediate I-1, in the same manner as in the synthesis of Intermediate I-2 in Synthesis Example 1. This compound was identified using MS/FAB. $C_{29}H_{23}N$: calc. 385.18. found 385.24

Synthesis of Intermediate I-51

Intermediate I-51 was synthesized using Intermediate I-50 and bromobenzene, instead of Intermediate I-2 and 9,9-dimethyl-2-iodofluorene, in the same manner as in the synthesis of Intermediate I-3 in Synthesis Example 1. This compound was identified using MS/FAB. $C_{35}H_{27}N$: calc. 461.21. found 461.28

Synthesis of Compound 71

Compound 71 was synthesized using 4-bromotriphenylamine and Intermediate I-51, instead of Intermediates I-3 and I-4, in the same manner as in the synthesis of Compound 8 in Synthesis Example 1. This compound was identified using MS/FAB. $C_{53}H_{40}N_2$: calc. 704.31. found 704.40

$^1$H NMR (CDCl$_3$, 400 MHz) δ (ppm) 8.04-8.01 (m, 1H), 7.85-7.83 (m, 1H), 7.78 (d, 1H), 7.71-7.69 (m, 1H), 7.63-7.60 (m, 4H), 7.56-7.41 (m, 8H), 7.38-7.34 (m, 1H), 7.30-7.26 (m, 1H), 7.22-7.17 (m, 2H), 7.09-7.03 (m, 5H), 6.91-6.87 (m, 1H), 6.70-6.63 (m, 4H), 6.16-6.11 (m, 4H), 1.74 (s, 6H)

Synthesis Example 42

Synthesis of Compound 73

Compound 73 was synthesized using Intermediate I-46 of Synthesis Example in the synthesis of Intermediate I-49, instead of 9,9-dimethyl-7-fluoreneboronic acid, in the same manner as in the synthesis of Compound 71 in Synthesis Example 41. This compound was identified using MS/FAB. $C_{73}H_{55}N_3$: calc. 973.43. found 973.52

$^1$H NMR (CDCl$_3$, 400 MHz) δ (ppm) 8.04-8.01 (m, 1H), 7.91 (d, 1H), 7.77 (d, 1H), 7.71-7.69 (m, 2H), 7.64-7.61 (m, 4H), 7.56-7.51 (m, 2H), 7.49-7.26 (m, 14H), 7.08-7.03 (m, 8H), 6.91-6.87 (m, 1H), 6.70-6.63 (m, 8H), 6.16-6.11 (m, 7H), 1.76 (s, 6H)

Intermediates I-19 and I-44 used in Synthesis Examples 7-42 are represented by the following formulae.

I-19 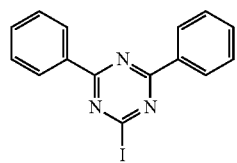
I-20 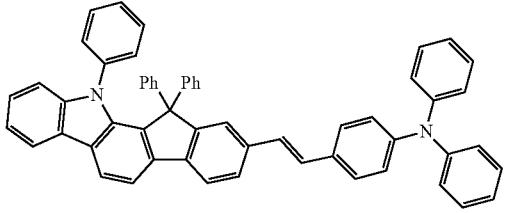
I-21 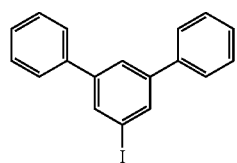
I-22 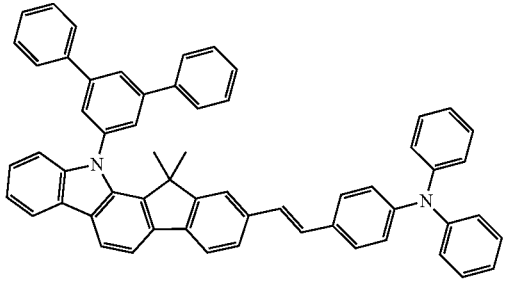
I-23 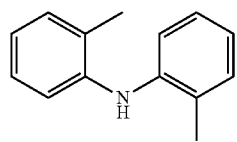
I-24 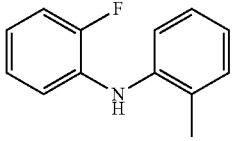
I-25 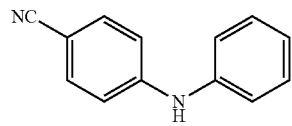
I-26 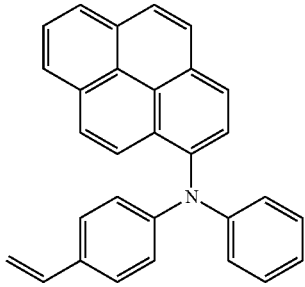
I-27 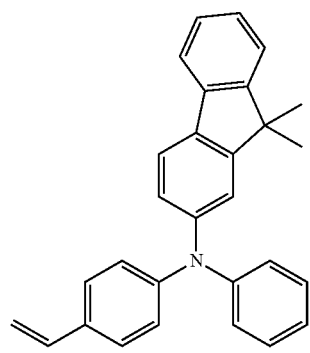
I-28 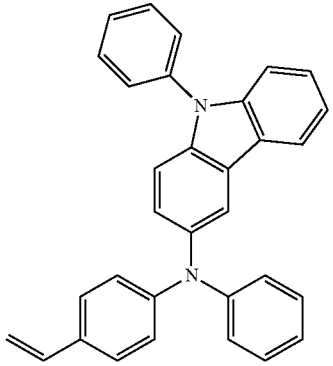

-continued
I-30
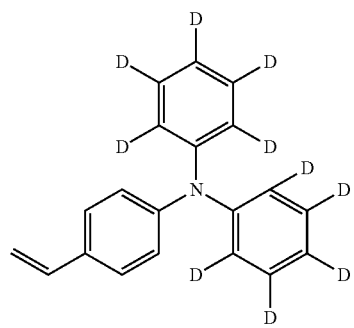
I-31
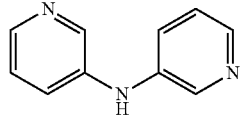
I-32
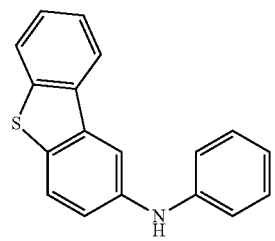
I-33
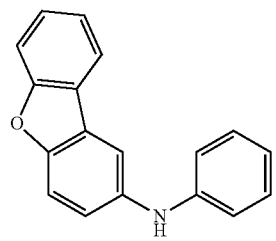
I-34
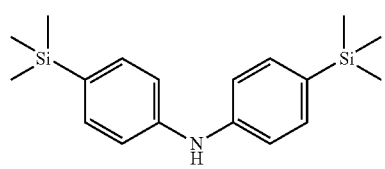
I-35
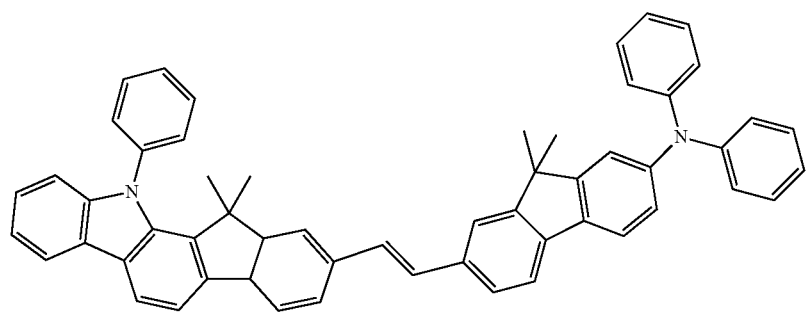
I-36
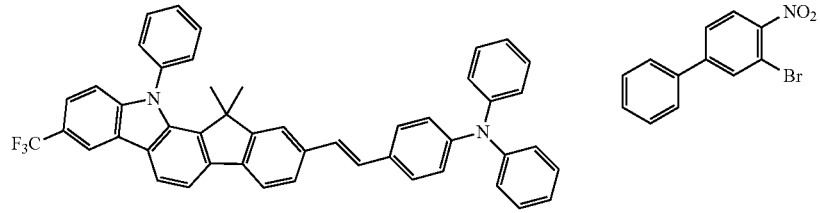
I-37
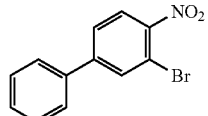
I-38
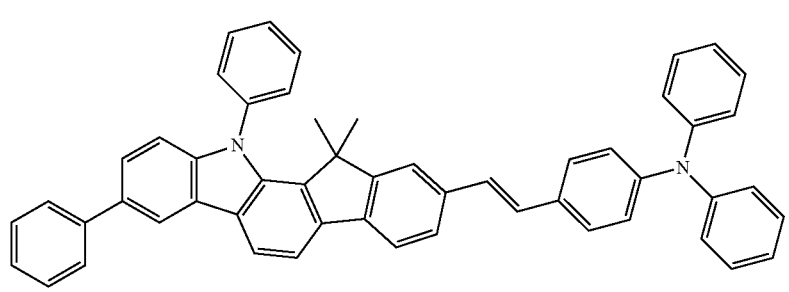

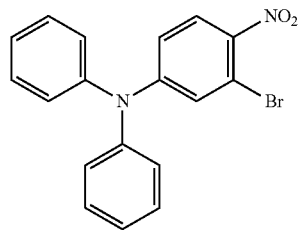

I-39

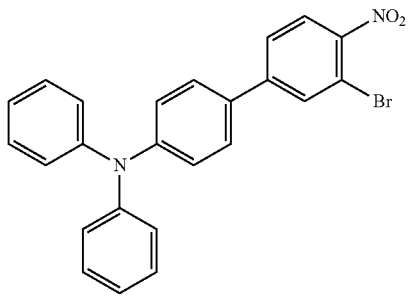

I-40

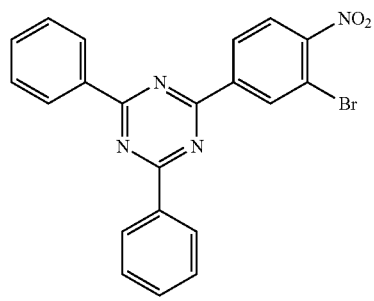

I-41

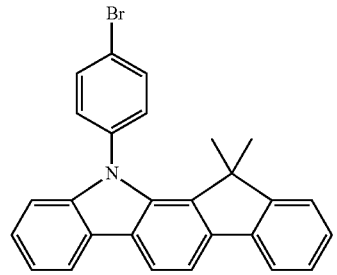

I-43

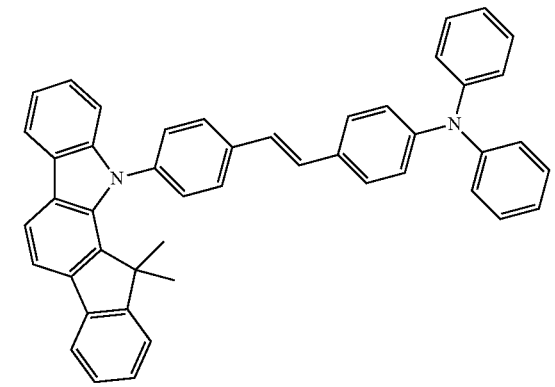

I-44

Example 1

A 15 Ω/cm² (1200 Å) ITO glass substrate (available from Corning Co.) was cut to a size of 50 mm×50 mm×0.7 mm, ultrasonically washed with isopropyl alcohol for 5 minutes and then with pure water for 5 minutes, and washed again with UV ozone for 30 minutes. 2-TNATA was vacuum-deposited on the ITO glass substrate to form an HIL having a thickness of 600 Å on the anode, and then 4,4'-bis[N-(1-naphthyl)-N-phenylamino]biphenyl (NPB) was vacuum-deposited on the HIL to form a HTL having a thickness of 300 Å. 98 wt % of ADN as a blue fluorescent host and 2 wt % of Compound 8 above as a fluorescent dopant were deposited on the HTL to form an EML having a thickness of 300 Å. Alq3 was vacuum-deposited on the EML to form an ETL having a thickness of 300 Å. LiF was vacuum-deposited on the ETL to form an EIL having a thickness of 10 Å and Al was vacuum-deposited on the EIL to form a cathode having a thickness of 3,000 Å, thereby completing the manufacture of an organic light-emitting device.

Example 2

An organic light-emitting device was manufactured in the same manner as in Example 1, except that Compound 16, instead of Compound 8, was used as a dopant to form the EML.

Example 3

An organic light-emitting device was manufactured in the same manner as in Example 1, except that Compound 19, instead of Compound 8, was used as a dopant to form the EML.

Example 4

An organic light-emitting device was manufactured in the same manner as in Example 1, except that Compound 25, instead of Compound 8, was used as a dopant to form the EML.

Example 5

An organic light-emitting device was manufactured in the same manner as in Example 1, except that Compound 29, instead of Compound 8, was used as a dopant to form the EML.

Example 6

An organic light-emitting device was manufactured in the same manner as in Example 1, except that Compound 39, instead of Compound 8, was used as a dopant to form the EML.

Example 7

An organic light-emitting device was manufactured in the same manner as in Example 1, except that Compound 47, instead of Compound 8, was used as a dopant to form the EML.

Example 8

An organic light-emitting device was manufactured in the same manner as in Example 1, except that Compound 56, instead of Compound 8, was used as a dopant to form the EML.

Example 9

An organic light-emitting device was manufactured in the same manner as in Example 1, except that Compound 62, instead of Compound 8, was used as a dopant to form the EML.

Comparative Example 1

An organic light-emitting device was manufactured in the same manner as in Example 1, except that DPAVBi, instead of Compound 8, was used as a dopant to form the EML.

Evaluation Example

Driving voltages, current densities, luminance, efficiencies, emitting-light colors, half-life spans of the organic light-emitting devices of Examples 1 to 9 and Comparative Example 1 were measured using a PR650 (Spectroscan) Source Measurement Unit. (available from Photo Research, Inc.). The results are shown in Table 1 below.

Referring to Table 2, the organic light-emitting devices of Examples 1 to 9 were found to have better performance in terms of driving voltage, luminance, efficiency, and lifetime, as compared with the organic light-emitting device of Comparative Example 1.

As described above, an organic light-emitting device including the heterocyclic compound according to embodiments of the present invention may have a high performance, for example, a low driving voltage, a high luminance, a high efficiency, and a long lifetime.

While the present invention has been particularly shown and described with reference to exemplary embodiments thereof, it will be understood by those of ordinary skill in the art that various changes in form and details may be made therein without departing from the spirit and scope of the present invention as defined by the following claims

What is claimed is:

1. A heterocyclic compound represented by Formula 1A below:

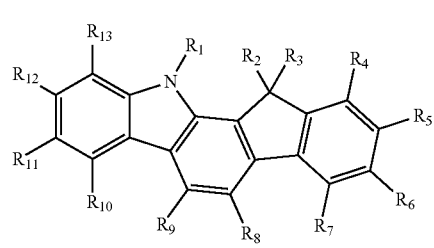

[Formula 1A]

wherein, in Formula 1A, $R_1$ to $R_{13}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, a substituted or unsubstituted $C_5$-$C_{30}$ arylthio group, a —N($Q_1$)($Q_2$) group, and a group represented by Formula 1B below,

TABLE 1

| | EML host | EML dopant | Driving voltage (V) | Current Density | Luminance (cd/m$^2$) | Efficiency (cd/A) | Luminescent Color | Half-life span (hr @100 mA) |
|---|---|---|---|---|---|---|---|---|
| Example 1 | ADN | Compound 8 | 6.22 | 50 | 3,132 | 6.26 | blue | 251 |
| Example 2 | ADN | Compound 16 | 6.27 | 50 | 3,055 | 6.11 | blue | 315 |
| Example 3 | ADN | Compound 19 | 6.20 | 50 | 3,065 | 6.13 | blue | 264 |
| Example 4 | ADN | Compound 25 | 6.27 | 50 | 3,185 | 6.37 | blue | 298 |
| Example 5 | ADN | Compound 29 | 6.26 | 50 | 2,985 | 5.97 | blue | 253 |
| Example 6 | ADN | Compound 39 | 6.29 | 50 | 3,115 | 6.23 | bluish green | 241 |
| Example 7 | ADN | Compound 47 | 6.18 | 50 | 3,019 | 6.03 | bluish green | 263 |
| Example 8 | ADN | Compound 56 | 6.20 | 50 | 3,022 | 6.04 | bluish green | 244 |
| Example 9 | ADN | Compound 62 | 6.23 | 50 | 3,215 | 6.43 | bluish green | 249 |
| Comparative Example 1 | ADN | DPAVBi | 7.85 | 50 | 2,065 | 4.13 | blue | 145 |

[1] A half life-span at a current density of 100 mA/cm$^2$ wherein $Q_1$ and $Q_2$ are each independently one of a hydrogen atom, a deuterium atom, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_6$-$C_{30}$ aryl group, a substituted or unsubstituted $C_6$-$C_{30}$ aryloxy group, a substituted or unsubstituted $C_6$-$C_{30}$ arylthio group, and a substituted or unsubstituted $C_3$-$C_{30}$ heteroaryl group:

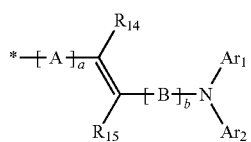

Formula 1B wherein, in Formula 1B, $R_{14}$ and $R_{15}$ are each independently one of a hydrogen atom, a deuterium atom, a halogen atom, a hydroxyl group, a cyano group, a nitro group, a carboxyl group, a substituted or unsubstituted $C_1$-$C_{30}$ alkyl group, a substituted or unsubstituted $C_2$-$C_{30}$ alkenyl group, a substituted or unsubstituted $C_2$-$C_{30}$ alkynyl group, a substituted or unsubstituted $C_1$-$C_{30}$ alkoxy group, a substituted or unsubstituted $C_3$-$C_{30}$ cycloalkyl group, a substituted or unsubstituted $C_3$-$C_{30}$ cycloalkenyl group, a substituted or unsubstituted $C_5$-$C_{30}$ aryl group, a substituted or unsubstituted $C_2$-$C_{30}$ heteroaryl group, a substituted or unsubstituted $C_5$-$C_{30}$ aryloxy group, and a substituted or unsubstituted $C_5$-$C_{30}$ arylthio group;

at least one of $R_1$ to $R_{13}$ is a group represented by Formula 1B above;

$Ar_1$ and $Ar_2$ are each independently a substituted or unsubstituted $C_5$-$C_{30}$ aryl group or a substituted or unsubstituted $C_3$-$C_{30}$ heteroaryl group, wherein $Ar_1$ and $Ar_2$ are optionally linked to each other;

A and B are a divalent linker, and are each independently one of a substituted or unsubstituted $C_5$-$C_{30}$ arylene group or a substituted or unsubstituted $C_3$-$C_{30}$ heteroarylene group; and a is an integer from 0 to 3, and b is an integer from 0 to 3, wherein if a is 2 or greater, the two or more A are identical to or different from each other, and if b is 2 or greater, the two or more B are identical to or different from each other.

2. The heterocyclic compound of claim 1, wherein $Ar_1$ and $Ar_2$ are each independently one of a substituted or unsubstituted phenyl group, a substituted or unsubstituted biphenyl group, a substituted or unsubstituted terphenyl group, a substituted or unsubstituted naphthyl group, a substituted or unsubstituted phenoxy group, a substituted or unsubstituted fluorenyl group, a substituted or unsubstituted spiro-fluorenyl group, a substituted or unsubstituted carbozolyl group, a substituted or unsubstituted phenanthrenyl group, a substituted or unsubstituted pyranyl group, a substituted or unsubstituted pyridinyl group, a substituted or unsubstituted pyrimidinyl group, a substituted or unsubstituted diazinyl group, a substituted or unsubstituted triazinyl group, a substituted or unsubstituted quinolinyl group, a substituted or unsubstituted benzoimidazolyl group, a substituted or unsubstituted benzoxazolyl group, a substituted or unsubstituted pentalenyl group, a substituted or unsubstituted indenyl group, a substituted or unsubstituted azulenyl group, a substituted or unsubstituted heptalenyl group, a substituted or unsubstituted indacenyl group, a substituted or unsubstituted acenaphthyl group, a substituted or unsubstituted phenalenyl group, a substituted or unsubstituted phenanthridinyl group, a substituted or unsubstituted anthryl group, a substituted or unsubstituted fluoranthenyl group, a substituted or unsubstituted triphenylenyl group, a substituted or unsubstituted pyrenyl group, a substituted or unsubstituted chrysenyl group, a substituted or unsubstituted naphthacenyl group, a substituted or unsubstituted picenyl group, a substituted or unsubstituted perylenyl group, a substituted or unsubstituted pentaphenyl group, a substituted or unsubstituted hexacenyl group, a substituted or unsubstituted pyrrolyl group, a substituted or unsubstituted imidazolinyl group, a substituted or unsubstituted pyrazolyl group, a substituted or unsubstituted imidazopyridinyl group, a substituted or unsubstituted pyrazinyl group, a substituted or unsubstituted imidazopyrimidinyl group, a substituted or unsubstituted pyridazinyl group, a substituted or unsubstituted indolyl group, a substituted or unsubstituted indolizinyl group, a substituted or unsubstituted isoindolyl group, a substituted or unsubstituted pyridoindolyl group, a substituted or unsubstituted indazolyl group, a substituted or unsubstituted carbazolyl group, a substituted or unsubstituted purinyl group, a substituted or unsubstituted benzoquinolinyl group, a substituted or unsubstituted phthalazinyl group, a substituted or unsubstituted naphthyridinyl group, a substituted or unsubstituted quinoxalinyl group, a substituted or unsubstituted quinazolinyl group, a substituted or unsubstituted cinnolinyl group, a substituted or unsubstituted phenazinyl group, a substituted or unsubstituted furanyl group, a substituted or unsubstituted benzofuranyl group, a substituted or unsubstituted dibenzofuranyl group, a substituted or unsubstituted thiophenyl group, a substituted or unsubstituted benzothiophenyl group, a substituted or unsubstituted dibenzothiophenyl group, a substituted or unsubstituted thiazolyl group, a substituted or unsubstituted isothiazolyl group, a substituted or unsubstituted benzothiazolyl group, a substituted or unsubstituted oxazolyl group, a substituted or unsubstituted isoxazolyl group, a substituted or unsubstituted oxadiazolyl group, a substituted or unsubstituted triazolyl group, and a substituted or unsubstituted tetrazolyl group.

3. The heterocyclic compound of claim 1, wherein $Ar_1$ and $Ar_2$ are each independently one of the groups represented by Formulae 2A to 2J below;

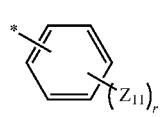

Formula 2A

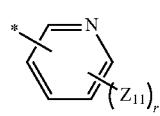

Formula 2B

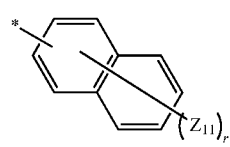

Formula 2C

-continued

Formula 2D
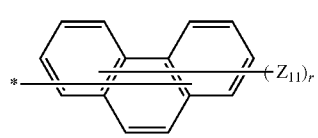

Formula 2E
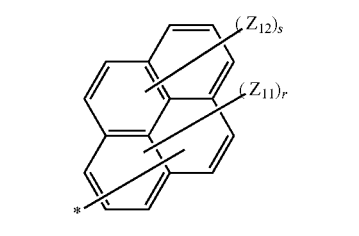

Formula 2F
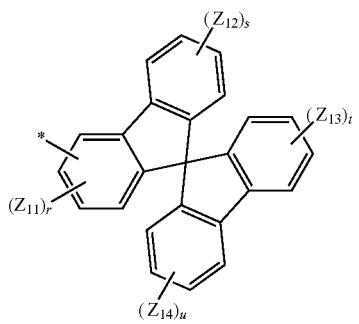

Formula 2G
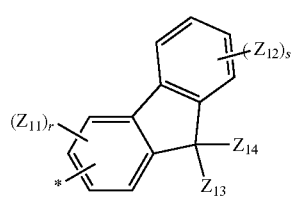

Formula 2H
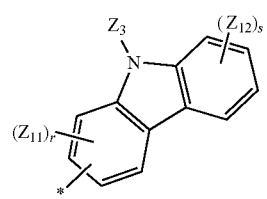

Formula 2I
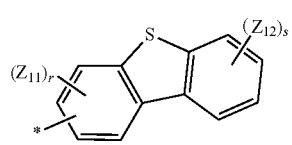

Formula 2J
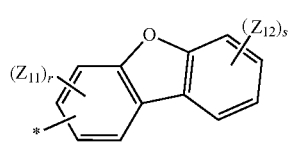

wherein, in Formulae 2A to 2J, $Z_{11}$, $Z_{12}$, $Z_{13}$, and $Z_{14}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolyl group;

a plurality of $Z_{11}$, $Z_{12}$, $Z_{13}$, and $Z_{14}$ are identical to or different from each other;

r, is an integer from 1 to 9;

s is an integer from 1 to 5;

t is an integer from 1 to 4;

u is an integer from 1 to 4; and

* indicates a binding site.

4. The heterocyclic compound of claim 3, wherein $Ar_1$ and $Ar_2$ are each independently one of the groups represented by Formulae 3A to 3S below:

Formula 3A
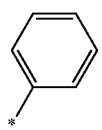

Formula 3B
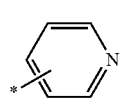

Formula 3C
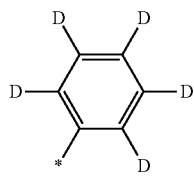

Formula 3D
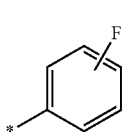

Formula 3E
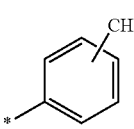

Formula 3F
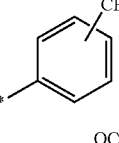

Formula 3G
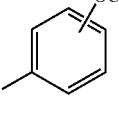

Formula 3H
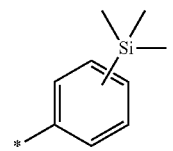

Formula 3I
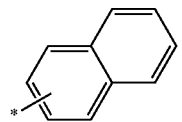

101
-continued

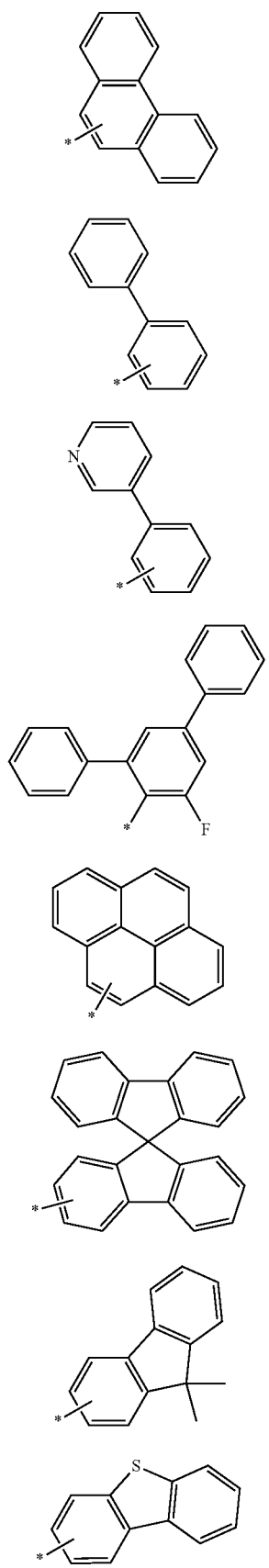

102
-continued

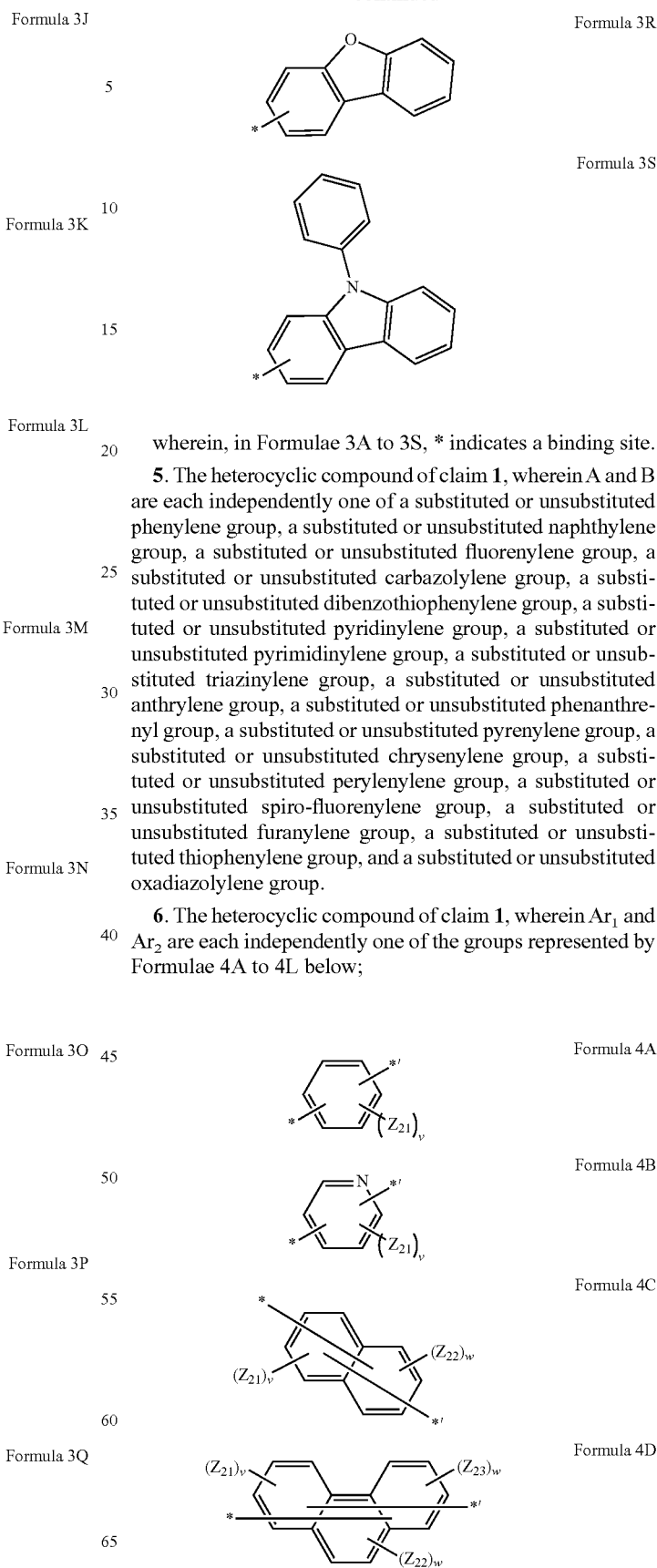

wherein, in Formulae 3A to 3S, * indicates a binding site.

5. The heterocyclic compound of claim 1, wherein A and B are each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group.

6. The heterocyclic compound of claim 1, wherein $Ar_1$ and $Ar_2$ are each independently one of the groups represented by Formulae 4A to 4L below;

-continued

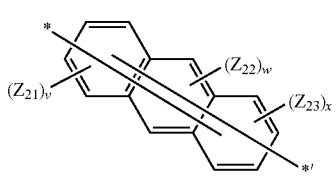
Formula 4E

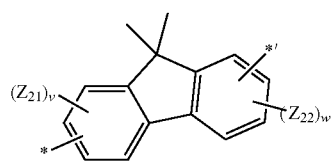
Formula 4F

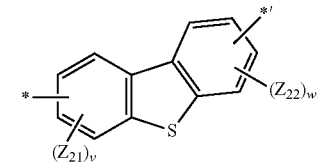
Formula 4G

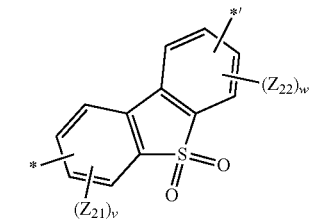
Formula 4H

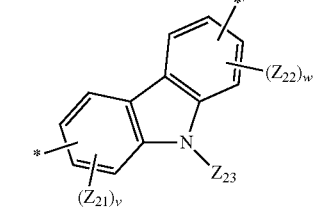
Formula 4I

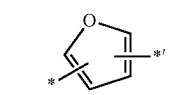
Formula 4J

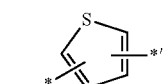
Formula 4K

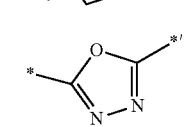
Formula 4L wherein, in Formulae 4A to 4L, $Z_{21}$, $Z_{22}$, and $Z_{23}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, and a substituted or unsubstituted pyridinyl group, wherein a plurality of $Z_{21}$, $Z_{22}$, and $Z_{23}$ are identical to or different from each other;

v, w, and x are an integer from 1 to 4; and

* and *' indicate binding sites.

7. The heterocyclic compound of claim 6, wherein A and B are each independently one of the groups represented by Formulae 5A to 5R below:

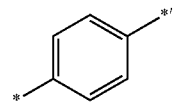
Formula 5A

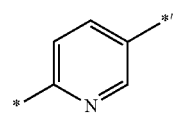
Formula 5B

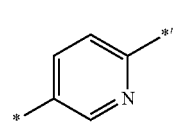
Formula 5C

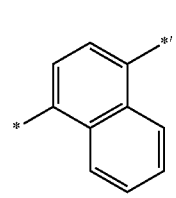
Formula 5D

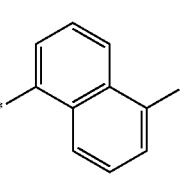
Formula 5E

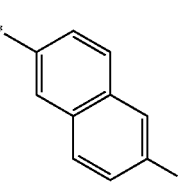
Formula 5F

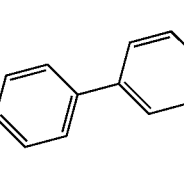
Formula 5G

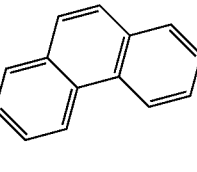
Formula 5H

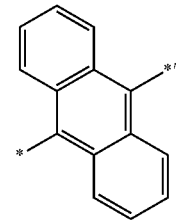
Formula 5I

105
-continued

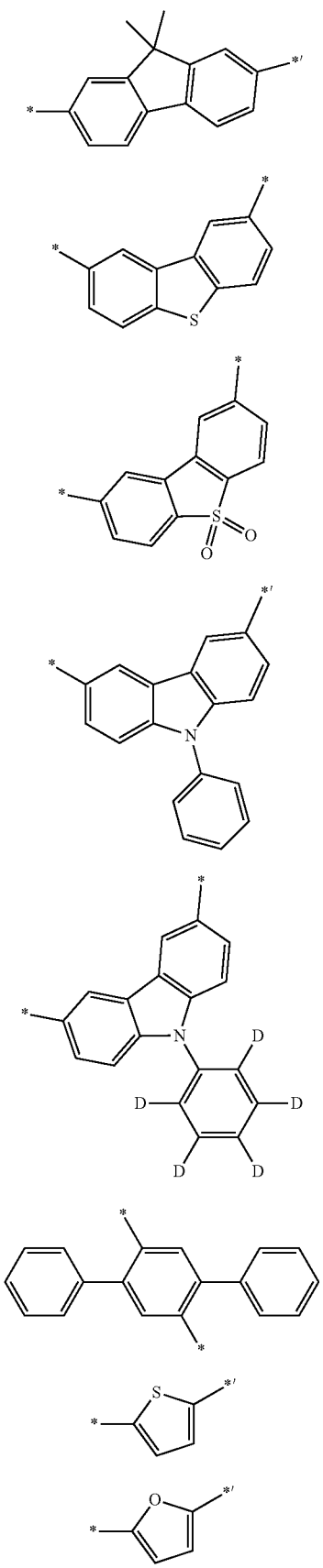

Formula 5J

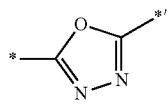

Formula 5K

Formula 5L

Formula 5M

Formula 5N

Formula 5O

Formula 5P

Formula 5Q

106
-continued

Formula 5R wherein, in Formulae 5A to 5R, * and *' indicate binding sites.

8. The heterocyclic compound of claim 1, wherein $R_1$ to $R_{13}$ are each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted carbazolyl group, a substituted or unsubstituted pyranyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolinyl group, a substituted or unsubstituted benzoimidazolyl group, a substituted or unsubstituted benzooxazolyl group, a substituted or unsubstituted pentalenyl group, a substituted or unsubstituted indenyl group, a substituted or unsubstituted pyrrolyl group, a substituted or unsubstituted imidazolyl group, a substituted or unsubstituted pyrazolyl group, a $N(Q_1)(Q_2)$ group, and a group represented by Formula 1B below, wherein $Q_1$ and $Q_2$ are each independently one of a hydrogen atom, a deuterium atom, a halogen atom, a hydroxyl group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group:

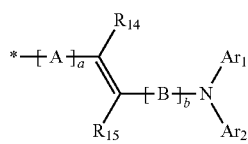

Formula 1B $R_{14}$ and $R_{15}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted naphthyl group, a substituted or unsubstituted anthryl group, and a substituted or unsubstituted pyridinyl group, and a substituted or unsubstituted phenanthrenyl group;

Ar₁ and Ar₂ are each independently one of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, a substituted or unsubstituted spiro-fluorenyl group, and a substituted or unsubstituted oxadiazolyl group;

A and B are each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group; and a is an integer from 0 to 2, and b is an integer from 0 to 2, wherein if a is, the two A are identical to or different from each other, and if b is 2, the two B are identical to or different from each other.

9. The heterocyclic compound of claim 8, wherein $R_1$ to $R_{13}$ are each independently one of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, a group represented by Formula 1B above, and groups represented by Formulae 6A to 6L below; and $R_{14}$ and $R_{15}$ are each independently one of a hydrogen atom, a deuterium atom, and groups represented by Formulae 6A to 6L below:

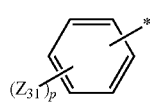

Formula 6A

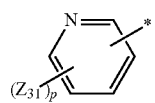

Formula 6B

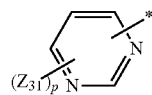

Formula 6C

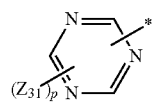

Formula 6D

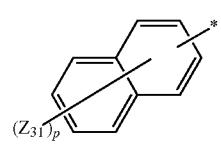

Formula 6E

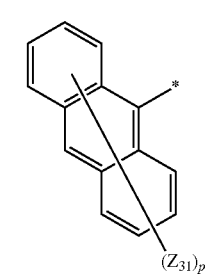

Formula 6F

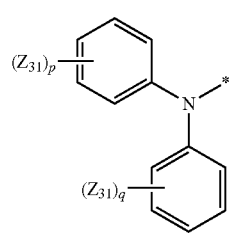

Formula 6G

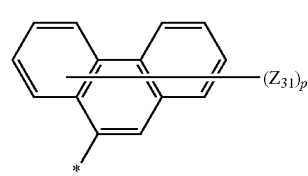

Formula 6H

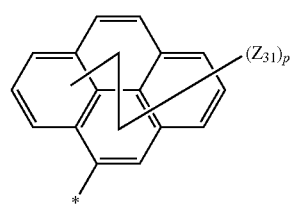

Formula 6I

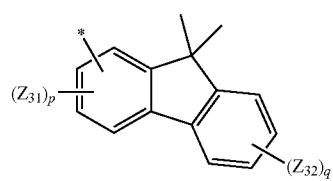

Formula 6J

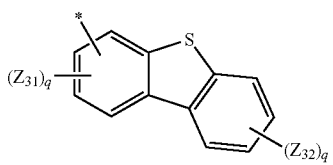

Formula 6K

Formula 6L

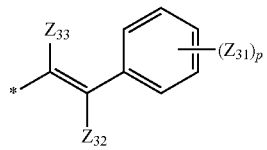

wherein, in Formulae 6A to 6L, $Z_{31}$, $Z_{32}$, and $Z_{33}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted carbazolyl group, a substituted or unsubstituted quinolyl group, and a $N(Q_{11})(Q_{12})$ group;

$Q_{11}$ and $Q_{12}$ are each independently one of a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group;

a plurality of $Z_{31}$ and $Z_{32}$ are identical to or different from each other;

p is an integer from 1 to 9;

q is an integer from 1 to 5; and

* indicates a binding site.

10. The heterocyclic compound of claim 8, wherein $R_1$ to $R_{13}$ are each independently one of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, a cyano group, $-CD_3$, $-CF_3$, a group represented by Formula 1B above, and groups represented by Formulae 7A to 7S below; and $R_{14}$ and $R_{15}$ are each independently one of a hydrogen atom, a deuterium atom, and groups represented by Formulae 7A to 7H below:

Formula 7A

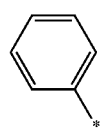

Formula 7B

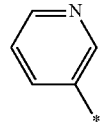

Formula 7C

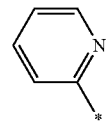

Formula 7D

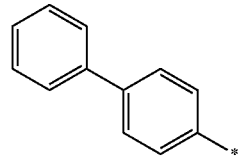

Formula 7E

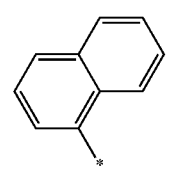

Formula 7F

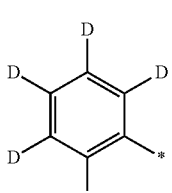

Formula 7G

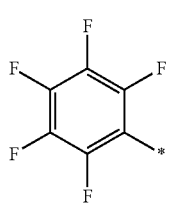

Formula 7H

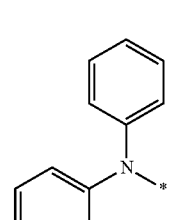

Formula 7I

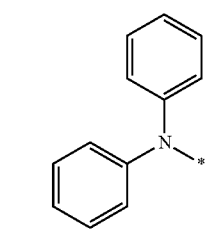

Formula 7J

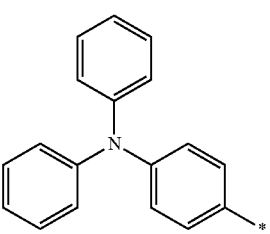

-continued

Formula 7K
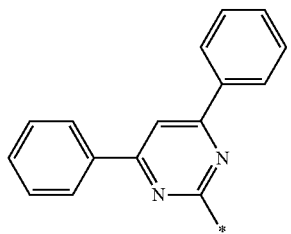

Formula 7L
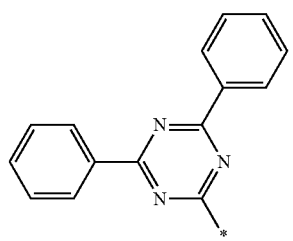

Formula 7M
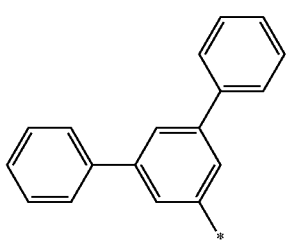

Formula 7N
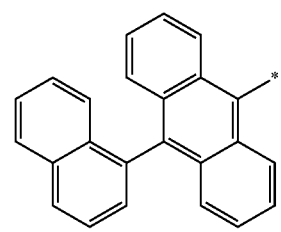

Formula 7O
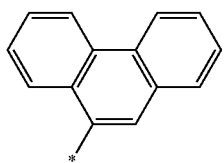

Formula 7P
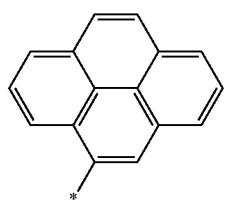

Formula 7Q
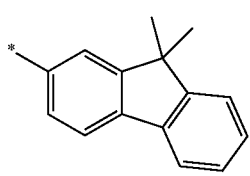

-continued

Formula 7R
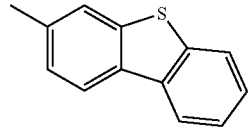

Formula 7S
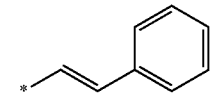

wherein, in Formulae 7A to 7S, * indicates a binding site.

11. A heterocyclic compound represented by Formula 1C, 1D, or 1E below:

Formula 1C

Formula 1D

Formula 1E wherein, in Formula 1C, 1D, and 1E, $R_1$ to $R_{13}$ are each independently one of a hydrogen atom, a deuterium atom, a halogen atom, a hydroxyl group, a cyano group, a nitro group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted biphenyl group, a substituted or unsubstituted terphenyl group, a substituted or unsubstituted naphthyl group, a substituted or unsubstituted anthryl group, a substituted or unsubstituted phenanthrenyl group, a substituted or unsubstituted fluorenyl group, a substituted or unsubstituted carbazolyl group, a substituted or unsubstituted pyranyl group, a substituted or unsubstituted pyridinyl group, a substituted or unsubstituted pyrimidinyl group, a substituted or unsubstituted pyrazinyl group, a substituted or unsubstituted pyridazinyl group, a substituted or unsubstituted triazinyl group, a substituted or unsubstituted quinolinyl group, a substituted or unsubstituted benzoimidazolyl group, a substituted or unsubstituted benzooxazolyl group, a substituted or unsubstituted pentalenyl group, a substituted or unsubstituted indenyl group, a substituted or unsubstituted pyrrolyl group, a substituted or unsubstituted imidazolyl group, a substituted or unsubstituted pyrazolyl group, and a $N(Q_1)(Q_2)$ group, wherein $Q_1$ and $Q_2$ are each independently one of a hydrogen atom, a deuterium atom, a halogen atom, a hydroxyl group, a carboxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group;

$R_{14}$ and $R_{15}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted ethenyl group, a substituted or unsubstituted phenyl group, a substituted or unsubstituted naphthyl group, a substituted or unsubstituted anthryl group, and a substituted or unsubstituted pyridinyl group, and a substituted or unsubstituted phenanthrenyl group;

$Ar_1$ and $Ar_2$ are each independently one of a substituted or unsubstituted phenyl group, a substituted or unsubstituted terphenyl group, a substituted or unsubstituted naphthyl group, a substituted or unsubstituted phenanthrenyl group, a substituted or unsubstituted pyrenyl group, a substituted or unsubstituted anthryl group, a substituted or unsubstituted fluorenyl group, a substituted or unsubstituted spiro-fluorenyl group, a substituted or unsubstituted dibenzothiophenyl group, a substituted or unsubstituted dibenzofuranyl group, a substituted or unsubstituted carbazolyl group, a substituted or unsubstituted pyridinyl group, a substituted or unsubstituted pyrimidinyl group, a substituted or unsubstituted triazinyl group, a substituted or unsubstituted chrysenyl group, a substituted or unsubstituted perylenyl group, a substituted or unsubstituted spiro-fluorenyl group, and a substituted or unsubstituted oxadiazolyl group;

A and B are each independently one of a substituted or unsubstituted phenylene group, a substituted or unsubstituted naphthylene group, a substituted or unsubstituted fluorenylene group, a substituted or unsubstituted carbazolylene group, a substituted or unsubstituted dibenzothiophenylene group, a substituted or unsubstituted pyridinylene group, a substituted or unsubstituted pyrimidinylene group, a substituted or unsubstituted triazinylene group, a substituted or unsubstituted anthrylene group, a substituted or unsubstituted phenanthrenyl group, a substituted or unsubstituted pyrenylene group, a substituted or unsubstituted chrysenylene group, a substituted or unsubstituted perylenylene group, a substituted or unsubstituted spiro-fluorenylene group, a substituted or unsubstituted furanylene group, a substituted or unsubstituted thiophenylene group, and a substituted or unsubstituted oxadiazolylene group; and a is an integer from 0 to 2, and b is an integer from 0 to 2, wherein if a is 2, the two A are identical to or different from each other, and if b is 2, the two B are identical to or different from each other.

12. The heterocyclic compound of claim 11, wherein $Ar_1$ and $Ar_2$ are each independently one of the groups represented by Formulae 2A to 2J below:

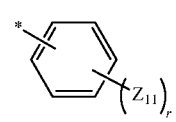

Formula 2A

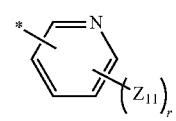

Formula 2B

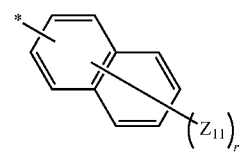

Formula 2C

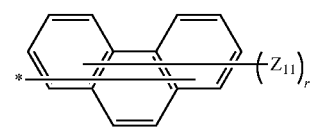

Formula 2D

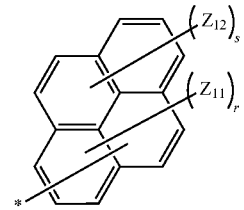

Formula 2E

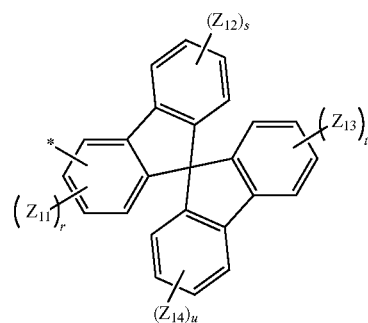

Formula 2F

Formula 2G
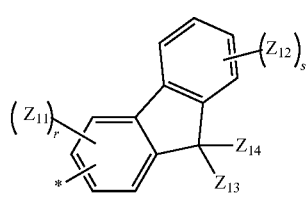

Formula 2H
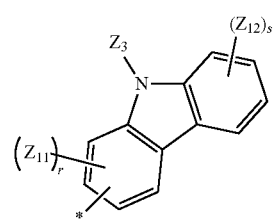

Formula 2I
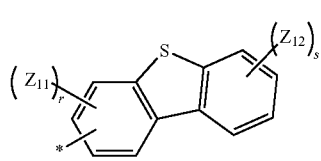

Formula 2J
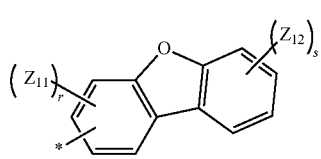

wherein, in Formulae 2A to 2J, $Z_{11}$, $Z_{12}$, $Z_{13}$, and $Z_{14}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, a substituted or unsubstituted anthryl group, a substituted or unsubstituted pyridinyl group, and a substituted or unsubstituted quinolyl group;

a plurality of $Z_{11}$, $Z_{12}$, $Z_{13}$, and $Z_{14}$ are identical to or different from each other;

r is an integer from 1 to 9;

s, t and u are an integer from 1 to 4; and

* indicates a binding site.

13. The heterocyclic compound of claim 11, wherein $Ar_1$ and $Ar_2$ are each independently one of the groups represented by Formulae 3A to 3S below:

Formula 3A
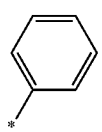

Formula 3B

Formula 3C
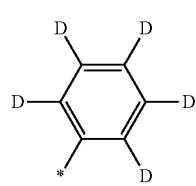

Formula 3D
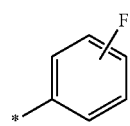

Formula 3E
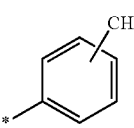

Formula 3F
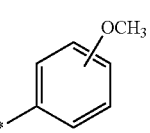

Formula 3G
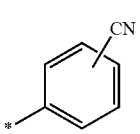

Formula 3H
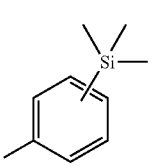

Formula 3I
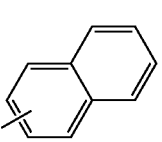

Formula 3J
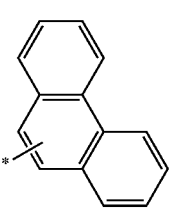

Formula 3K
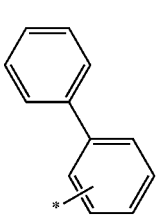

Formula 3L
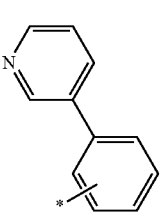

-continued
Formula 3M
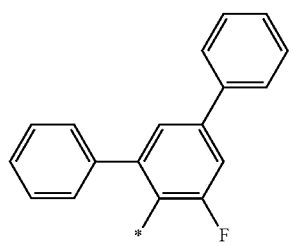
Formula 3N
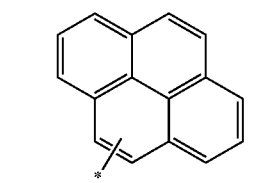
Formula 3O
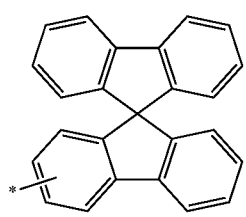
Formula 3P
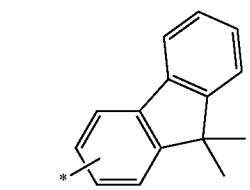
Formula 3Q
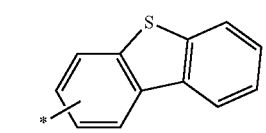
Formula 3R
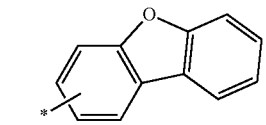
Formula 3S
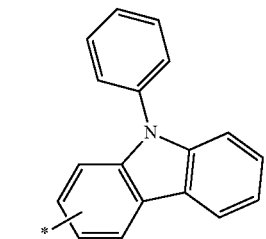
wherein, in Formulae 3A to 3S, * indicates a binding site.
14. The heterocyclic compound of claim 11, wherein A and B are each independently one of the groups represented by Formulae 4A to 4L below:
Formula 4A
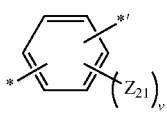
Formula 4B
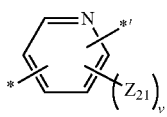
Formula 4C
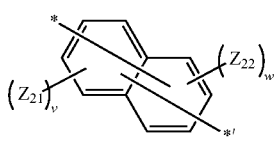
Formula 4D
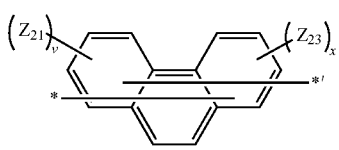
Formula 4E
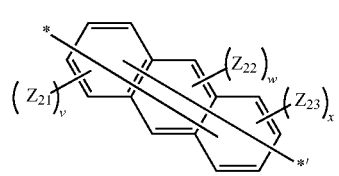
Formula 4F
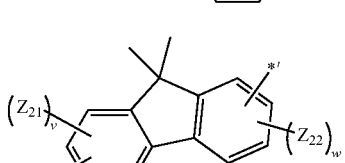
Formula 4G
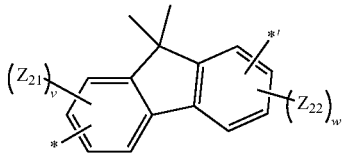
Formula 4H
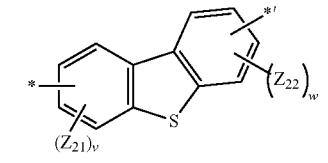
Formula 4I
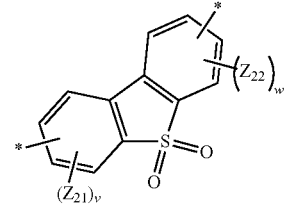
Formula 4J
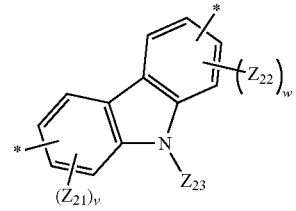

-continued

Formula 4K

Formula 4L
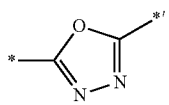

wherein, in Formulae 4A to 4L, $Z_{21}$, $Z_{22}$, and $Z_{23}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted phenyl group, a substituted or unsubstituted naphthyl group, and a substituted or unsubstituted pyridinyl group, wherein a plurality of $Z_{21}$, $Z_{22}$, and $Z_{23}$ are identical to or different from each other;

v, w, and x are an integer from 1 to 4; and

* and *' indicate binding sites.

15. The heterocyclic compound of claim 11, wherein A and B are each independently one of the groups represented by Formulae 5A to 5R below:

Formula 5A
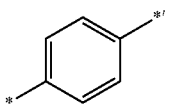

Formula 5B
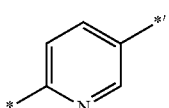

Formula 5C
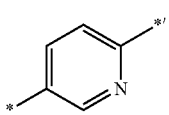

Formula 5D
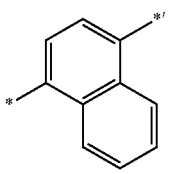

Formula 5E
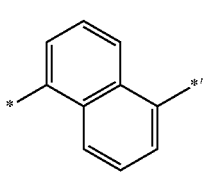

-continued

Formula 5F
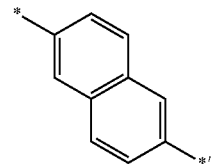

Formula 5G
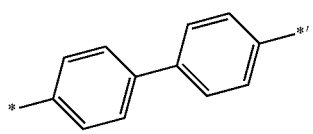

Formula 5H
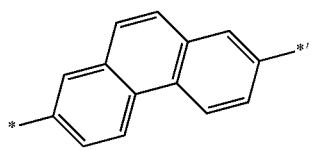

Formula 5I
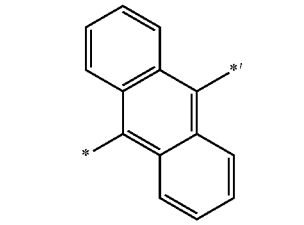

Formula 5J
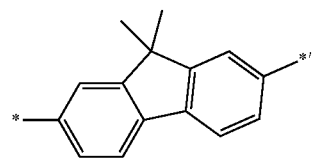

Formula 5K
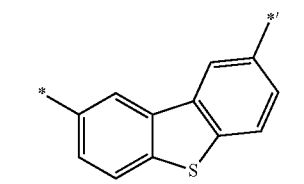

Formula 5L
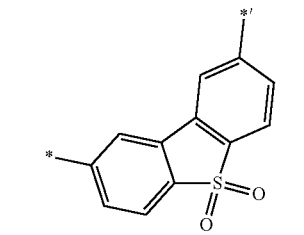

Formula 5M
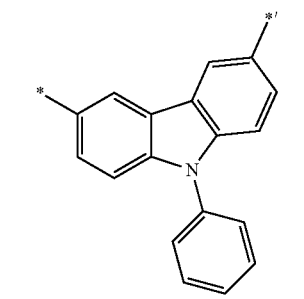

Formula 5N

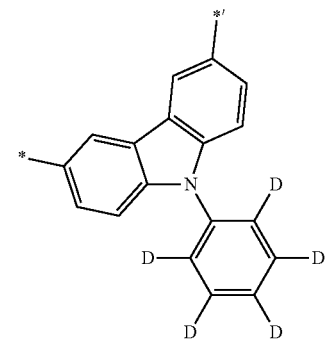

Formula 5O

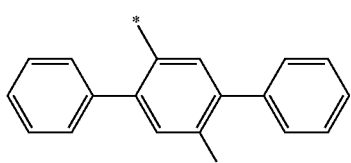

Formula 5P

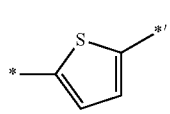

Formula 5Q

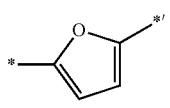

Formula 5R

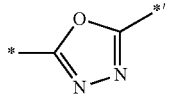

wherein, in Formulae 5A to 5R, * and *' indicate binding sites.

16. The heterocyclic compound of claim 11, wherein $R_1$ to $R_{13}$ are each independently selected from the group consisting of a hydrogen atom, a deuterium atom, a halogen atom, a substituted or unsubstituted methyl group, a substituted or unsubstituted ethyl group, a substituted or unsubstituted propyl group, a substituted or unsubstituted butyl group, and groups represented by Formulae 6A to 6L below; and $R_{14}$ and $R_{15}$ are each independently one of a hydrogen atom, a deuterium atom, and groups represented by Formulae 6A to 6L below:

Formula 6A

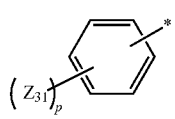

Formula 6B

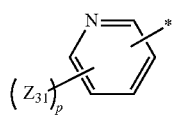

Formula 6C

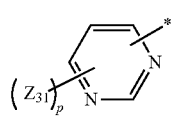

Formula 6D

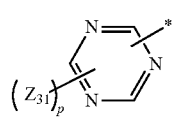

Formula 6E

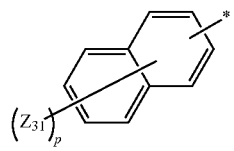

Formula 6F

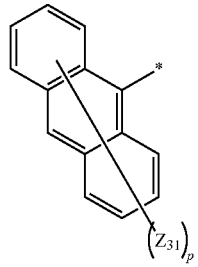

Formula 6G

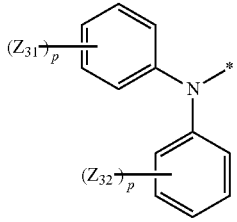

Formula 6H

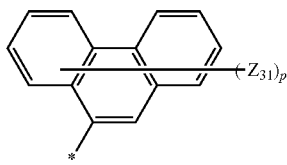

Formula 6I

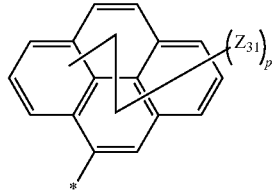

Formula 6J

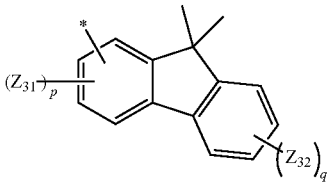

Formula 6K

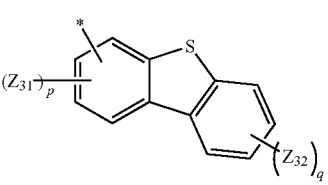

-continued

Formula 6L

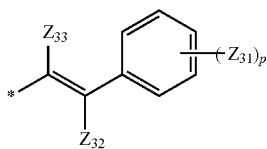

wherein, in Formulae 6A to 6L, $Z_{31}$, $Z_{32}$, and $Z_{33}$ are each independently one of a hydrogen atom, a deuterium atom, a halogen atom, a hydroxyl group, a cyano group, a substituted or unsubstituted methyl group, a substituted or unsubstituted ethyl group, a substituted or unsubstituted propyl group, a substituted or unsubstituted butyl group, a substituted or unsubstituted methoxy group, a substituted or unsubstituted ethoxy group, a substituted or unsubstituted ethenyl group, a substituted or unsubstituted phenyl group, a substituted or unsubstituted naphthyl group, a substituted or unsubstituted anthryl group, a substituted or unsubstituted pyridinyl group, a substituted or unsubstituted carbazolyl group, a substituted or unsubstituted quinolyl group, and a $N(Q_{11})(Q_{12})$ group;

$Q_{11}$ and $Q_{12}$ are each independently one of a hydrogen atom, a deuterium atom, a halogen atom, a hydroxyl group, a substituted or unsubstituted methyl group, a substituted or unsubstituted ethyl group, a substituted or unsubstituted propyl group, a substituted or unsubstituted butyl group, a substituted or unsubstituted pentyl group, a substituted or unsubstituted phenyl group, a substituted or unsubstituted naphthyl group, a substituted or unsubstituted anthryl group, a substituted or unsubstituted fluorenyl group, a substituted or unsubstituted carbazolyl group, and a substituted or unsubstituted pyridinyl group;

a plurality of $Z_{31}$ and $Z_{32}$ are identical to or different from each other;

p is an integer from 1 to 9;

q is an integer from 1 to 5; and

* indicates a binding site.

17. The heterocyclic compound of claim 11, wherein $R_1$ to $R_{13}$ are each independently one of a hydrogen atom, a deuterium atom, a halogen atom, a substituted or unsubstituted methyl group, a substituted or unsubstituted ethyl group, a substituted or unsubstituted propyl group, a substituted or unsubstituted tert-butyl group, a cyano group, —$CD_3$, —$CF_3$, and groups represented by Formulae 7A to 7S below; and $R_{14}$ and $R_{15}$ are each independently one of a hydrogen atom, a deuterium atom, and groups represented by Formulae 7A to 7H below:

Formula 7A

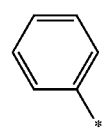

Formula 7B

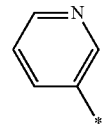

Formula 7C

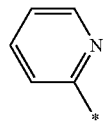

Formula 7D

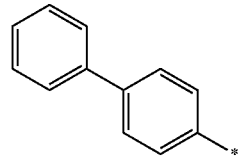

Formula 7E

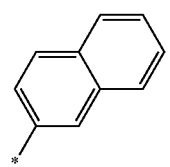

Formula 7F

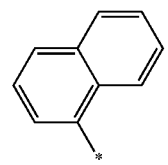

Formula 7G

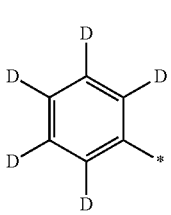

Formula 7H

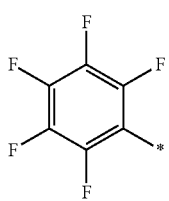

Formula 7I

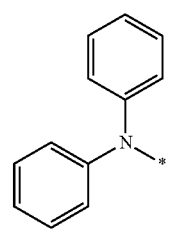

Formula 7J

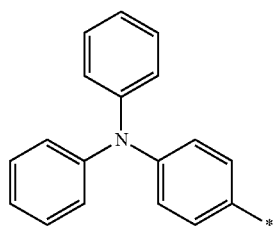

Formula 7K
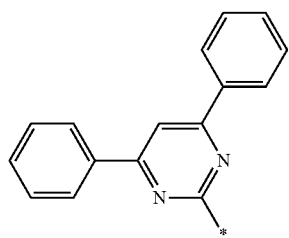
Formula 7L
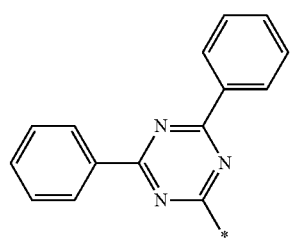
Formula 7M
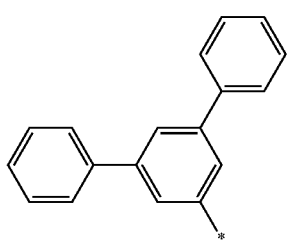
Formula 7N
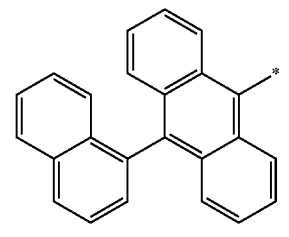
Formula 7O
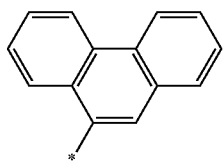
Formula 7P
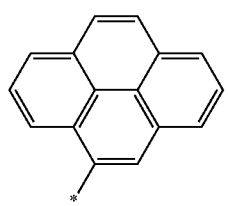
Formula 7Q
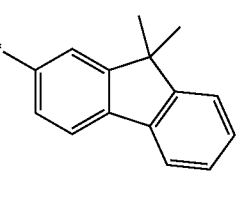
Formula 7R
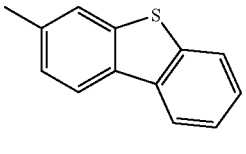
Formula 7S
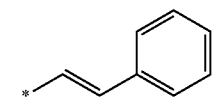
wherein, in Formulae 7A to 7S, * indicates a binding site.
18. The heterocyclic compound of claim 1, wherein the heterocyclic compound of Formula 1A above is one of the compounds represented by Formulae 1 to 75 below:
1
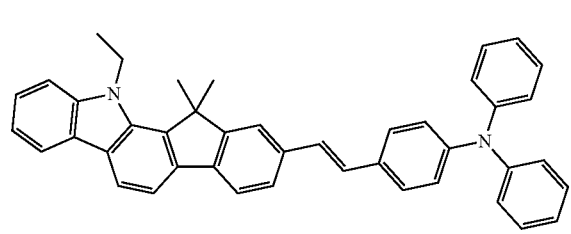
2
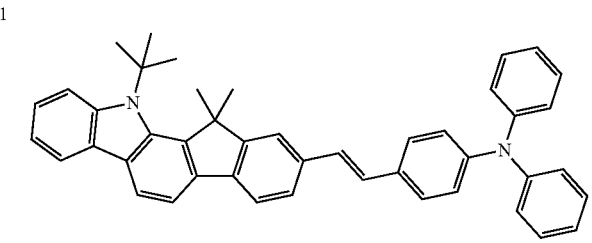
3
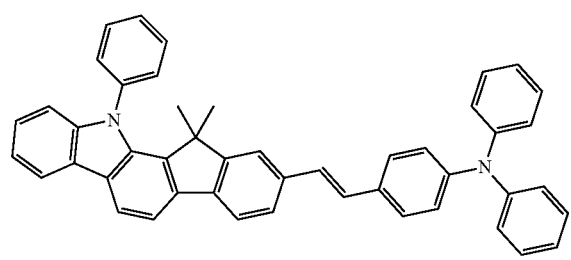
4
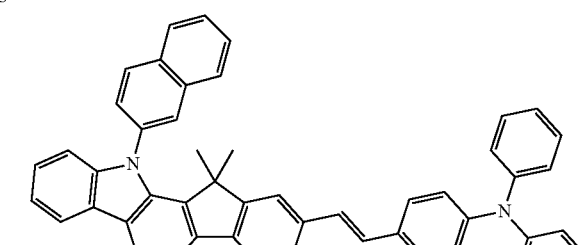

-continued
| 5 | 6 |
|---|---|
| 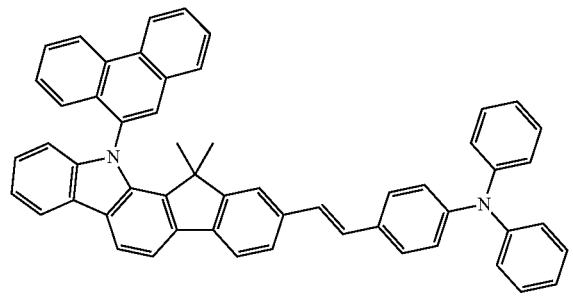 | 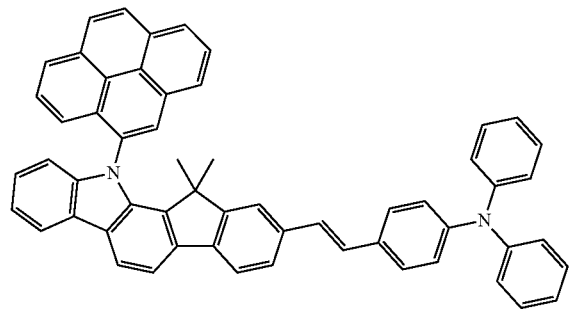 |
| 7 | 8 |
| 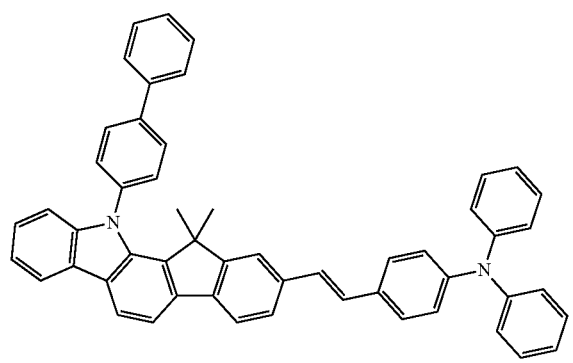 | 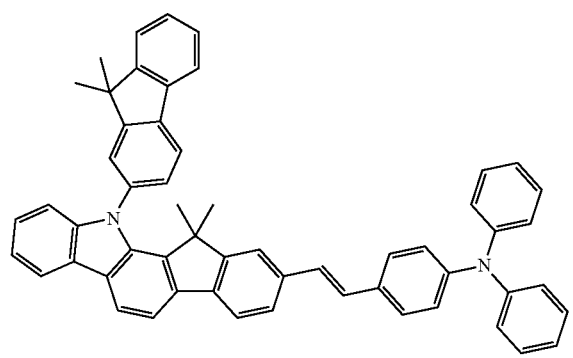 |
| 9 | 10 |
| 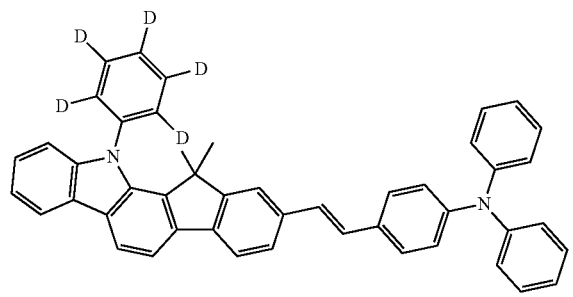 | 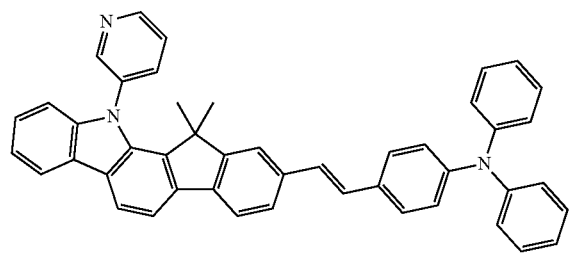 |
| 11 | 12 |
| 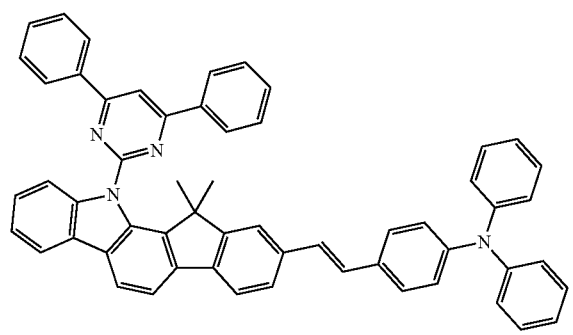 | 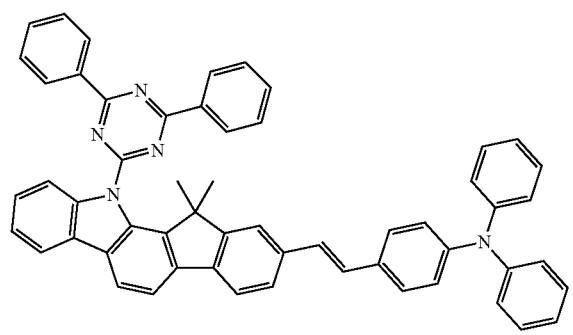 |
| 13 | 14 |
| 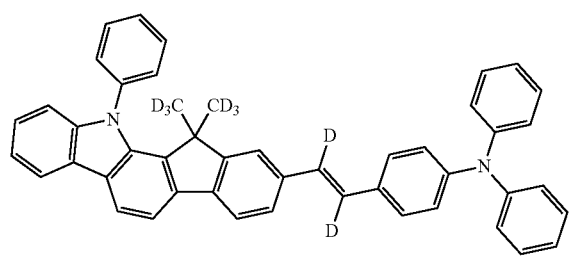 | 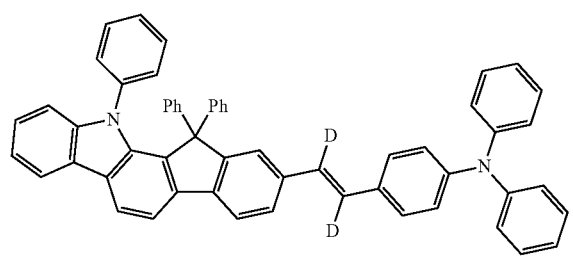 |

-continued
15
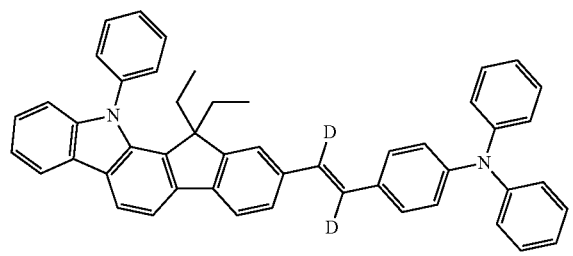
16
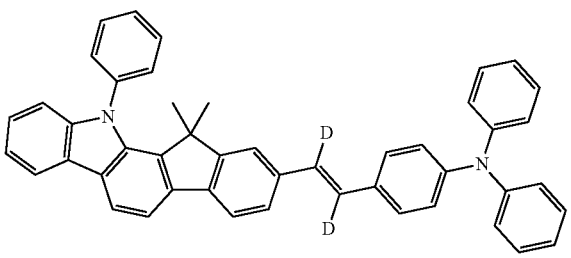
17
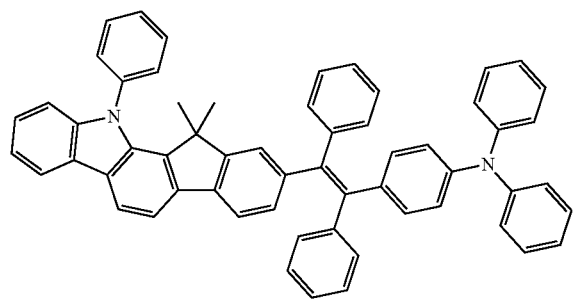
18
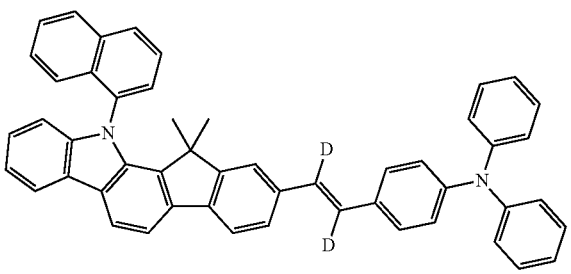
19
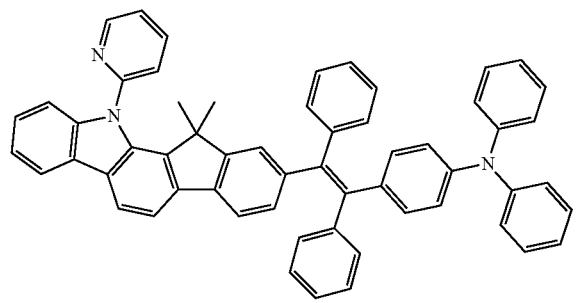
20
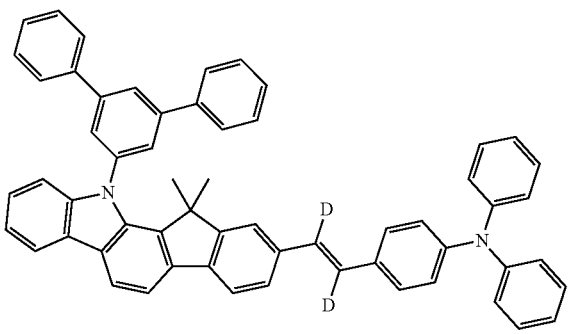
21
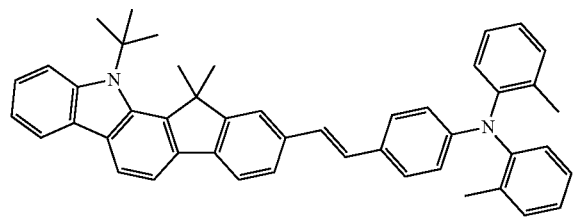
22
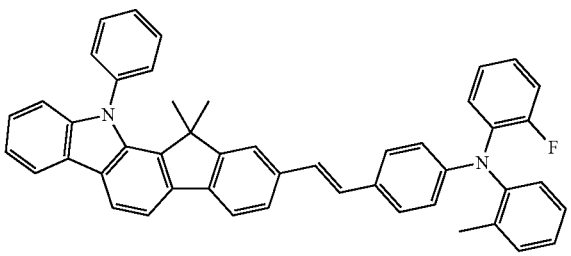
23
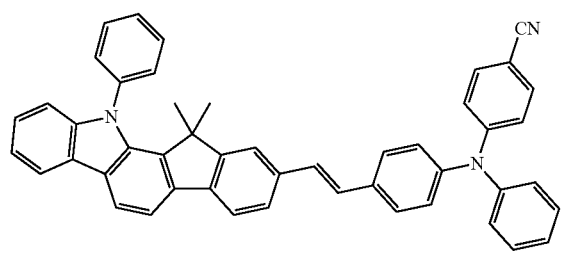
24
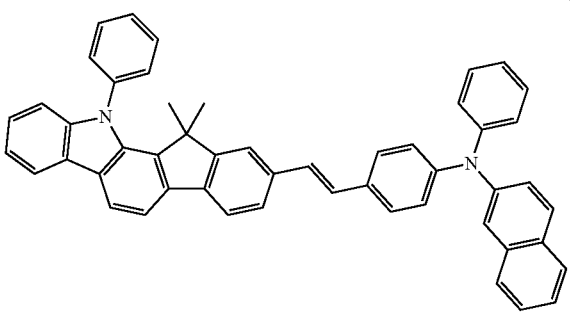

-continued
25
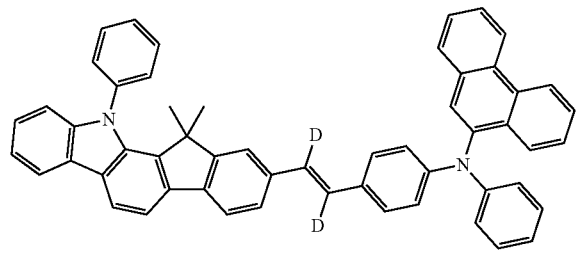
26
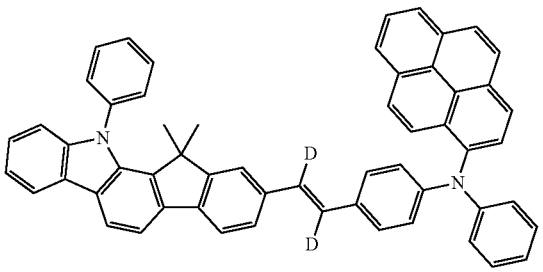
27
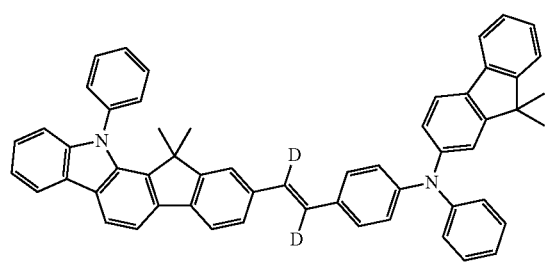
28
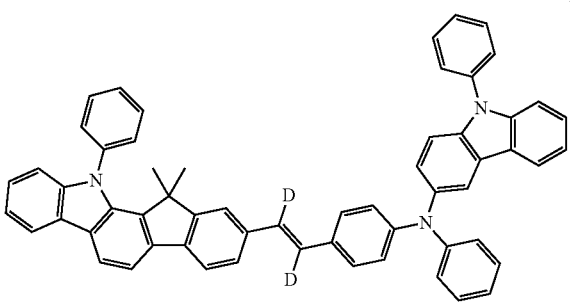
29
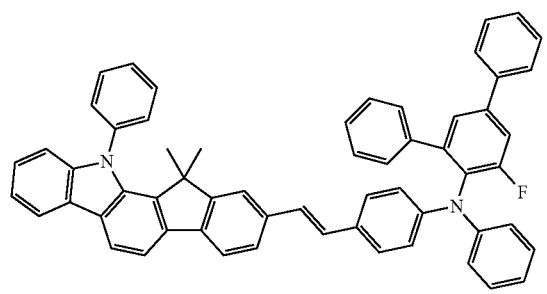
30
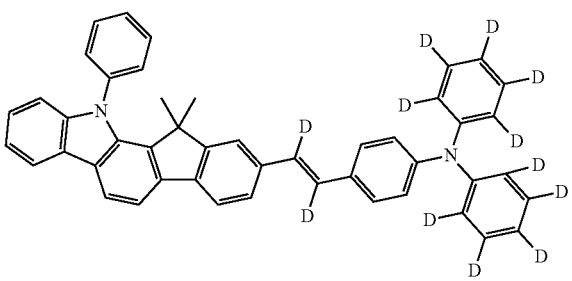
31
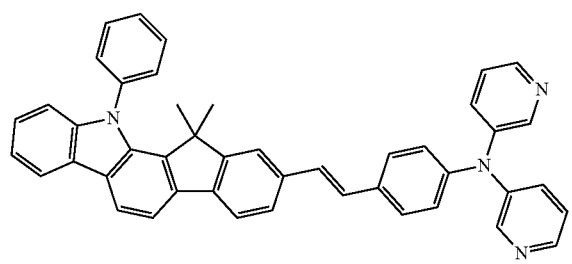
32
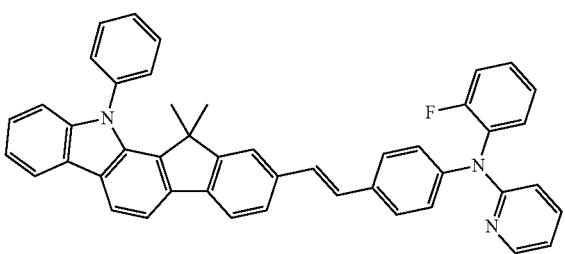
33
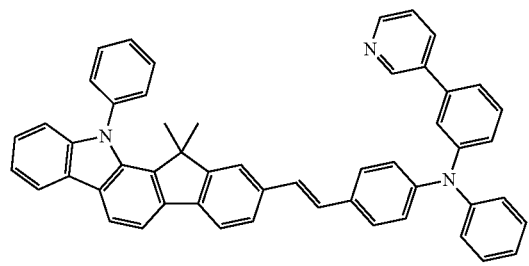
34
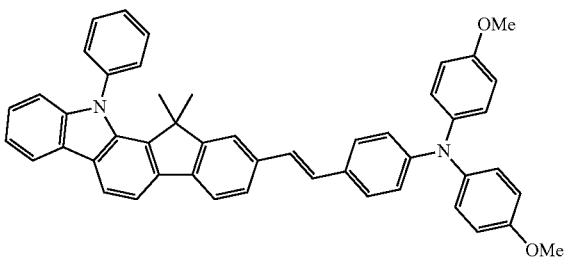

35
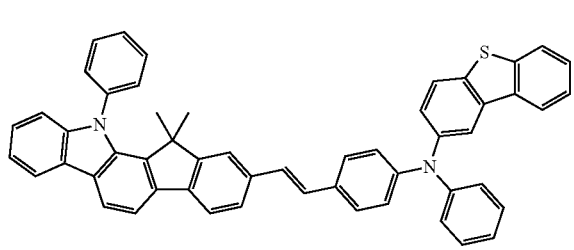
36
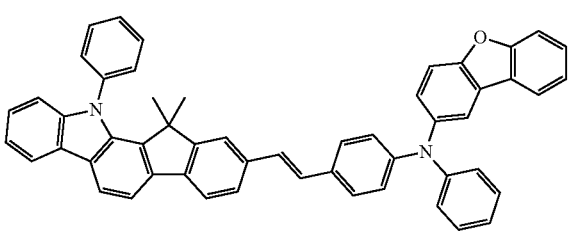
37
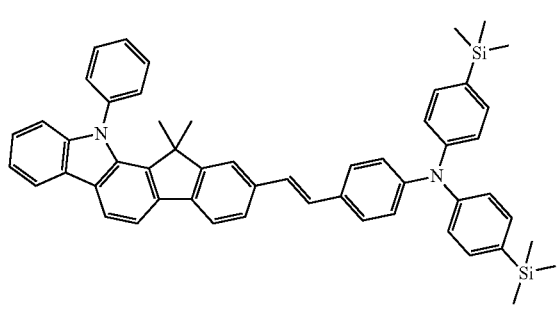
38
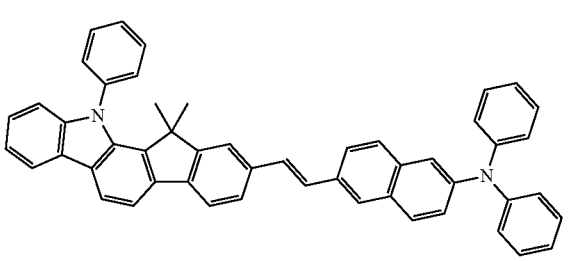
39
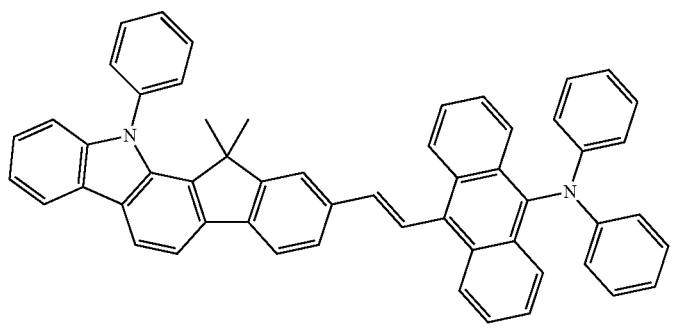
40
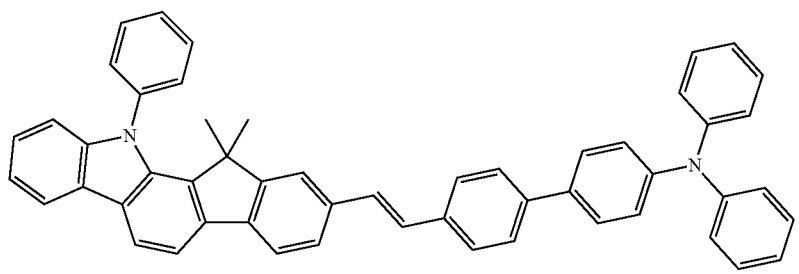
41
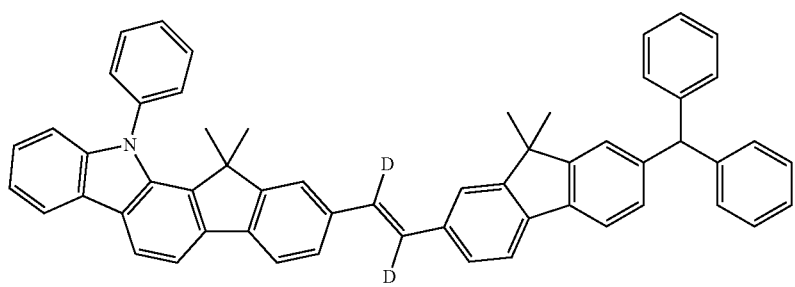

-continued
42
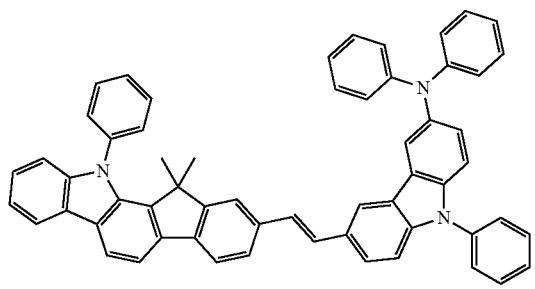
43
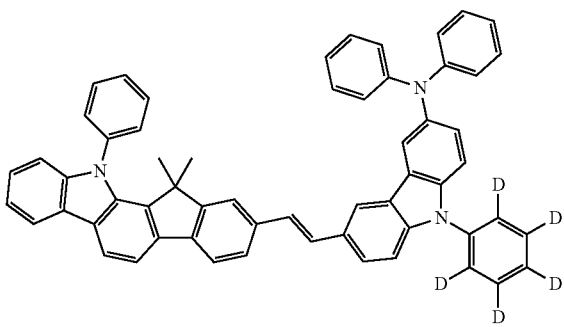
44
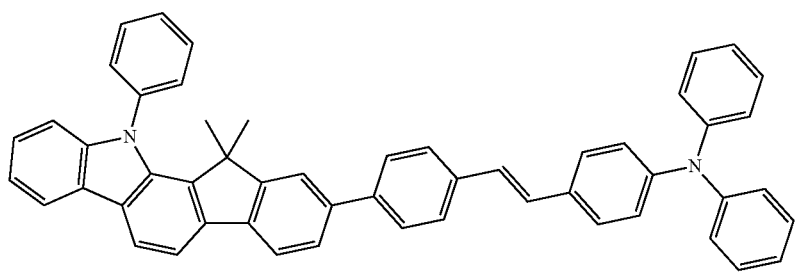
45
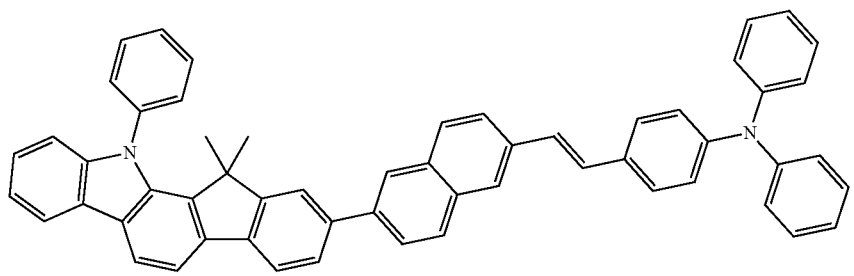
46
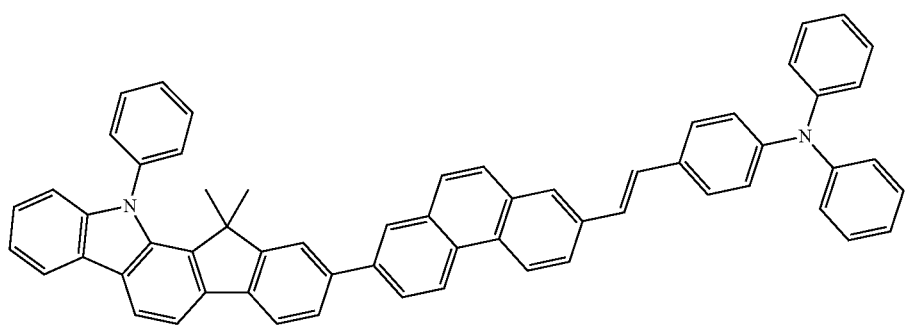
47
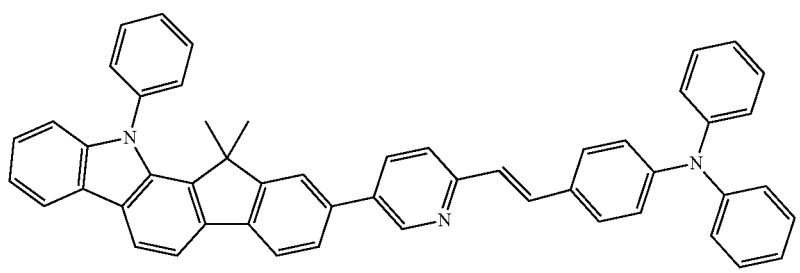

-continued
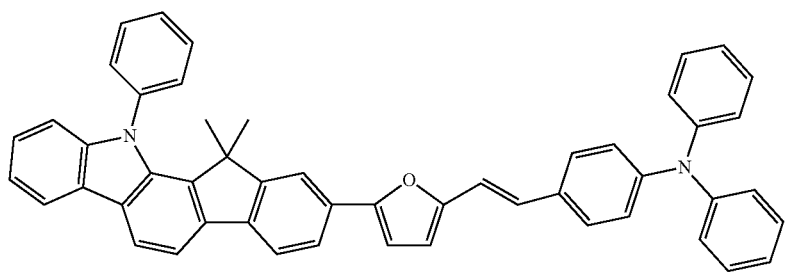
48
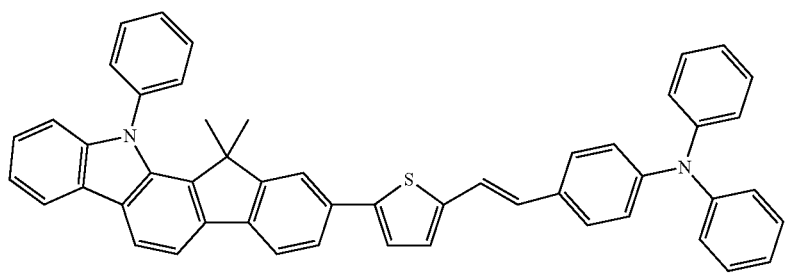
49
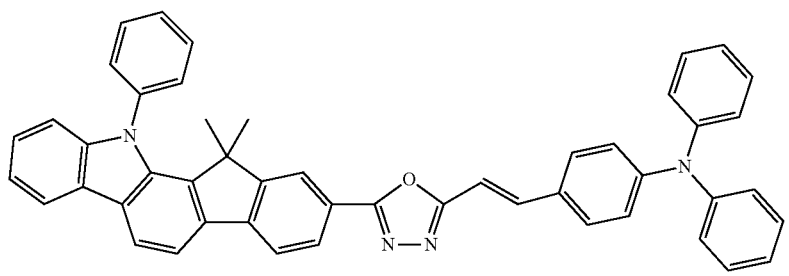
50
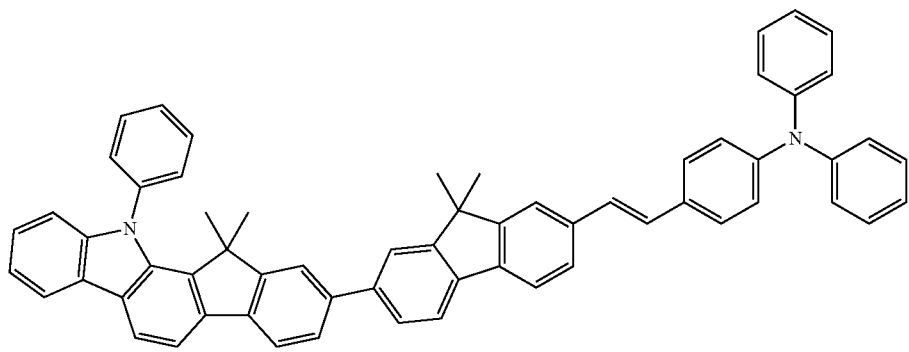
51
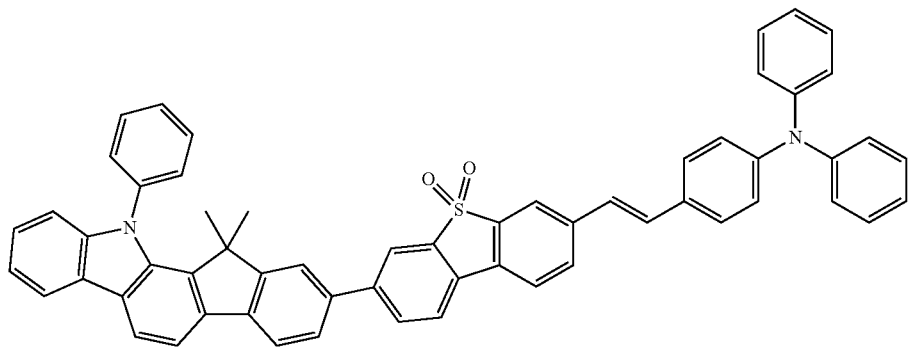
52

-continued
53
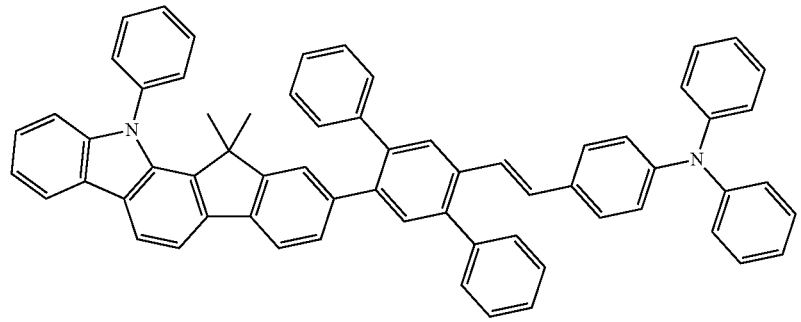
54
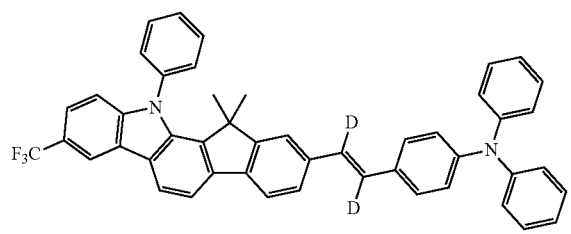
55
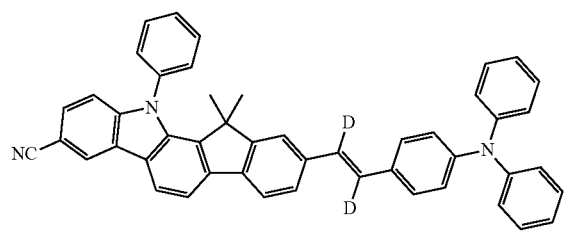
56
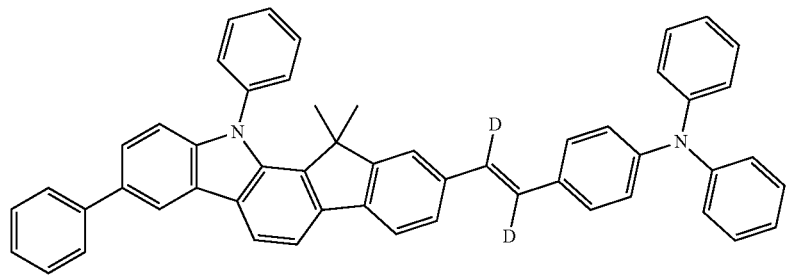
57
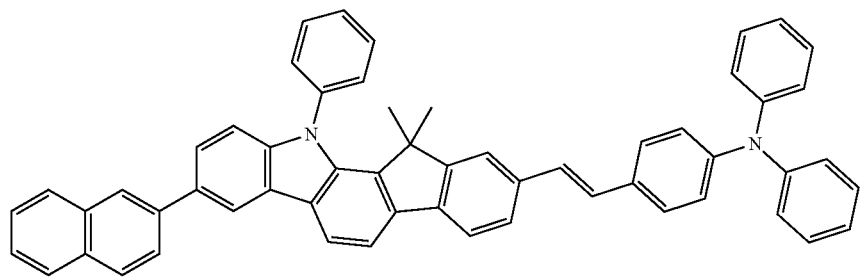
58
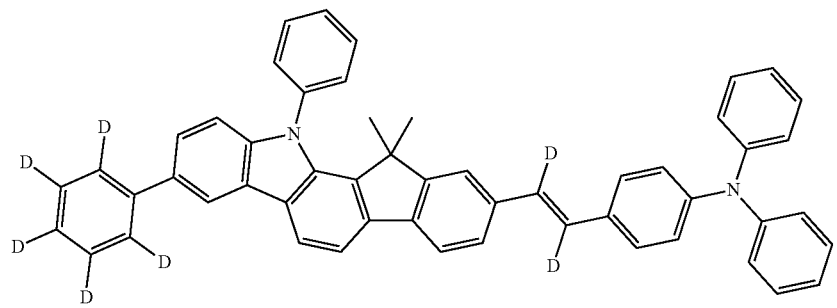

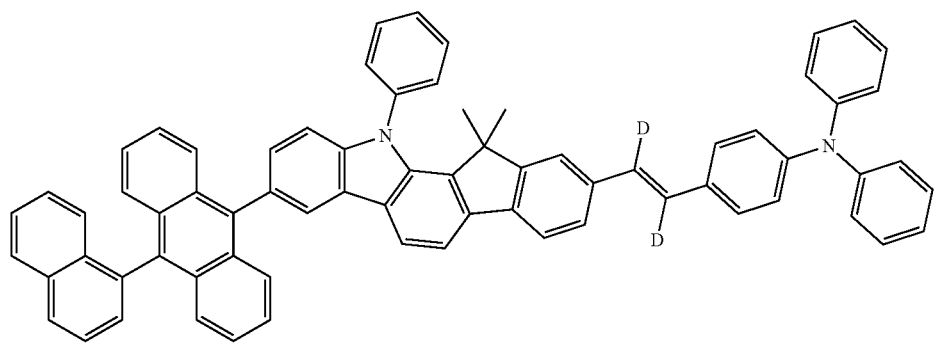
59
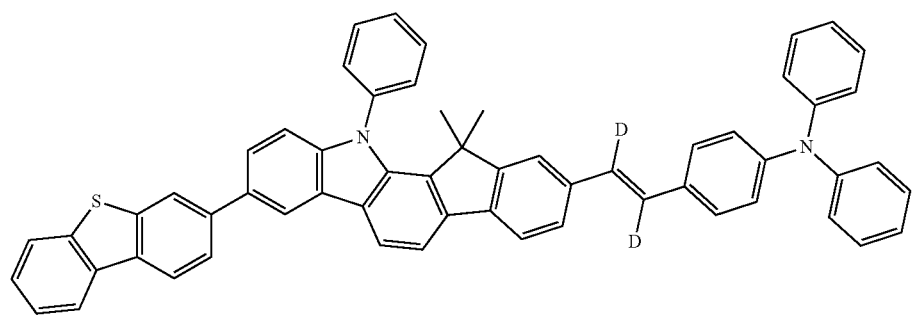
60
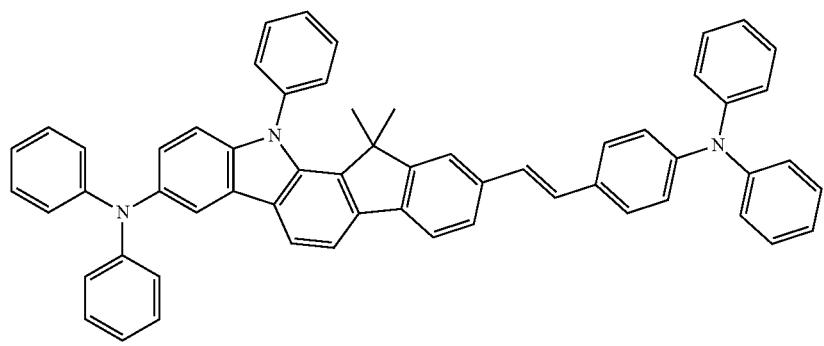
61
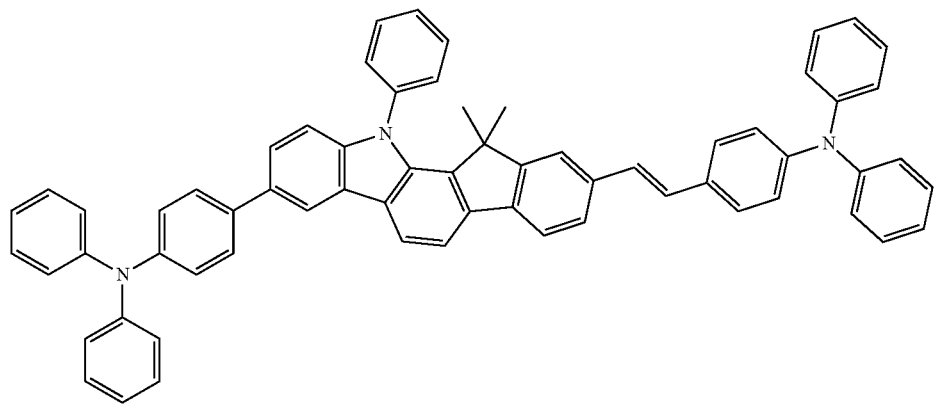
62

-continued
63
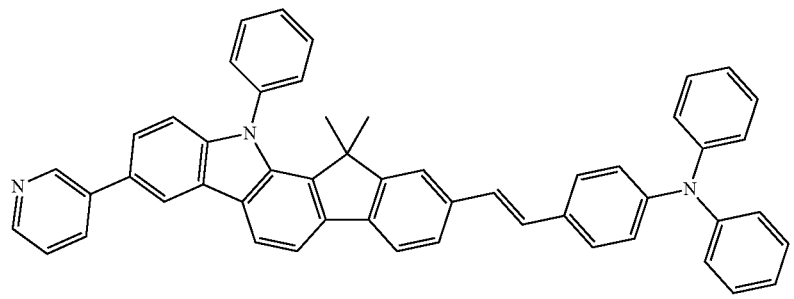
64
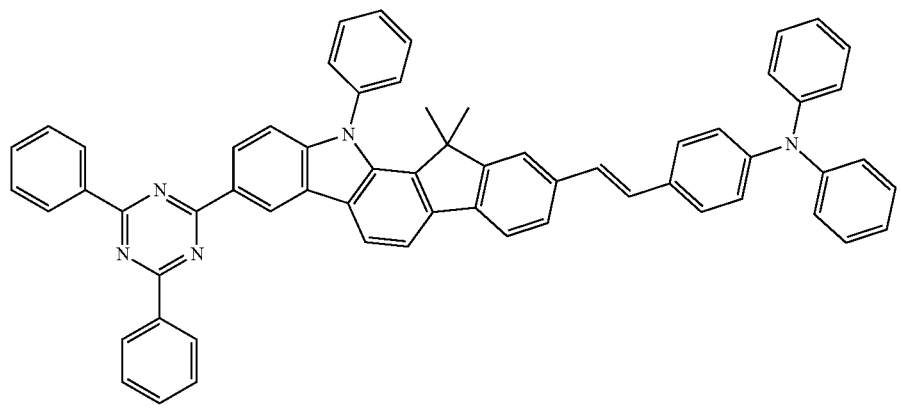
65
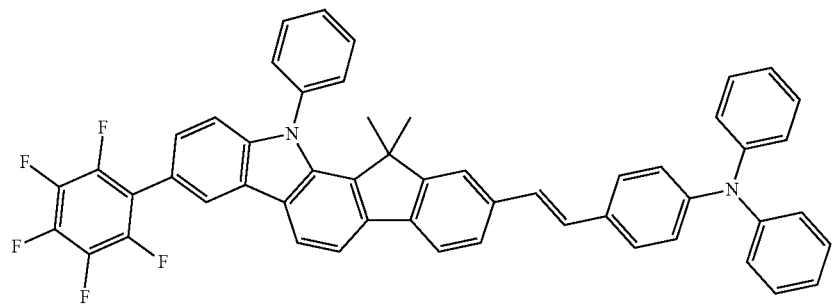
66
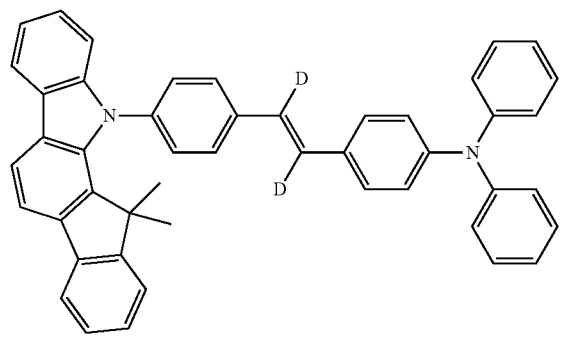
67
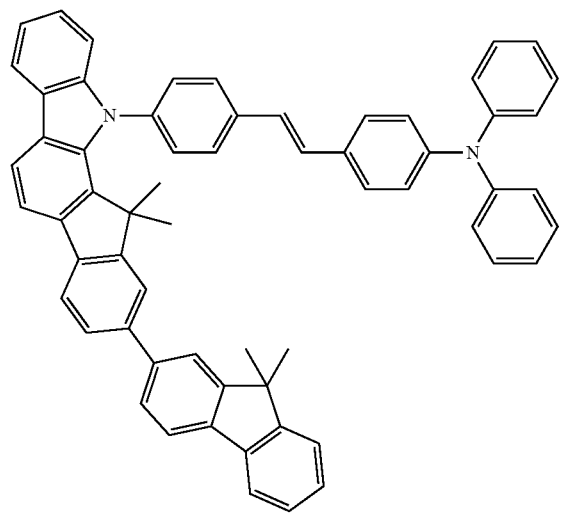

-continued
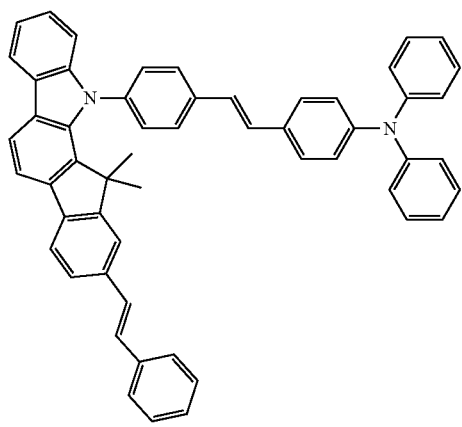
68
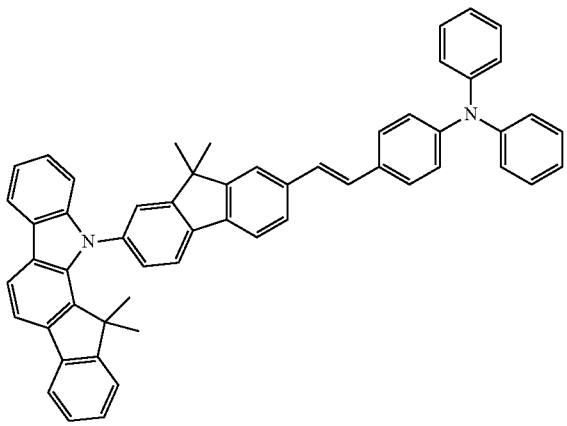
69
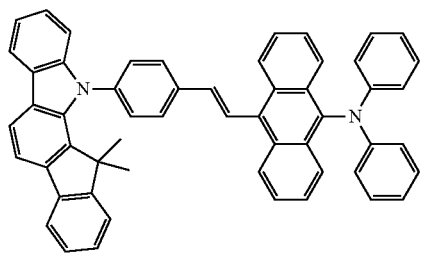
70
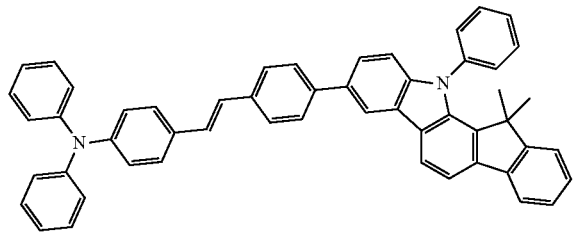
71
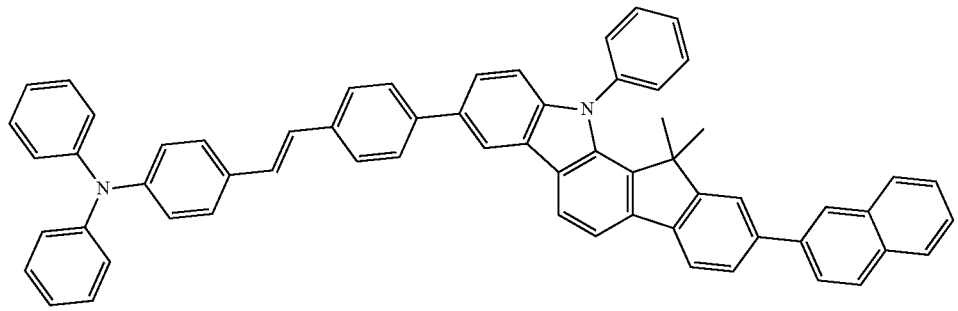
72
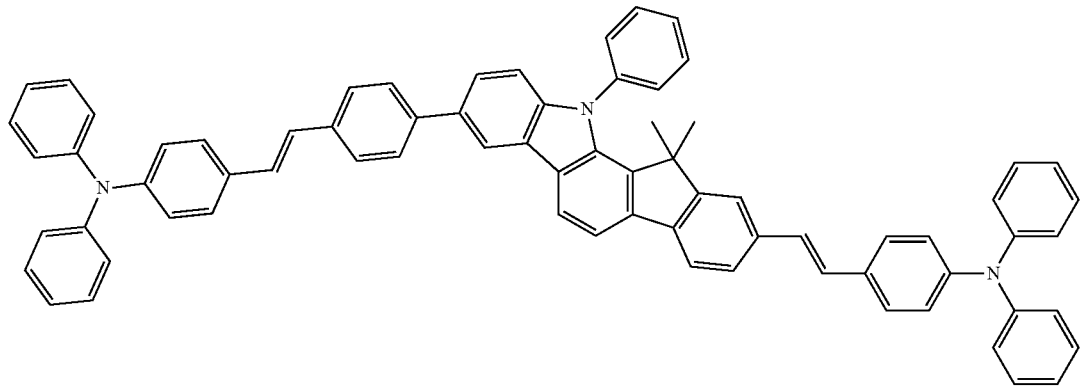
73

74
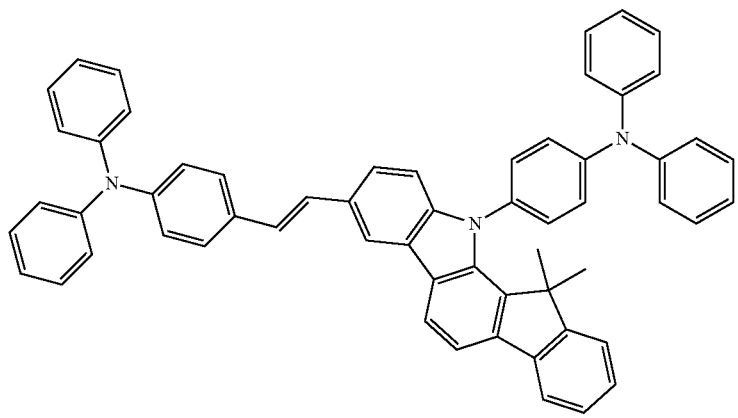
75
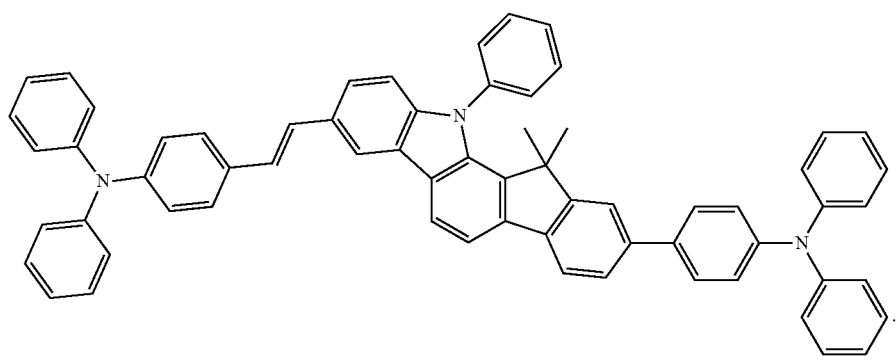
19. The heterocyclic compound of claim 1, wherein the heterocyclic compound of Formula 1A above is one of the compounds represented by Formulae 8, 16, 19, 29, 39, 47, 56, and 62 below:
Compound 8
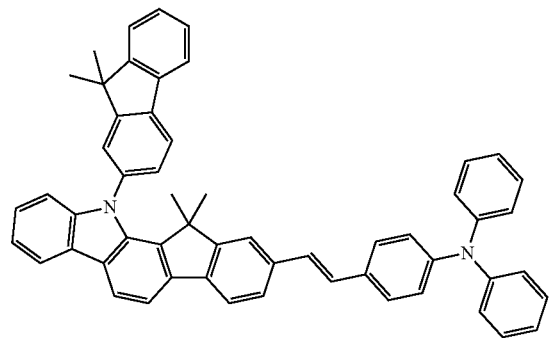
Compound 16
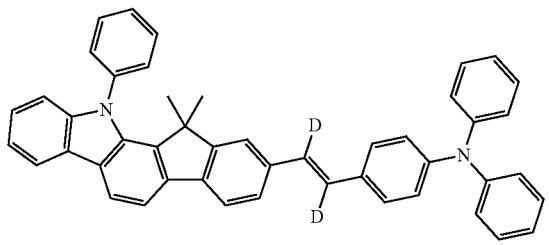
Compound 19
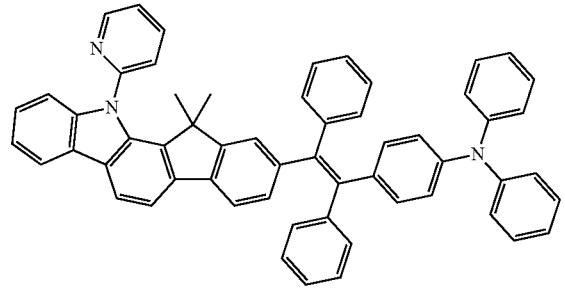
Compound 29
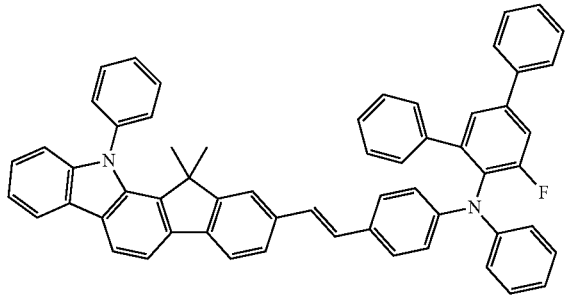

-continued

Compound 39

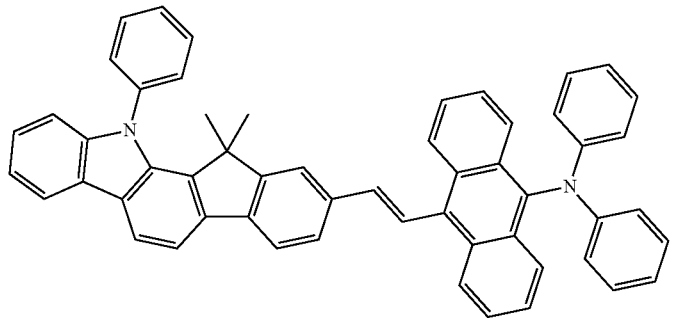

Compound 47

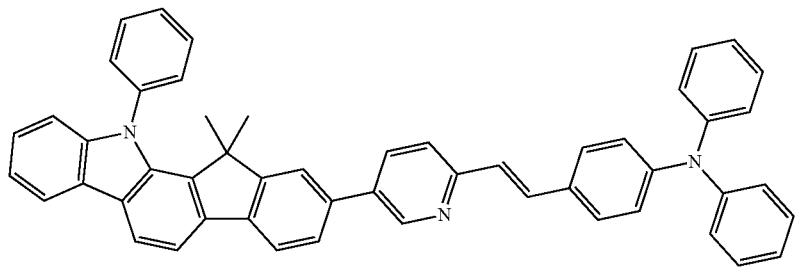

Compound 56

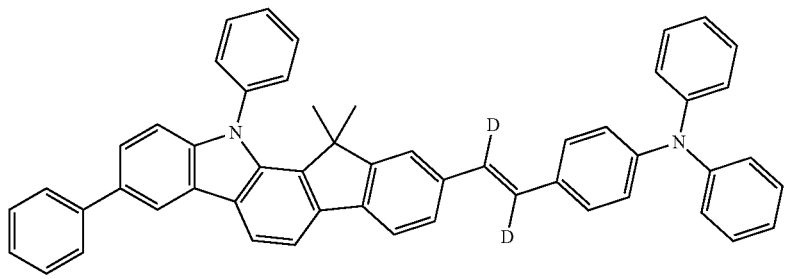

Compound 62

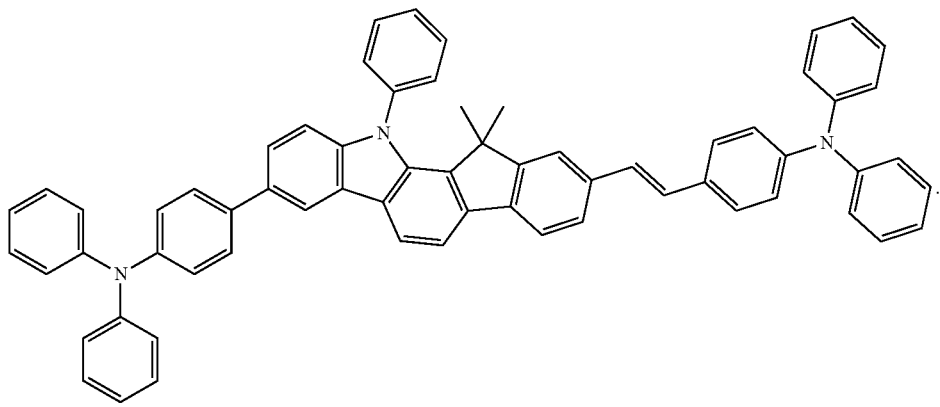

20. An organic light-emitting device comprising:
a first electrode;
a second electrode disposed opposite to the first electrode; and
an organic layer disposed between the first electrode and the second electrode,
wherein the organic layer comprises at least one layer, and comprises at least one of the heterocyclic compound of claim 1.

21. The organic light-emitting device of claim 20, wherein the organic layer comprises at least one of a hole injection layer, a hole transport layer, a hole injection and transport layer having both hole injection and hole transport capabilities, an emission layer, an electron injection layer, an electron transport layer, and an electron injection and transport layer having both electron injection and electron transport capabilities.

22. The organic light-emitting device of claim 21, wherein at least one of the emission layer, the hole injection layer, the hole transport layer, and the hole injection and transport layer comprises the heterocyclic compound.

23. The organic light-emitting device of claim 21, wherein the organic layer comprises the emission layer, the emission layer comprises a host and a dopant, and the heterocyclic compound is a fluorescent host, a phosphorescent host, or a fluorescent dopant of the emission layer.

24. The organic light-emitting device of claim 22, wherein the emission layer is a blue emission layer.

25. The organic light-emitting device of claim 21, wherein the organic layer comprises the emission layer, the emission layer comprises a host and a phosphorescent dopant.

26. The organic light-emitting device of claim 21, wherein at least one of the hole injection layer, the hole transport layer, and the hole injection and transport layer further comprises a charge generating material.

27. The organic light-emitting device of claim 21, whereinthe charge generating material is a p-type dopant.

28. The organic light-emitting device of claim 21, wherein the organic layer comprises the electron transport layer, and the electron transport layer comprises an electron transporting organic compound and a metal-containing material.

29. The organic light-emitting device of claim 28, wherein the metal-containing material comprises a lithium (Li) complex.

30. The organic light-emitting device of claim 20, wherein at least one layer of the organic layer is formed using a wet process.

* * * * *